US007667019B2

(12) United States Patent
Wisnewski et al.

(10) Patent No.: US 7,667,019 B2
(45) Date of Patent: *Feb. 23, 2010

(54) FLEA ULTRASPIRACLE NUCLEIC ACID MOLECULES

(75) Inventors: Nancy Wisnewski, Fort Collins, CO (US); Anna M. Becher, Fort Collins, CO (US); Eric Jarvis, Boulder, CO (US)

(73) Assignee: Heska Corporation, Loveland, CO (US)

( * ) Notice: Subject to any disclaimer, the term of this patent is extended or adjusted under 35 U.S.C. 154(b) by 143 days.

This patent is subject to a terminal disclaimer.

(21) Appl. No.: 11/697,551

(22) Filed: Apr. 6, 2007

(65) Prior Publication Data

US 2007/0231894 A1    Oct. 4, 2007

Related U.S. Application Data

(62) Division of application No. 10/855,541, filed on May 27, 2004, now Pat. No. 7,208,589, which is a division of application No. 10/065,200, filed on Sep. 25, 2002, now Pat. No. 6,767,721, which is a division of application No. 09/435,019, filed on Nov. 5, 1999, now Pat. No. 6,489,140.

(60) Provisional application No. 60/107,559, filed on Nov. 6, 1998.

(51) Int. Cl.
*C07H 21/04* (2006.01)
*A61K 38/00* (2006.01)

(52) U.S. Cl. ............ 536/23.5; 530/388.22; 530/388.24; 530/399

(58) Field of Classification Search ........................ None
See application file for complete search history.

(56) References Cited

U.S. PATENT DOCUMENTS 5,641,652 A * 6/1997 Oro et al. ................ 435/69.1
5,688,691 A * 11/1997 Oro et al. ................ 435/348
6,504,082 B1    1/2003 Albertsen et al.

OTHER PUBLICATIONS

Hu et al. (2003) Transcription activation by the ecdysone receptor (EcR/USP): identification of activation functions. Mol Endocrinol. vol. 17, No. 4, pp. 716-731.*
Tzertzinis et al. (1994) BmCF1, a *Bombyx mori* RXR-type receptor related to the *Drosophila* ultraspiracle. J. Mol. Biol., vol. 238, No. 3, pp. 479-486.*
Oro et al. (1990) Relationship between the product of the *Drosophila* ultraspiracle locus and the vertebrate retinoid X receptor, Nature, vol. 347, issue 6290, pp. 298-301.*
Cooke et al., 1996, GenBank Accession 1350913.
Antoniewski et al., 1993, *Insect Biochem. Molec. Biol.*, vol. 23, No. 1, pp. 105-114.
Antoniewski et al., 1994, *Molecular and Cellular Biology*, vol. 14, No. 7, pp. 4465-4474.
Antoniewski et al., 1996, *Molecular and Cellular Biology*, vol. 16, No. 6, pp. 2977-2986.
Blumberg et al., 1992, *Proc. Natl. Acad. Sci.*, vol. 89, pp. 2321-2325.
Christianson et al., 1992, *Proc. Natl. Acad. Sci. USA*, vol. 89, pp. 11503-11507.
D'Avino et al., 1995, *Molecular and Cellular Endocrinology*, vol. 113, pp. 1-9.
Dhadialla et al., 1997, *Archives of Insect Biochemistry and Physiology*, vol. 35, pp. 45-57.
Elke et al., 1997, *Archives of Insect Biochemistry and Physiology*, vol. 35, pp. 59-69.
Fujiwara et al., 1995, *Insect Biochem. Molecular Biol.*, vol. 25, No. 7, pp. 845-856.
Giguere et al., 1987, *Nature*, vol. 330, pp. 624-629.
Guo et al., 1998, *Molecular and Cellular Endocrinology*, vol. 139, pp. 45-60.
Hannan et al., 1997, *Insect Biochem. Molec. Biol.*, vol. 27, No. 6, pp. 479-488.
Henrich et al., 1990, *Nucleic Acids Research*, vol. 18, No. 14, pp. 4143-4148.
Henrich et al, 1994, *Developmental Biology*, vol. 165, pp. 38-52.
Jindra et al., 1996, *Developmental Biology*, vol. 180, pp. 258-272.
Jindra et al., 1997, *Insect Molecular Biology*, vol. 6, No. 1, pp. 41-53.
Jones et al., 1997, *Proc. Natl. Acad. Sci. USA*, vol, 94, pp. 13499-13503.
Kamimura et al., 1996, *Comp. Biochem. Physiol.*, vol. 113B, No. 2, pp. 341-347.
Kapitskaya et al., 1996, *Molecular and Cellular Endocrinology*, vol. 121, pp. 119-132.
Koelle et al., 1991, *Cell*, vol. 67, pp. 59-77.
Kothapalli et al., 1995, *Developmental Genetics*, vol, 17, pp. 319-330.
Leid et al., 1992, *Cell*, vol. 68, pp. 377-395.
Li et al., 1997, *Proc. Natl. Acad. Sci. USA*, vol. 94, pp. 2278-2283.
Nakagawa et al., 1998, *Pestic. Sci.*, vol. 53. pp. 267-277.
Perera et al.,1998, *Developmental Genetics*, vol. 22, pp. 169-179.
Rauch et al., 1998, *Insect Biochemistry and Molecular Biology*, vol. 28, pp. 265-275.

(Continued)

*Primary Examiner*—Anand U Desai
*Assistant Examiner*—Samuel Liu
(74) *Attorney, Agent, or Firm*—Sheridan Ross, P.C.

(57) ABSTRACT

The present invention relates to flea ecdysone receptor and ultraspiracle proteins; to flea ecdysone receptor and ultraspiracle nucleic acid molecules, including those that encode such flea ecdysone receptor and ultraspiracle proteins; to antibodies raised against such flea ecdysone receptor and ultraspiracle proteins; and to compounds that inhibit flea ecdysone receptor and/or ultraspiracle activity. The present invention also includes methods to obtain such proteins, nucleic acid molecules, antibodies, and inhibitory compounds. Also included in the present invention are therapeutic compositions comprising a protective compound derived from a protein of the present invention that inhibits the binding between ecdysone receptor and ecdysone as well as the use of such therapeutic compositions to protect animals from flea infestation.

6 Claims, No Drawings

OTHER PUBLICATIONS

Rusin et al., 1996, *Acta Biochimica Polonica*, vol. 43, No. 4, pp. 611-621.
Song et al., 1997, *Insect Biochem. Molec. Biol.*, vol. 27, No. 11, pp. 973-982.
Swevers et al., 1996, *Insect Biochem. Molec. Biol.*, vol, 26, No. 3, pp. 217-221.
Swevers et al., *Insect Biochem. Molec. Biol.*, vol. 25, No. 7, pp. 857-866.
Talbot et al., 1993, *Cell*, vol. 73, pp. 1323-1337.
Thummel, Carl S., 1996, *Cell*, vol. 83, pp. 871-877.
Turberg et al., 1988, *J. Insect Physiol.*, vol. 34, No. 8, pp. 797-803.
Turberg et al., 1992, *J. Insect Physiol.*, vol. 38, No. 2, pp. 81-91.
Yao et al., 1992, *Cell*, vol. 71, pp. 63-72.
Yao et al., 1993, *Nature*, vol. 366, pp. 476-479.
Yates et al., 1995, *Molecular and Biochemical Parasitology*, vol. 70, pp. 19-31.
Hu et al., 2003, *Mol. Endocrinol.*, vol. 17, No. 4, pp. 716-731.
Jindra et al., 1997, *Insect Mol. Biol.*, vol. 6, No. 1, pp. 41-53.
Human genome project information, 2006, General terms from sequence databases and other gene resources, http://www.ornl.gov/sci/techresources/Human_Genome/posters chromosome/genejargon.shtml.

* cited by examiner

```
                         SEQUENCE LISTING

<160> NUMBER OF SEQ ID NOS: 79

<210> SEQ ID NO 1
<211> LENGTH: 446
<212> TYPE: DNA
<213> ORGANISM: Ctenocephalides felis

<400> SEQUENCE: 1
tgtttggctg tcggaatgcg ccccgagtgc gtggttcccg aaaaccaatg cgccatgaag      60
cgaaaggaaa agaaggcaca gaaggaaaag gacatcggac caatatcagg taccgttgga     120
aaatctgctg ctcccttagc gaattctgca ttacttcaga agcctgatat tttgcctgcg     180
gtcatgaaat gcgacccatt acctccagaa gcaactaaag tgaaattttt gtcagacaag     240
attcttgctg aaaacagaat tcgaaatgtt ccacctttga ctgcaaatca agaatatgtg     300
atcgcaagat tagtgtggta ccaagatgga tatgaacaac cttctgagga agacctacga     360
aggataatga taagtacacc aggtgaagat gaagctgttg aatttcggca tataactgaa     420
attaccatac ttactgtgca gcttat                                          446

<210> SEQ ID NO 2
<211> LENGTH: 446
<212> TYPE: DNA
<213> ORGANISM: Ctenocephalides felis

<400> SEQUENCE: 2
ataagctgca cagtaagtat ggtaatttca gttatatgcc gaaattcaac agcttcatct      60
tcacctggtg tacttatcat tatccttcgt aggtcttcct cagaaggttg ttcatatcca     120
tcttggtacc acactaatct tgcgatcaca tattcttgat ttgcagtcaa aggtggaaca     180
tttcgaattc tgttttcagc aagaatcttg tctgacaaaa atttcacttt agttgcttct     240
```

```
ggaggtaatg ggtcgcattt catgaccgca ggcaaaatat caggcttctg aagtaatgca      300
gaattcgcta agggagcagc agattttcca acggtacctg atattggtcc gatgtccttt      360
tccttctgtg ccttctttc ctttcgcttc atggcgcatt ggttttcggg aaccacgcac       420
tcggggcgca ttccgacagc caaaca                                           446

<210> SEQ ID NO 3
<211> LENGTH: 350
<212> TYPE: DNA
<213> ORGANISM: Ctenocephalides felis

<400> SEQUENCE: 3
gaagcgaaag gaaaagaagg cacagaagga aaaggacatc ggcaatatca ggtaccgttg       60
gaaaatctgc tgctccctta gcgaattctg cattccttca gaagcctgat attttgcctg     120
cggtcatgaa atgcgaccca ttacctccag aagcaactaa agtgaaattt ttgtcagaca     180
agattcttgc tgaaaacaga attcgaaatg ttccaccttt gactgcaaat caagaatatg     240
tgatcgcaag attagtgtgg taccaagatg gatatgaaca accttctgag gaagacctac     300
gaaggataat gataagtaca ccaggtgaag atgaagctgt tgaatttcgg                350

<210> SEQ ID NO 4
<211> LENGTH: 350
<212> TYPE: DNA
<213> ORGANISM: Ctenocephalides felis

<400> SEQUENCE: 4
ccgaaattca acagcttcat cttcacctgg tgtacttatc attatccttc gtaggtcttc       60
ctcagaaggt tgttcatatc catcttggta ccacactaat cttgcgatca catattcttg     120
atttgcagtc aaaggtggaa catttcgaat tctgttttca gcaagaatct tgtctgacaa     180
aaatttcact ttagttgctt ctggaggtaa tgggtcgcat ttcatgaccg caggcaaaat     240
atcaggcttc tgaaggaatg cagaattcgc taagggagca gcagattttc caacggtacc     300
tgatattgcc gatgtccttt tccttctgtg ccttcttttc ctttcgcttc                 350

<210> SEQ ID NO 5
<211> LENGTH: 2822
<212> TYPE: DNA
<213> ORGANISM: Ctenocephalides felis
<220> FEATURE:
<221> NAME/KEY: CDS
<222> LOCATION: (605)..(2287)

<400> SEQUENCE: 5
gctatatata caagacgcac atgctcatat cactaattat atataaccat taacaattat       60
atgtataatt gtatttgtga atgaaacac atgctaccta aaaactgatt cgtatgccgc      120
tctatcaatc agaatgata attaaacaat ttttttatat tgaaatagaa catattatgt      180
tcatatgtca ataacaaatt ttaaacattc atccaagtta cctatttat gcttttaaga      240 tattatttat ttatttattt tgttttgtaa aatttaaaat tttacataaa tacttttctaa     300 ctatgaatat aaattaatat acaaaagatt tgaaactaa gaggaaaagt aattataatc      360
attttaatca ttaaattata tactcaaaat gatacaatta gattttacag tcacacacat      420
taggtacaga gattcaatta tgaattagga gttgagaaat gctttcgagt aaaatctgca     480
ataagatgac tatattccta aggatgttat gtcagtcata aataaaaatc actatatttt     540
caatttgtgt atggtgatct tctaaaggat aaatgtgtga agtgaaatac cttgcattat     600
```

```
caac atg aaa cga cgt tgg tct aac aac ggt ggc ttc caa acc ttg cgg        649
     Met Lys Arg Arg Trp Ser Asn Asn Gly Gly Phe Gln Thr Leu Arg
       1               5                  10                  15 atg ctc gaa gat gtt gca tct ggt gag gta acg tcg tct tct ggt ggc        697
Met Leu Glu Asp Val Ala Ser Gly Glu Val Thr Ser Ser Ser Gly Gly
                 20                  25                  30 gcc ctg gct gcg ttg agt ccg gct tcg tta ggt tcg ccc gag aca tat        745
Ala Leu Ala Ala Leu Ser Pro Ala Ser Leu Gly Ser Pro Glu Thr Tyr
             35                  40                  45 gcc gag ctg gat ttg tgg gtg tac gag gaa gct ggc tta cat cca ggt        793
Ala Glu Leu Asp Leu Trp Val Tyr Glu Glu Ala Gly Leu His Pro Gly
         50                  55                  60 tca ggt gtg caa gga tgc ggt gcg gtc gcc gcc ttg cca tcg atc gcg        841
Ser Gly Val Gln Gly Cys Gly Ala Val Ala Ala Leu Pro Ser Ile Ala
     65                  70                  75 aca cag gtc ccc cta gga ttg ccc gct atg gac cta ccg cac acg cct        889
Thr Gln Val Pro Leu Gly Leu Pro Ala Met Asp Leu Pro His Thr Pro
 80                  85                  90                  95 cgg agt gac agt gcg ggt agc atc tca tca gga cga gaa gac ctg tca        937
Arg Ser Asp Ser Ala Gly Ser Ile Ser Ser Gly Arg Glu Asp Leu Ser
                100                 105                 110 ccg cct agt tct ttg aac ggc tat tca gca gat ggc tgc gaa gcg aag        985
Pro Pro Ser Ser Leu Asn Gly Tyr Ser Ala Asp Gly Cys Glu Ala Lys
            115                 120                 125 aag gcc aag aaa ggg ccg gcg ccg cgg cag cag gag gaa cta tgt ctt       1033
Lys Ala Lys Lys Gly Pro Ala Pro Arg Gln Gln Glu Glu Leu Cys Leu
        130                 135                 140 gtg tgc ggc gac cgt gcc tcc gga tat cat tac aac gct ctt act tgt       1081
Val Cys Gly Asp Arg Ala Ser Gly Tyr His Tyr Asn Ala Leu Thr Cys
145                 150                 155 gaa gga tgc aaa ggt ttt ttc cga cga agt gtg act aag aat gcc gtg       1129
Glu Gly Cys Lys Gly Phe Phe Arg Arg Ser Val Thr Lys Asn Ala Val
160                 165                 170                 175 tac gtg tgc aag ttt ggg cac acg tgc gaa atg gac atg tat atg cga       1177
Tyr Val Cys Lys Phe Gly His Thr Cys Glu Met Asp Met Tyr Met Arg
                180                 185                 190 cgc aaa tgt cag gaa tgt agg ctc aag aaa tgt ttg gct gtc gga atg       1225
Arg Lys Cys Gln Glu Cys Arg Leu Lys Lys Cys Leu Ala Val Gly Met
            195                 200                 205 cgc ccc gag tgc gtg gtt ccc gaa aac caa tgc gcc atg aag cga aag       1273
Arg Pro Glu Cys Val Val Pro Glu Asn Gln Cys Ala Met Lys Arg Lys
        210                 215                 220 gaa aag aag gca cag aag gaa aag gac atc gga cca ata tca ggt acc       1321
Glu Lys Lys Ala Gln Lys Glu Lys Asp Ile Gly Pro Ile Ser Gly Thr
    225                 230                 235 gtt gga aaa tct gct gct ccc tta gcg aat tct gca tta ctt cag aag       1369
Val Gly Lys Ser Ala Ala Pro Leu Ala Asn Ser Ala Leu Leu Gln Lys
240                 245                 250                 255 cct gat att ttg cct gcg gtc atg aaa tgc gac cca tta cct cca gaa       1417
Pro Asp Ile Leu Pro Ala Val Met Lys Cys Asp Pro Leu Pro Pro Glu
                260                 265                 270 gca act aaa gtg aaa ttt ttg tca gac aag att ctt gct gaa aac aga       1465
Ala Thr Lys Val Lys Phe Leu Ser Asp Lys Ile Leu Ala Glu Asn Arg
            275                 280                 285 att cga aat gtt cca cct ttg act gca aat caa gaa tat gtg atc gca       1513
Ile Arg Asn Val Pro Pro Leu Thr Ala Asn Gln Glu Tyr Val Ile Ala
        290                 295                 300 aga tta gtg tgg tac caa gat gga tat gaa caa cct tct gag gaa gac       1561
Arg Leu Val Trp Tyr Gln Asp Gly Tyr Glu Gln Pro Ser Glu Glu Asp
```

-continued

```
              305                 310                 315
cta cga agg ata atg ata agt aca cca gct gaa gat gaa gct ctt gaa     1609
Leu Arg Arg Ile Met Ile Ser Thr Pro Ala Glu Asp Glu Ala Leu Glu
320                 325                 330                 335 ttt cgg cat ata act gaa att acc ata ctt act gtg cag ctt ata gtg     1657
Phe Arg His Ile Thr Glu Ile Thr Ile Leu Thr Val Gln Leu Ile Val
                340                 345                 350 gaa ttt gca aag ggt tta cca gct ttt acc aaa ata cca caa gaa gat     1705
Glu Phe Ala Lys Gly Leu Pro Ala Phe Thr Lys Ile Pro Gln Glu Asp
            355                 360                 365 caa ata aca tta tta aag gca tgt tca agt gaa gta atg atg ctg cga     1753
Gln Ile Thr Leu Leu Lys Ala Cys Ser Ser Glu Val Met Met Leu Arg
        370                 375                 380 atg gct cgg cgg tac gat gca gtg tcg gat tca atc tta ttc gcg aat     1801
Met Ala Arg Arg Tyr Asp Ala Val Ser Asp Ser Ile Leu Phe Ala Asn
    385                 390                 395 aat cgt tca tat act cgt gac tcc tat aaa atg gct ggt atg gca gat     1849
Asn Arg Ser Tyr Thr Arg Asp Ser Tyr Lys Met Ala Gly Met Ala Asp
400                 405                 410                 415 aca ata gaa gat cta ttg cat ttt tgt cga cag atg tat act atg act     1897
Thr Ile Glu Asp Leu Leu His Phe Cys Arg Gln Met Tyr Thr Met Thr
                420                 425                 430 gta gac aat gtg gag tat gca cta ata aca gca att gtg att ttt tca     1945
Val Asp Asn Val Glu Tyr Ala Leu Ile Thr Ala Ile Val Ile Phe Ser
            435                 440                 445 gat cga cct gga ttg gaa caa gca gat ctt gtg gaa caa att caa agt     1993
Asp Arg Pro Gly Leu Glu Gln Ala Asp Leu Val Glu Gln Ile Gln Ser
        450                 455                 460 tat tac atc aaa aca tta aag tgc tac att ttg aat cga cat agt ggt     2041
Tyr Tyr Ile Lys Thr Leu Lys Cys Tyr Ile Leu Asn Arg His Ser Gly
    465                 470                 475 gac cct aag tgt gga ata ttg ttt gcc aaa ctt ctt tct att ctt act     2089
Asp Pro Lys Cys Gly Ile Leu Phe Ala Lys Leu Leu Ser Ile Leu Thr
480                 485                 490                 495 gaa tta cgc acg tta gga aat caa aac tca gaa atg tgt ttt gca ctg     2137
Glu Leu Arg Thr Leu Gly Asn Gln Asn Ser Glu Met Cys Phe Ala Leu
                500                 505                 510 aaa ttg aag aac aga aaa ctt cct aga ttt tta gaa gaa att tgg gat     2185
Lys Leu Lys Asn Arg Lys Leu Pro Arg Phe Leu Glu Glu Ile Trp Asp
            515                 520                 525 gtg aca gat aat gtg cct cct acg ata gac agc atg cat agt gta tcg     2233
Val Thr Asp Asn Val Pro Pro Thr Ile Asp Ser Met His Ser Val Ser
        530                 535                 540 gag aat ttc tat aat aat gaa agt aat ggt acc agt gat tct aca cca     2281
Glu Asn Phe Tyr Asn Asn Glu Ser Asn Gly Thr Ser Asp Ser Thr Pro
    545                 550                 555 atg taa agtgctcaga aaatcaacag ctcttttgca tatttgttta ctgtgtactg      2337
Met
560 gtatggaaaa ttaaggtaac attaaaatat tacataagca ccatgggaaa aggccgttaa   2397 ggcaatattt ttgaataaat aatctattga gacggtacca atggtaaact tggaaaaaat   2457 tcttctgttt acatattagg agccaagtta agaataagt atgaatgatt gttgataaat    2517 tgcttgtgta acacttcaat ggccttcaat aaaataatgt ttaacaacgt cgataggaaa   2577 ttaaaaagaa atcatgtgta ataaaatcat tgtaggccg gccatactga tttacctata   2637 ttaagcagaa acttcttaat gtataaatat attttttgctt tgcaaggtaa aaccttctca  2697 atgcaacaat gaattatata tataaacatt gattatttta tcgttagaat ttgaattttg   2757
```

-continued

```
tgttgtggga gaattgtatt tggattagat aaataggctg tgaaaataa aaaaaaaaaa    2817 aaaaa                                                                2822
```

<210> SEQ ID NO 6
<211> LENGTH: 560
<212> TYPE: PRT
<213> ORGANISM: Ctenocephalides felis

<400> SEQUENCE: 6

```
Met Lys Arg Arg Trp Ser Asn Asn Gly Gly Phe Gln Thr Leu Arg Met
1               5                   10                  15

Leu Glu Asp Val Ala Ser Gly Glu Val Thr Ser Ser Ser Gly Gly Ala
            20                  25                  30

Leu Ala Leu Ser Pro Ala Ser Leu Gly Ser Pro Glu Thr Tyr Ala
        35                  40                  45

Glu Leu Asp Leu Trp Val Tyr Glu Glu Ala Gly Leu His Pro Gly Ser
    50                  55                  60

Gly Val Gln Gly Cys Gly Ala Val Ala Ala Leu Pro Ser Ile Ala Thr
65                  70                  75                  80

Gln Val Pro Leu Gly Leu Pro Ala Met Asp Leu Pro His Thr Pro Arg
                85                  90                  95

Ser Asp Ser Ala Gly Ser Ile Ser Ser Gly Arg Glu Asp Leu Ser Pro
            100                 105                 110

Pro Ser Ser Leu Asn Gly Tyr Ser Ala Asp Gly Cys Glu Ala Lys Lys
        115                 120                 125

Ala Lys Lys Gly Pro Ala Pro Arg Gln Gln Glu Glu Leu Cys Leu Val
    130                 135                 140

Cys Gly Asp Arg Ala Ser Gly Tyr His Tyr Asn Ala Leu Thr Cys Glu
145                 150                 155                 160

Gly Cys Lys Gly Phe Phe Arg Arg Ser Val Thr Lys Asn Ala Val Tyr
                165                 170                 175

Val Cys Lys Phe Gly His Thr Cys Glu Met Asp Met Tyr Met Arg Arg
            180                 185                 190

Lys Cys Gln Glu Cys Arg Leu Lys Lys Cys Leu Ala Val Gly Met Arg
        195                 200                 205

Pro Glu Cys Val Val Pro Glu Asn Gln Cys Ala Met Lys Arg Lys Glu
    210                 215                 220

Lys Lys Ala Gln Lys Glu Lys Asp Ile Gly Pro Ile Ser Gly Thr Val
225                 230                 235                 240

Gly Lys Ser Ala Ala Pro Leu Ala Asn Ser Ala Leu Leu Gln Lys Pro
                245                 250                 255

Asp Ile Leu Pro Ala Val Met Lys Cys Asp Pro Leu Pro Pro Glu Ala
            260                 265                 270

Thr Lys Val Lys Phe Leu Ser Asp Lys Ile Leu Ala Glu Asn Arg Ile
        275                 280                 285

Arg Asn Val Pro Pro Leu Thr Ala Asn Gln Glu Tyr Val Ile Ala Arg
    290                 295                 300

Leu Val Trp Tyr Gln Asp Gly Tyr Glu Gln Pro Ser Glu Glu Asp Leu
305                 310                 315                 320

Arg Arg Ile Met Ile Ser Thr Pro Ala Glu Asp Glu Ala Leu Glu Phe
                325                 330                 335

Arg His Ile Thr Glu Ile Thr Ile Leu Thr Val Gln Leu Ile Val Glu
            340                 345                 350
```

```
Phe Ala Lys Gly Leu Pro Ala Phe Thr Lys Ile Pro Gln Glu Asp Gln
            355                 360                 365
Ile Thr Leu Leu Lys Ala Cys Ser Ser Glu Val Met Met Leu Arg Met
        370                 375                 380
Ala Arg Arg Tyr Asp Ala Val Ser Asp Ser Ile Leu Phe Ala Asn Asn
385                 390                 395                 400
Arg Ser Tyr Thr Arg Asp Ser Tyr Lys Met Ala Gly Met Ala Asp Thr
                405                 410                 415
Ile Glu Asp Leu Leu His Phe Cys Arg Gln Met Tyr Thr Met Thr Val
            420                 425                 430
Asp Asn Val Glu Tyr Ala Leu Ile Thr Ala Ile Val Ile Phe Ser Asp
        435                 440                 445
Arg Pro Gly Leu Glu Gln Ala Asp Leu Val Glu Gln Ile Gln Ser Tyr
    450                 455                 460
Tyr Ile Lys Thr Leu Lys Cys Tyr Ile Leu Asn Arg His Ser Gly Asp
465                 470                 475                 480
Pro Lys Cys Gly Ile Leu Phe Ala Lys Leu Leu Ser Ile Leu Thr Glu
                485                 490                 495
Leu Arg Thr Leu Gly Asn Gln Asn Ser Glu Met Cys Phe Ala Leu Lys
            500                 505                 510
Leu Lys Asn Arg Lys Leu Pro Arg Phe Leu Glu Glu Ile Trp Asp Val
        515                 520                 525
Thr Asp Asn Val Pro Pro Thr Ile Asp Ser Met His Ser Val Ser Glu
    530                 535                 540
Asn Phe Tyr Asn Asn Glu Ser Asn Gly Thr Ser Asp Ser Thr Pro Met
545                 550                 555                 560

<210> SEQ ID NO 7
<211> LENGTH: 2822
<212> TYPE: DNA
<213> ORGANISM: Ctenocephalides felis

<400> SEQUENCE: 7
tttttttttt tttttttttt tttcacagcc tatttatcta atccaaatac aattctccca      60
caacacaaaa ttcaaattct aacgataaaa taatcaatgt ttatatatat aattcattgt     120
tgcattgaga aggttttacc ttgcaaagca aaaatatatt tatacattaa gaagtttctg     180
cttaatatag gtaaatcagt atggccggcc tacaaatgat tttattacac atgatttctt     240
tttaatttcc tatcgacgtt gttaaacatt atttattga aggccattga agtgttacac      300
aagcaattta tcaacaatca ttcatactta ttctttaact tggctcctaa tatgtaaaca     360
gaagaatttt ttccaagttt accattggta ccgtctcaat agattattta ttcaaaaata     420
ttgccttaac ggccttttcc catggtgctt atgtaatatt ttaatgttac cttaattttc     480
cataccagta cacagtaaac aaatatgcaa aagagctgtt gattttctga gcactttaca     540
ttggtgtaga atcactggta ccattacttt cattattata gaaattctcc gatacactat     600
gcatgctgtc tatcgtagga ggcacattat ctgtcacatc ccaaatttct tctaaaaatc     660
taggaagttt tctgttcttc aatttcagtg caaaacacat ttctgagttt tgatttccta     720
acgtgcgtaa ttcagtaaga atagaaagaa gtttggcaaa caatattcca cacttagggt     780
caccactatg tcgattcaaa atgtagcact ttaatgtttt gatgtaataa ctttgaattt     840
gttccacaag atctgcttgt tccaatccag gtcgatctga aaaaatcaca attgctgtta     900
ttagtgcata ctccacattg tctacagtca tagtatacat ctgtcgacaa aaatgcaata     960
```

-continued

```
gatcttctat tgtatctgcc ataccagcca ttttatagga gtcacgagta tatgaacgat    1020
tattcgcgaa taagattgaa tccgacactg catcgtaccg ccgagccatt cgcagcatca    1080
ttacttcact tgaacatgcc tttaataatg ttatttgatc ttcttgtggt attttggtaa    1140
aagctggtaa acccttgca aattccacta taagctgcac agtaagtatg gtaatttcag     1200
ttatatgccg aaattcaaga gcttcatctt cagctggtgt acttatcatt atccttcgta    1260
ggtcttcctc agaaggttgt tcatatccat cttggtacca cactaatctt gcgatcacat    1320
attcttgatt tgcagtcaaa ggtggaacat ttcgaattct gttttcagca agaatcttgt    1380
ctgacaaaaa tttcactta gttgcttctg gaggtaatgg gtcgcatttc atgaccgcag     1440
gcaaaatatc aggcttctga agtaatgcag aattcgctaa gggagcagca gattttccaa    1500
cggtacctga tattggtccg atgtcctttt ccttctgtgc cttctttttcc tttcgcttca    1560
tggcgcattg gttttcggga accacgcact cggggcgcat tccgacagcc aaacatttct    1620
tgagcctaca ttcctgacat ttgcgtcgca tatacatgtc catttcgcac gtgtgcccaa    1680
acttgcacac gtacacggca ttcttagtca cacttcgtcg gaaaaaacct ttgcatcctt    1740
cacaagtaag agcgttgtaa tgatatccgg aggcacggtc gccgcacaca agacatagtt    1800
cctcctgctg ccgcggcgcc ggccctttct tggccttctt cgcttcgcag ccatctgctg    1860
aatagccgtt caaagaacta ggcggtgaca ggtcttctcg tcctgatgag atgctacccg    1920
cactgtcact ccgaggcgtg tgcggtaggt ccatagcggg caatcctagg gggacctgtg    1980
tcgcgatcga tggcaaggcg gcgaccgcac cgcatccttg cacacctgaa cctggatgta    2040
agccagcttc ctcgtacacc cacaaatcca gctcggcata tgtctcgggc gaacctaacg    2100
aagccggact caacgcagcc agggcgccac cagaagacga cgttacctca ccagatgcaa    2160
catcttcgag catccgcaag gtttggaagc caccgttgtt agaccaacgt cgtttcatgt    2220
tgataatgca aggtatttca cttcacacat ttatcccttta gaagatcacc atacacaaat    2280
tgaaaatata gtgatttta tttatgactg acataacatc cttaggaata tagtcatctt     2340
attgcagatt ttactcgaaa gcatttctca actcctaatt cataattgaa tctctgtacc    2400
taatgtgtgt gactgtaaaa tctaattgta tcattttgag tatataattt aatgattaaa    2460
atgattataa ttacttttcc tcttagtttc aaaatctttt gtatattaat ttatattcat    2520
agttagaaag tatttatgta aaattttaaa ttttacaaaa caaataaat aataaataa      2580
tatcttaaaa gcataaaata ggtaacttgg atgaatgttt aaaatttgtt attgacatat    2640
gaacataata tgttctattt caatataaaa aaattgttta attatcattt ctgattgata    2700
gagcggcata cgaatcagtt tttaggtagc atgtgtttca tttcacaaat acaattatac    2760
atataattgt taatggttat atataattag tgatatgagc atgtgcgtct tgtatatata    2820
gc                                                                   2822
```

<210> SEQ ID NO 8
<211> LENGTH: 1680
<212> TYPE: DNA
<213> ORGANISM: Ctenocephalides felis
<220> FEATURE:
<221> NAME/KEY: CDS
<222> LOCATION: (1)..(1680)

<400> SEQUENCE: 8

```
atg aaa cga cgt tgg tct aac aac ggt ggc ttc caa acc ttg cgg atg     48
Met Lys Arg Arg Trp Ser Asn Asn Gly Gly Phe Gln Thr Leu Arg Met
1               5                   10                  15
```

```
ctc gaa gat gtt gca tct ggt gag gta acg tcg tct tct ggt ggc gcc      96
Leu Glu Asp Val Ala Ser Gly Glu Val Thr Ser Ser Ser Gly Gly Ala
         20                  25                  30 ctg gct gcg ttg agt ccg gct tcg tta ggt tcg ccc gag aca tat gcc     144
Leu Ala Ala Leu Ser Pro Ala Ser Leu Gly Ser Pro Glu Thr Tyr Ala
     35                  40                  45 gag ctg gat ttg tgg gtg tac gag gaa gct ggc tta cat cca ggt tca     192
Glu Leu Asp Leu Trp Val Tyr Glu Glu Ala Gly Leu His Pro Gly Ser
 50                  55                  60 ggt gtg caa gga tgc ggt gcg gtc gcc gcc ttg cca tcg atc gcg aca     240
Gly Val Gln Gly Cys Gly Ala Val Ala Ala Leu Pro Ser Ile Ala Thr
 65                  70                  75                  80 cag gtc ccc cta gga ttg ccc gct atg gac cta ccc cac acg cct cgg     288
Gln Val Pro Leu Gly Leu Pro Ala Met Asp Leu Pro His Thr Pro Arg
             85                  90                  95 agt gac agt gcg ggt agc atc tca tca gga cga gaa gac ctg tca ccg     336
Ser Asp Ser Ala Gly Ser Ile Ser Ser Gly Arg Glu Asp Leu Ser Pro
            100                 105                 110 cct agt tct ttg aac ggc tat tca gca gat ggc tgc gaa gcg aag aag     384
Pro Ser Ser Leu Asn Gly Tyr Ser Ala Asp Gly Cys Glu Ala Lys Lys
        115                 120                 125 gcc aag aaa ggg ccg gcg ccg cgg cag cag gag gaa cta tgt ctt gtg     432
Ala Lys Lys Gly Pro Ala Pro Arg Gln Gln Glu Glu Leu Cys Leu Val
130                 135                 140 tgc ggc gac cgt gcc tcc gga tat cat tac aac gct ctt act tgt gaa     480
Cys Gly Asp Arg Ala Ser Gly Tyr His Tyr Asn Ala Leu Thr Cys Glu
145                 150                 155                 160 gga tgc aaa ggt ttt ttc cga cga agt gtg act aag aat gcc gtg tac     528
Gly Cys Lys Gly Phe Phe Arg Arg Ser Val Thr Lys Asn Ala Val Tyr
                165                 170                 175 gtg tgc aag ttt ggg cac acg tgc gaa atg gac atg tat atg cga cgc     576
Val Cys Lys Phe Gly His Thr Cys Glu Met Asp Met Tyr Met Arg Arg
            180                 185                 190 aaa tgt cag gaa tgt agg ctc aag aaa tgt ttg gct gtc gga atg cgc     624
Lys Cys Gln Glu Cys Arg Leu Lys Lys Cys Leu Ala Val Gly Met Arg
        195                 200                 205 ccc gag tgc gtg gtt ccc gaa aac caa tgc gcc atg aag cga aag gaa     672
Pro Glu Cys Val Val Pro Glu Asn Gln Cys Ala Met Lys Arg Lys Glu
210                 215                 220 aag aag gca cag aag gaa aag gac atc gga cca ata tca ggt acc gtt     720
Lys Lys Ala Gln Lys Glu Lys Asp Ile Gly Pro Ile Ser Gly Thr Val
225                 230                 235                 240 gga aaa tct gct gct ccc tta gcg aat tct gca tta ctt cag aag cct     768
Gly Lys Ser Ala Ala Pro Leu Ala Asn Ser Ala Leu Leu Gln Lys Pro
                245                 250                 255 gat att ttg cct gcg gtc atg aaa tgc gac cca tta cct cca gaa gca     816
Asp Ile Leu Pro Ala Val Met Lys Cys Asp Pro Leu Pro Pro Glu Ala
            260                 265                 270 act aaa gtg aaa ttt ttg tca gac aag att ctt gct gaa aac aga att     864
Thr Lys Val Lys Phe Leu Ser Asp Lys Ile Leu Ala Glu Asn Arg Ile
        275                 280                 285 cga aat gtt cca cct ttg act gca aat caa gaa tat gtg atc gca aga     912
Arg Asn Val Pro Pro Leu Thr Ala Asn Gln Glu Tyr Val Ile Ala Arg
290                 295                 300 tta gtg tgg tac caa gat gga tat gaa caa cct tct gag gaa gac cta     960
Leu Val Trp Tyr Gln Asp Gly Tyr Glu Gln Pro Ser Glu Glu Asp Leu
305                 310                 315                 320 cga agg ata atg ata agt aca cca gct gaa gat gaa gct ctt gaa ttt    1008
Arg Arg Ile Met Ile Ser Thr Pro Ala Glu Asp Glu Ala Leu Glu Phe
            325                 330                 335
```

-continued

| | | | | | | | | | | | | | | | |
|---|---|---|---|---|---|---|---|---|---|---|---|---|---|---|---|
| cgg | cat | ata | act | gaa | att | acc | ata | ctt | act | gtg | cag | ctt | ata | gtg | gaa | 1056
| Arg | His | Ile | Thr | Glu | Ile | Thr | Ile | Leu | Thr | Val | Gln | Leu | Ile | Val | Glu |
| | | | 340 | | | | 345 | | | | | 350 | | | | ttt gca aag ggt tta cca gct ttt acc aaa ata cca caa gaa gat caa    1104
Phe Ala Lys Gly Leu Pro Ala Phe Thr Lys Ile Pro Gln Glu Asp Gln
            355                 360                 365 ata aca tta tta aag gca tgt tca agt gaa gta atg atg ctg cga atg    1152
Ile Thr Leu Leu Lys Ala Cys Ser Ser Glu Val Met Met Leu Arg Met
        370                 375                 380 gct cgg cgg tac gat gca gtg tcg gat tca atc tta ttc gcg aat aat    1200
Ala Arg Arg Tyr Asp Ala Val Ser Asp Ser Ile Leu Phe Ala Asn Asn
385                 390                 395                 400 cgt tca tat act cgt gac tcc tat aaa atg gct ggt atg gca gat aca    1248
Arg Ser Tyr Thr Arg Asp Ser Tyr Lys Met Ala Gly Met Ala Asp Thr
                405                 410                 415 ata gaa gat cta ttg cat ttt tgt cga cag atg tat act atg act gta    1296
Ile Glu Asp Leu Leu His Phe Cys Arg Gln Met Tyr Thr Met Thr Val
            420                 425                 430 gac aat gtg gag tat gca cta ata aca gca att gtg att ttt tca gat    1344
Asp Asn Val Glu Tyr Ala Leu Ile Thr Ala Ile Val Ile Phe Ser Asp
        435                 440                 445 cga cct gga ttg gaa caa gca gat ctt gtg gaa caa att caa agt tat    1392
Arg Pro Gly Leu Glu Gln Ala Asp Leu Val Glu Gln Ile Gln Ser Tyr
450                 455                 460 tac atc aaa aca tta aag tgc tac att ttg aat cga cat agt ggt gac    1440
Tyr Ile Lys Thr Leu Lys Cys Tyr Ile Leu Asn Arg His Ser Gly Asp
465                 470                 475                 480 cct aag tgt gga ata ttg ttt gcc aaa ctt ctt tct att ctt act gaa    1488
Pro Lys Cys Gly Ile Leu Phe Ala Lys Leu Leu Ser Ile Leu Thr Glu
                485                 490                 495 tta cgc acg tta gga aat caa aac tca gaa atg tgt ttt gca ctg aaa    1536
Leu Arg Thr Leu Gly Asn Gln Asn Ser Glu Met Cys Phe Ala Leu Lys
            500                 505                 510 ttg aag aac aga aaa ctt cct aga ttt tta gaa gaa att tgg gat gtg    1584
Leu Lys Asn Arg Lys Leu Pro Arg Phe Leu Glu Glu Ile Trp Asp Val
        515                 520                 525 aca gat aat gtg cct cct acg ata gac agc atg cat agt gta tcg gag    1632
Thr Asp Asn Val Pro Pro Thr Ile Asp Ser Met His Ser Val Ser Glu
530                 535                 540 aat ttc tat aat aat gaa agt aat ggt acc agt gat tct aca cca atg    1680
Asn Phe Tyr Asn Asn Glu Ser Asn Gly Thr Ser Asp Ser Thr Pro Met
545                 550                 555                 560

<210> SEQ ID NO 9
<211> LENGTH: 560
<212> TYPE: PRT
<213> ORGANISM: Ctenocephalides felis

<400> SEQUENCE: 9

Met Lys Arg Arg Trp Ser Asn Asn Gly Gly Phe Gln Thr Leu Arg Met
1               5                   10                  15

Leu Glu Asp Val Ala Ser Gly Glu Val Thr Ser Ser Ser Gly Gly Ala
            20                  25                  30

Leu Ala Ala Leu Ser Pro Ala Ser Leu Gly Ser Pro Glu Thr Tyr Ala
        35                  40                  45

Glu Leu Asp Leu Trp Val Tyr Glu Glu Ala Gly Leu His Pro Gly Ser
    50                  55                  60

Gly Val Gln Gly Cys Gly Ala Val Ala Ala Leu Pro Ser Ile Ala Thr
65                  70                  75                  80

```
Gln Val Pro Leu Gly Leu Pro Ala Met Asp Leu Pro His Thr Pro Arg
            85                  90                  95

Ser Asp Ser Ala Gly Ser Ile Ser Ser Gly Arg Glu Asp Leu Ser Pro
            100                 105                 110

Pro Ser Ser Leu Asn Gly Tyr Ser Ala Asp Gly Cys Glu Ala Lys Lys
            115                 120                 125

Ala Lys Lys Gly Pro Ala Pro Arg Gln Gln Glu Glu Leu Cys Leu Val
    130                 135                 140

Cys Gly Asp Arg Ala Ser Gly Tyr His Tyr Asn Ala Leu Thr Cys Glu
145                 150                 155                 160

Gly Cys Lys Gly Phe Phe Arg Arg Ser Val Thr Lys Asn Ala Val Tyr
                165                 170                 175

Val Cys Lys Phe Gly His Thr Cys Glu Met Asp Met Tyr Met Arg Arg
                180                 185                 190

Lys Cys Gln Glu Cys Arg Leu Lys Lys Cys Leu Ala Val Gly Met Arg
            195                 200                 205

Pro Glu Cys Val Val Pro Glu Asn Gln Cys Ala Met Lys Arg Lys Glu
    210                 215                 220

Lys Lys Ala Gln Lys Glu Lys Asp Ile Gly Pro Ile Ser Gly Thr Val
225                 230                 235                 240

Gly Lys Ser Ala Ala Pro Leu Ala Asn Ser Ala Leu Leu Gln Lys Pro
                245                 250                 255

Asp Ile Leu Pro Ala Val Met Lys Cys Asp Pro Leu Pro Pro Glu Ala
                260                 265                 270

Thr Lys Val Lys Phe Leu Ser Asp Lys Ile Leu Ala Glu Asn Arg Ile
            275                 280                 285

Arg Asn Val Pro Pro Leu Thr Ala Asn Gln Glu Tyr Val Ile Ala Arg
    290                 295                 300

Leu Val Trp Tyr Gln Asp Gly Tyr Glu Gln Pro Ser Glu Glu Asp Leu
305                 310                 315                 320

Arg Arg Ile Met Ile Ser Thr Pro Ala Glu Asp Glu Ala Leu Glu Phe
                325                 330                 335

Arg His Ile Thr Glu Ile Thr Ile Leu Thr Val Gln Leu Ile Val Glu
                340                 345                 350

Phe Ala Lys Gly Leu Pro Ala Phe Thr Lys Ile Pro Gln Glu Asp Gln
            355                 360                 365

Ile Thr Leu Leu Lys Ala Cys Ser Ser Glu Val Met Met Leu Arg Met
    370                 375                 380

Ala Arg Arg Tyr Asp Ala Val Ser Asp Ser Ile Leu Phe Ala Asn Asn
385                 390                 395                 400

Arg Ser Tyr Thr Arg Asp Ser Tyr Lys Met Ala Gly Met Ala Asp Thr
                405                 410                 415

Ile Glu Asp Leu Leu His Phe Cys Arg Gln Met Tyr Thr Met Thr Val
            420                 425                 430

Asp Asn Val Glu Tyr Ala Leu Ile Thr Ala Ile Val Ile Phe Ser Asp
            435                 440                 445

Arg Pro Gly Leu Glu Gln Ala Asp Leu Val Glu Gln Ile Gln Ser Tyr
    450                 455                 460

Tyr Ile Lys Thr Leu Lys Cys Tyr Ile Leu Asn Arg His Ser Gly Asp
465                 470                 475                 480

Pro Lys Cys Gly Ile Leu Phe Ala Lys Leu Leu Ser Ile Leu Thr Glu
                485                 490                 495
```

```
Leu Arg Thr Leu Gly Asn Gln Asn Ser Glu Met Cys Phe Ala Leu Lys
                500                 505                 510

Leu Lys Asn Arg Lys Leu Pro Arg Phe Leu Glu Glu Ile Trp Asp Val
            515                 520                 525

Thr Asp Asn Val Pro Pro Thr Ile Asp Ser Met His Ser Val Ser Glu
        530                 535                 540

Asn Phe Tyr Asn Asn Glu Ser Asn Gly Thr Ser Asp Ser Thr Pro Met
545                 550                 555                 560

<210> SEQ ID NO 10
<211> LENGTH: 1680
<212> TYPE: DNA
<213> ORGANISM: Ctenocephalides felis

<400> SEQUENCE: 10
cattggtgta gaatcactgg taccattact ttcattatta tagaaattct ccgatacact      60
atgcatgctg tctatcgtag gaggcacatt atctgtcaca tcccaaattt cttctaaaaa     120
tctaggaagt tttctgttct tcaatttcag tgcaaaacac atttctgagt tttgatttcc     180
taacgtgcgt aattcagtaa gaatagaaag aagtttggca acaatattc cacacttagg      240 gtcaccacta tgtcgattca aaatgtagca ctttaatgtt ttgatgtaat aactttgaat     300
ttgttccaca agatctgctt gttccaatcc aggtcgatct gaaaaaatca caattgctgt     360
tattagtgca tactccacat tgtctacagt catagtatac atctgtcgac aaaaatgcaa     420
tagatcttct attgtatctg ccataccagc cattttatag gagtcacgag tatatgaacg     480
attattcgcg aataagattg aatccgacac tgcatcgtac cgccgagcca ttcgcagcat     540
cattacttca cttgaacatg cctttaataa tgttatttga tcttcttgtg gtattttggt     600
aaaagctggt aaacccttg caaattccac tataagctgc acagtaagta tggtaatttc      660
agttatatgc cgaaattcaa gagcttcatc ttcagctggt gtacttatca ttatccttcg     720
taggtcttcc tcagaaggtt gttcatatcc atcttggtac cacactaatc ttgcgatcac     780
atattcttga tttgcagtca aaggtggaac atttcgaatt ctgttttcag caagaatctt     840
gtctgacaaa aatttcactt tagttgcttc tggaggtaat gggtcgcatt tcatgaccgc     900
aggcaaaata tcaggcttct gaagtaatgc agaattcgct aagggagcag cagatttccc    960
aacggtacct gatattggtc cgatgtcctt ttccttctgt gccttctttt cctttcgctt    1020
catggcgcat tggtttttcg gaaccacgca ctcggggcgc attccgacag ccaaacattt    1080
cttgagccta cattcctgac atttgcgtcg catatacatg tccatttcgc acgtgtgccc    1140
aaacttgcac acgtacacgg cattcttagt cacacttcgt cggaaaaaac ctttgcatcc    1200
ttcacaagta agagcgttgt aatgatatcc ggaggcacgg tcgccgcaca aagacatag     1260 ttcctcctgc tgccgcggcg ccggccctt cttggccttc ttcgcttcg agccatctgc     1320 tgaatagccg ttcaaagaac taggcggtga caggtcttct cgtcctgatg agatgctacc    1380
cgcactgtca ctccgaggcg tgtgcggtag gtccatagcg ggcaatccta ggggacctg     1440 tgtcgcgatc gatggcaagg cggcgaccgc accgcatcct tgcacacctg aacctggatg    1500
taagccagct tcctcgtaca cccacaaatc cagctcggca tatgtctcgg gcgaacctaa    1560
cgaagccgga ctcaacgcag ccagggcgcc accagaagac gacgttacct caccagatgc    1620
aacatcttcg agcatccgca aggtttggaa gccaccgttg ttagaccaac gtcgtttcat    1680

<210> SEQ ID NO 11
<211> LENGTH: 666
```

```
<212> TYPE: DNA
<213> ORGANISM: Ctenocephalides felis

<400> SEQUENCE: 11
atttgcatta cggtatattt aaatttaaaa ctccacatgt attgacaaaa aataagtaaa      60
aaaatagttc attgaatata atacggtttc attcgtaatg tttcgagcgg ttacaaatct    120
tgcaaattct tctgatggaa ctgttttgaa cgaagttata catgaagatc ttctgcttaa    180
atgtgaaccc tctactagcg tggacgcatt atctaatgga gctttcggta gcaagcagca    240
gcacaaagtc gaagaatgga agcgatcacc tagtcccagt ttgacgaaca gccatgtgcc    300
acctctcaca ccatcaccag gcccatccag cttaccatat tcgacattgt ctaatggcta    360
ttcttcgcca atgtcgtcag gcagctgcga tccctatagc cctaatggta aaatgggacg    420
agaagacctg tcaccgccta gttctttgaa cggctattca gcagatggct gcgaagcgaa    480
gaaggccaag aaagggccgg cgccgcggca acaggaggaa ctatgtcttg tgtgcggcga    540
ccgtgcctcc ggatatcatt acaacgctct tacttgtgaa ggatgcaaag gttttttccg    600
acgaagtgtg actaagaatg ccgtgtacgt gttcaagttt gggcacacgt gcgaaaatgg    660
acatgt                                                                666

<210> SEQ ID NO 12
<211> LENGTH: 666
<212> TYPE: DNA
<213> ORGANISM: Ctenocephalides felis

<400> SEQUENCE: 12
acatgtccat tttcgcacgt gtgcccaaac ttgaacacgt acacggcatt cttagtcaca      60
cttcgtcgga aaaccctttt gcatccttca caagtaagag cgttgtaatg atatccggag    120
gcacggtcgc cgcacacaag acatagttcc tcctgttgcc gcggcgccgg ccctttcttg    180
gccttcttcg cttcgcagcc atctgctgaa tagccgttca agaactaggc ggtgacagg    240
tcttctcgtc ccattttacc attagggcta tagggatcgc agctgcctga cgacattggc    300
gaagaatagc cattagacaa tgtcgaatat ggtaagctgg atgggcctgg tgatggtgtg    360
agaggtggca catggctgtt cgtcaaactg ggactaggtg atcgcttcca ttcttcgact    420
ttgtgctgct gcttgctacc gaaagctcca ttagataatg cgtccacgct agtagagggt    480
tcacatttaa gcagaagatc ttcatgtata acttcgttca aaacagttcc atcagaagaa    540
tttgcaagat ttgtaaccgc tcgaaacatt acgaatgaaa ccgtattata ttcaatgaac    600
tatttttta cttatttttt gtcaatacat gtggagtttt aaatttaaat ataccgtaat    660
gcaaat                                                                666

<210> SEQ ID NO 13
<211> LENGTH: 4148
<212> TYPE: DNA
<213> ORGANISM: Ctenocephalides felis
<220> FEATURE:
<221> NAME/KEY: CDS
<222> LOCATION: (184)..(1869)

<400> SEQUENCE: 13
taaagggaac aaaagctgga gctccaccgc ggtggcggcc gctctagaac tagtggatcc      60
cccgggctgc aggaattcgg cacgagattt gcattacggt atatttaaat ttaaaactcc    120
acatgtattg acaaaaaata agtaaaaaaa tagttcattg aatataatac ggtttcattc    180
gta atg ttt cga gcg gtt aca aat ctt gca aat tct tct gat gga act    228
```

-continued

| | | | | | | | | | | | | | | | | |
|---|---|---|---|---|---|---|---|---|---|---|---|---|---|---|---|---|
| | Met | Phe | Arg | Ala | Val | Thr | Asn | Leu | Ala | Asn | Ser | Ser | Asp | Gly | Thr | |
| | 1 | | | | 5 | | | | | 10 | | | | | 15 | |

```
gtt ttg aac gaa gtt ata cat gaa gat ctt ctg ctt aaa tgt gaa ccc       276
Val Leu Asn Glu Val Ile His Glu Asp Leu Leu Leu Lys Cys Glu Pro
            20              25                  30 tct act agc gtg gac gca tta tct aat gga gct ttc ggt agc aag cag       324
Ser Thr Ser Val Asp Ala Leu Ser Asn Gly Ala Phe Gly Ser Lys Gln
            35              40                  45 cag cac aaa gtc gaa gaa tgg aag cga tca cct agt ccc agt ttg acg       372
Gln His Lys Val Glu Glu Trp Lys Arg Ser Pro Ser Pro Ser Leu Thr
            50              55                  60 aac agc cat gtg cca cct ctc aca cca tca cca ggc cca tcc agc tta       420
Asn Ser His Val Pro Pro Leu Thr Pro Ser Pro Gly Pro Ser Ser Leu
65              70                  75 cca tat tcg aca ttg tct aat ggc tat tct tcg cca atg tcg tca ggc       468
Pro Tyr Ser Thr Leu Ser Asn Gly Tyr Ser Ser Pro Met Ser Ser Gly
80              85                  90                  95 agc tgc gat ccc tat agc cct aat ggt aaa atg gga cga gaa gac ctg       516
Ser Cys Asp Pro Tyr Ser Pro Asn Gly Lys Met Gly Arg Glu Asp Leu
                100                 105                 110 tca ccg cct agt tct ttg aac ggc tat tca gca gat ggc tgc gaa gcg       564
Ser Pro Pro Ser Ser Leu Asn Gly Tyr Ser Ala Asp Gly Cys Glu Ala
                115                 120                 125 aag aag gcc aag aaa ggg ccg gcg ccg cgg cag cag gag gaa cta tgt       612
Lys Lys Ala Lys Lys Gly Pro Ala Pro Arg Gln Gln Glu Glu Leu Cys
            130                 135                 140 ctt gtg tgc ggc gac cgt gcc tcc gga tat cat tac aac gct ctt act       660
Leu Val Cys Gly Asp Arg Ala Ser Gly Tyr His Tyr Asn Ala Leu Thr
    145                 150                 155 tgt gaa gga tgc aaa ggt ttt ttc cga cga agt gtg act aag aat gcc       708
Cys Glu Gly Cys Lys Gly Phe Phe Arg Arg Ser Val Thr Lys Asn Ala
160                 165                 170                 175 gtg tac gtg tgc aag ttt ggg cac acg tgc gaa atg gac atg tat atg       756
Val Tyr Val Cys Lys Phe Gly His Thr Cys Glu Met Asp Met Tyr Met
                180                 185                 190 cga cgc aaa tgt cag gaa tgt agg ctc aag aaa tgt ttg gct gtc gga       804
Arg Arg Lys Cys Gln Glu Cys Arg Leu Lys Lys Cys Leu Ala Val Gly
            195                 200                 205 atg cgc ccc gag tgc gtg gtt ccc gaa aac caa tgc gcc atg aag cga       852
Met Arg Pro Glu Cys Val Val Pro Glu Asn Gln Cys Ala Met Lys Arg
            210                 215                 220 aag gaa aag aag gca cag aag gaa aag gac atc gga cca ata tca ggt       900
Lys Glu Lys Lys Ala Gln Lys Glu Lys Asp Ile Gly Pro Ile Ser Gly
225                 230                 235 acc gtt gga aaa tct gct gct ccc cta gcg aat tct gca tta ctt cag       948
Thr Val Gly Lys Ser Ala Ala Pro Leu Ala Asn Ser Ala Leu Leu Gln
240                 245                 250                 255 aag cct gat att ttg cct gcg gtc atg aaa tgc gac cca tta cct cca       996
Lys Pro Asp Ile Leu Pro Ala Val Met Lys Cys Asp Pro Leu Pro Pro
            260                 265                 270 gaa gca act aaa gtg aaa ttt ttg tca gac aag att ctt gct gaa aac      1044
Glu Ala Thr Lys Val Lys Phe Leu Ser Asp Lys Ile Leu Ala Glu Asn
            275                 280                 285 aga att cga aat gtt cca cct ttg act gca aat caa gaa tat gtg atc      1092
Arg Ile Arg Asn Val Pro Pro Leu Thr Ala Asn Gln Glu Tyr Val Ile
            290                 295                 300 gca aga tta gtg tgg tac caa gat gga tat gaa caa cct tct gag gaa      1140
Ala Arg Leu Val Trp Tyr Gln Asp Gly Tyr Glu Gln Pro Ser Glu Glu
    305                 310                 315
```

```
gac cta cga agg ata atg ata agt aca cca gct gaa gat gaa gct ctt    1188
Asp Leu Arg Arg Ile Met Ile Ser Thr Pro Ala Glu Asp Glu Ala Leu
320                 325                 330                 335 gaa ttt cgg cat ata act gaa att acc ata ctt act gtg cag ctt ata    1236
Glu Phe Arg His Ile Thr Glu Ile Thr Ile Leu Thr Val Gln Leu Ile
                340                 345                 350 gtg gaa ttt gca aag ggt tta cca gct ttt acc aaa ata cca caa gaa    1284
Val Glu Phe Ala Lys Gly Leu Pro Ala Phe Thr Lys Ile Pro Gln Glu
355                 360                 365 gat caa ata aca tta tta aag gca tgt tca agt gaa gta atg atg ctg    1332
Asp Gln Ile Thr Leu Leu Lys Ala Cys Ser Ser Glu Val Met Met Leu
        370                 375                 380 cga atg gct cgg cgg tac gat gca gtg tcg gat tca atc tta ttc gcg    1380
Arg Met Ala Arg Arg Tyr Asp Ala Val Ser Asp Ser Ile Leu Phe Ala
385                 390                 395 aat aat cgt tca tat act cgt gac tcc tat aaa atg gct ggt atg gca    1428
Asn Asn Arg Ser Tyr Thr Arg Asp Ser Tyr Lys Met Ala Gly Met Ala
400                 405                 410                 415 gat aca ata gaa gat cta ttg cat ttt tgt cga cag atg tat act atg    1476
Asp Thr Ile Glu Asp Leu Leu His Phe Cys Arg Gln Met Tyr Thr Met
                420                 425                 430 act gta gac aat gtg gag tat gca cta ata aca gca att gtg att ttt    1524
Thr Val Asp Asn Val Glu Tyr Ala Leu Ile Thr Ala Ile Val Ile Phe
            435                 440                 445 tca gat cga cct gga ttg gaa caa gca gat ctt gtg gaa caa att caa    1572
Ser Asp Arg Pro Gly Leu Glu Gln Ala Asp Leu Val Glu Gln Ile Gln
        450                 455                 460 agt tat tac atc aaa aca tta aag tgc tac att ttg aat cga cat agt    1620
Ser Tyr Tyr Ile Lys Thr Leu Lys Cys Tyr Ile Leu Asn Arg His Ser
465                 470                 475 ggt gac cct aag tgt gga ata ttg ttt gcc aaa ctt ctt tct att ctt    1668
Gly Asp Pro Lys Cys Gly Ile Leu Phe Ala Lys Leu Leu Ser Ile Leu
480                 485                 490                 495 act gaa tta cgc acg tta gga aat caa aac tca gaa atg tgt ttt gca    1716
Thr Glu Leu Arg Thr Leu Gly Asn Gln Asn Ser Glu Met Cys Phe Ala
                500                 505                 510 ctg aaa ttg aag aac aga aaa ctt cct aga ttt tta gaa gaa att tgg    1764
Leu Lys Leu Lys Asn Arg Lys Leu Pro Arg Phe Leu Glu Glu Ile Trp
            515                 520                 525 gat gtg aca gat aat gtg cct cct acg ata gac agc atg cat agt gta    1812
Asp Val Thr Asp Asn Val Pro Pro Thr Ile Asp Ser Met His Ser Val
        530                 535                 540 tcg gag aat ttc tat aat aat gaa agt aat ggt acc agt gat tct aca    1860
Ser Glu Asn Phe Tyr Asn Asn Glu Ser Asn Gly Thr Ser Asp Ser Thr
545                 550                 555 ccg atg taa agtgctcaga aaatcaacag ctcttttgca tatttgttta            1909
Pro Met
560 ctgtgtactg gtatggaaaa ttaaggtatc attaaaatat tacataagca ccatgggaaa    1969 aggccgttaa ggcaatattt ttgaatatat aatctattga gacgatacca atggtaaact    2029 tggaaaaatc tctgttacat attaagagcc aagttaaaga taatgtgaag gatggtgata    2089 tatgctgtgt acactcaatg gccttattaa aataaggtta cacctcgata ggaaattaaa    2149 aagaaatcat gtgtaataaa atcatttgta ggccggccat actgattac ctatattaag    2209 cagaaacttc ttattgtata aatatatttt tgctttgcaa ggtaaaacct tctcaatgca    2269 acaatgaatt atatataaac attgattatt ttatcgttag aatttgaatt ttgtgttgtg    2329 ggagaattgt atttggatta gataaatagg ctgtgaaaaa taatttaatt ctatatcctc    2389
```

```
aaaatacccta tacattatat tgacctccat ttgaaatcat ctgacaaagg aagctataat    2449
tgctgcaacc ctcacacgag aatacatata taaatactac acatagtgct caagtagcta    2509
taatgatata aattaacata tttccaaaat agattcaagt attttttagcc tcattcattt    2569 tttaccttag aaatttgcaa gttttattca aaattatata aattcattcc gaaaccatac    2629
agtgctcttg tcaaatgctg ctgctgtaac ttgtatatgt ttgtttatgt aattaatgct    2689
tcatataaat ttatgctgtt taagacatta tgtgtaatat attatcaccc tctttattag    2749
ttagaatata tgtattttta taagtttgac gatagaatgt tttaaagtta ttttcagact    2809
ggccctctta tcaaatgatt ttaaataaag ggtttctcaa ttcacatgtg atgattcatc    2869
taacgttaga tcatatttga atgctagttc attaaatatt tgtaaggaaa atgatacaaa    2929
gtatgccatt gtttggtgtt ccaactactt taataatatt tgccaaattc tctctcaaaa    2989
gttaatgatt tttattattt taatcaatta tctactttgt agttcatgta tggcatatca    3049
atataagtat gcgtgtgcta taataatttt gaacgttgca ccataattaa gtgttcaaaa    3109
tatccttgtc aatggtatat atatatatat atatatatat atgtatat atatatat     3169 atgtgatcca attctggggg ggcgcagcat caactaaaaa atgtaaggat ttttgaaaca    3229
tctttatttt cccatacgtt ttgacgtaga attctacgtc atcgtcagtg gttttgggat    3289
tctggattat cacttgcaca tcttaacagc aacttgtgaa taattgacgt ttggtgcttg    3349
tttccaattg ttaattattt gcaagttgtt gttgatatgt gtgagtgata atctaagaat    3409
ttcaaaacca ctgacgatga cgtggaattt tacattgaaa tgtatggaag gatgaagatg    3469
ttttggaaat cgttacttta tttgtatttt ttacttgatg ttgtgccctc taagaaatta    3529
atcatacatt tcaacatcaa atttaaaaca ctttcaacat atatctatat gtacatatat    3589
gtatatatat atatatatat atatatatat atatatatat ataaattta aaatttatta    3649 ataaatggca ctaaagtgta gtactgccta ggatgataaa attaaatttt ttgagacaat    3709
ataaatataa ctgaaaaatt acagttttag atttatttga tagttttata ataatgatgc    3769
aataagtgtt aatagcaagc atacatagaa gagcattgca gcacatattt tcaaatgatt    3829 gatttttttat agttatcaat atcatgtcca taaagttatt taatacctaa cactgtgtta    3889 aagtttttttt ttcgtttatg ttaatgctca gaatatttga aaatgaaact ggttgtgaaa    3949
cacttctaat aattagtttt tcaatttaat ttttctgttt attagttgaa attgaggaac    4009
ccatgatatt gaaatagta tcaatgacta acaaatttta atatctttaa catgatttga    4069
aataaatata tatgtataat gtacatagtt gtgtgagcaa agtaagttca cacacattta    4129
aaaaaaaaaa aaaaaaaaa                                                 4148
```

<210> SEQ ID NO 14
<211> LENGTH: 561
<212> TYPE: PRT
<213> ORGANISM: Ctenocephalides felis

<400> SEQUENCE: 14

```
Met Phe Arg Ala Val Thr Asn Leu Ala Asn Ser Ser Asp Gly Thr Val
1               5                   10                  15

Leu Asn Glu Val Ile His Glu Asp Leu Leu Leu Lys Cys Glu Pro Ser
            20                  25                  30

Thr Ser Val Asp Ala Leu Ser Asn Gly Ala Phe Gly Ser Lys Gln Gln
        35                  40                  45

His Lys Val Glu Glu Trp Lys Arg Ser Pro Ser Pro Ser Leu Thr Asn
```

-continued

```
            50                  55                  60
Ser His Val Pro Pro Leu Thr Pro Ser Pro Gly Pro Ser Ser Leu Pro
65                  70                  75                  80

Tyr Ser Thr Leu Ser Asn Gly Tyr Ser Ser Pro Met Ser Ser Gly Ser
                85                  90                  95

Cys Asp Pro Tyr Ser Pro Asn Gly Lys Met Gly Arg Glu Asp Leu Ser
                100                 105                 110

Pro Pro Ser Ser Leu Asn Gly Tyr Ser Ala Asp Gly Cys Glu Ala Lys
                115                 120                 125

Lys Ala Lys Lys Gly Pro Ala Pro Arg Gln Gln Glu Glu Leu Cys Leu
130                 135                 140

Val Cys Gly Asp Arg Ala Ser Gly Tyr His Tyr Asn Ala Leu Thr Cys
145                 150                 155                 160

Glu Gly Cys Lys Gly Phe Phe Arg Arg Ser Val Thr Lys Asn Ala Val
                165                 170                 175

Tyr Val Cys Lys Phe Gly His Thr Cys Glu Met Asp Met Tyr Met Arg
                180                 185                 190

Arg Lys Cys Gln Glu Cys Arg Leu Lys Cys Leu Ala Val Gly Met
                195                 200                 205

Arg Pro Glu Cys Val Val Pro Glu Asn Gln Cys Ala Met Lys Arg Lys
210                 215                 220

Glu Lys Lys Ala Gln Lys Glu Lys Asp Ile Gly Pro Ile Ser Gly Thr
225                 230                 235                 240

Val Gly Lys Ser Ala Ala Pro Leu Ala Asn Ser Ala Leu Leu Gln Lys
                245                 250                 255

Pro Asp Ile Leu Pro Ala Val Met Lys Cys Asp Pro Leu Pro Pro Glu
                260                 265                 270

Ala Thr Lys Val Lys Phe Leu Ser Asp Lys Ile Leu Ala Glu Asn Arg
                275                 280                 285

Ile Arg Asn Val Pro Pro Leu Thr Ala Asn Gln Glu Tyr Val Ile Ala
                290                 295                 300

Arg Leu Val Trp Tyr Gln Asp Gly Tyr Glu Gln Pro Ser Glu Glu Asp
305                 310                 315                 320

Leu Arg Arg Ile Met Ile Ser Thr Pro Ala Glu Asp Glu Ala Leu Glu
                325                 330                 335

Phe Arg His Ile Thr Glu Ile Thr Ile Leu Thr Val Gln Leu Ile Val
                340                 345                 350

Glu Phe Ala Lys Gly Leu Pro Ala Phe Thr Lys Ile Pro Gln Glu Asp
                355                 360                 365

Gln Ile Thr Leu Leu Lys Ala Cys Ser Ser Glu Val Met Met Leu Arg
                370                 375                 380

Met Ala Arg Arg Tyr Asp Ala Val Ser Asp Ser Ile Leu Phe Ala Asn
385                 390                 395                 400

Asn Arg Ser Tyr Thr Arg Asp Ser Tyr Lys Met Ala Gly Met Ala Asp
                405                 410                 415

Thr Ile Glu Asp Leu Leu His Phe Cys Arg Gln Met Tyr Thr Met Thr
                420                 425                 430

Val Asp Asn Val Glu Tyr Ala Leu Ile Thr Ala Ile Val Ile Phe Ser
                435                 440                 445

Asp Arg Pro Gly Leu Glu Gln Ala Asp Leu Val Glu Gln Ile Gln Ser
                450                 455                 460

Tyr Tyr Ile Lys Thr Leu Lys Cys Tyr Ile Leu Asn Arg His Ser Gly
465                 470                 475                 480
```

```
Asp Pro Lys Cys Gly Ile Leu Phe Ala Lys Leu Leu Ser Ile Leu Thr
            485                 490                 495

Glu Leu Arg Thr Leu Gly Asn Gln Asn Ser Glu Met Cys Phe Ala Leu
            500                 505                 510

Lys Leu Lys Asn Arg Lys Leu Pro Arg Phe Leu Glu Glu Ile Trp Asp
            515                 520                 525

Val Thr Asp Asn Val Pro Pro Thr Ile Asp Ser Met His Ser Val Ser
        530                 535                 540

Glu Asn Phe Tyr Asn Asn Glu Ser Asn Gly Thr Ser Asp Ser Thr Pro
545                 550                 555                 560

Met

<210> SEQ ID NO 15
<211> LENGTH: 4148
<212> TYPE: DNA
<213> ORGANISM: Ctenocephalides felis

<400> SEQUENCE: 15
```

| | | | | | |
|---|---|---|---|---|---|
| ttttttttttt | tttttttttt | aaatgtgtgt | gaacttactt | tgctcacaca | actatgtaca | 60 |
| ttatacatat | atatttattt | caaatcatgt | taaagatatt | aaaatttgtt | agtcattgat | 120 |
| actattttca | atatcatggg | ttcctcaatt | tcaactaata | aacagaaaaa | ttaaattgaa | 180 |
| aaactaatta | ttagaagtgt | tcacaacca | gtttcatttt | caaatattct | gagcattaac | 240 |
| ataaacgaaa | aaaaaacttt | aacacagtgt | taggtattaa | ataactttat | ggacatgata | 300 |
| ttgataacta | taaaaaatca | atcatttgaa | atatgtgct | gcaatgctct | tctatgtatg | 360 |
| cttgctatta | acacttattg | catcattatt | ataaaactat | caaataaatc | taaaactgta | 420 |
| attttttcagt | tatatttata | ttgtctcaaa | aaatttaatt | ttatcatcct | aggcagtact | 480 |
| acactttagt | gccatttatt | aataaatttt | aaattatata | tatatatata | tatatatata | 540 |
| tatatatata | tatatataca | tatatgtaca | tatagatata | tgttgaaagt | gttttaaatt | 600 |
| tgatgttgaa | atgtatgatt | aatttcttag | agggcacaac | atcaagtaaa | aaatacaaat | 660 |
| aaagtaacga | tttccaaaac | atcttcatcc | ttccatacat | ttcaatgtaa | aattccacgt | 720 |
| catcgtcagt | ggttttgaaa | ttcttagatt | atcactcaca | catatcaaca | acaacttgca | 780 |
| aataattaac | aattggaaac | aagcaccaaa | cgtcaattat | tcacaagttg | ctgttaagat | 840 |
| gtgcaagtga | taatccagaa | tcccaaaacc | actgacgatg | acgtagaatt | ctacgtcaaa | 900 |
| acgtatggga | aaataaagat | gttttcaaaaa | tccttacatt | ttttagttga | tgctgcgccc | 960 |
| ccccagaatt | ggatcacata | tatatatata | tatacatata | tatatatata | tatatatata | 1020 |
| tataccattg | acaaggatat | tttgaacact | taattatggt | gcaacgttca | aaattattat | 1080 |
| agcacacgca | tacttatatt | gatatgccat | acatgaacta | caaagtagat | aattgattaa | 1140 |
| aataataaaa | atcattaact | tttgagagag | aatttggcaa | atattattaa | agtagttgga | 1200 |
| acaccaaaca | atggcatact | ttgtatcatt | ttccttacaa | atatttaatg | aactagcatt | 1260 |
| caaatatgat | ctaacgttag | atgaatcatc | acatgtgaat | tgagaaaccc | tttatttaaa | 1320 |
| atcatttgat | aagagggcca | gtctgaaaat | aactttaaaa | cattctatcg | tcaaacttat | 1380 |
| aaaaatacat | atattctaac | taataaaagag | ggtgataata | tattacacat | aatgtcttaa | 1440 |
| acagcataaa | tttatatgaa | gcattaatta | cataaacaaa | catatacaag | ttacagcagc | 1500 |
| agcatttgac | aagagcactg | tatggttttcg | gaatgaattt | ataattttt | gaataaaact | 1560 |
| tgcaaattttc | taaggtaaaa | aatgaatgag | gctaaaaata | cttgaatcta | ttttggaaat | 1620 |

```
atgttaattt atatcattat agctacttga gcactatgtg tagtatttat atatgtattc    1680
tcgtgtgagg gttgcagcaa ttatagcttc ctttgtcaga tgatttcaaa tggaggtcaa    1740
tataatgtat aggtattttg aggatataga attaaattat ttttcacagc ctatttatct    1800
aatccaaata caattctccc acaacacaaa attcaaattc taacgataaa ataatcaatg    1860
tttatatata attcattgtt gcattgagaa ggttttacct tgcaaagcaa aaatatattt    1920
atacaataag aagtttctgc ttaatatagg taaatcagta tggccggcct acaaatgatt    1980
ttattacaca tgatttcttt ttaatttcct atcgaggtgt aaccttattt taataaggcc    2040
attgagtgta cacagcatat atcaccatcc ttcacattat ctttaacttg gctcttaata    2100
tgtaacagag attttccaa gtttaccatt ggtatcgtct caatagatta tatattcaaa    2160
aatattgcct taacggcctt ttcccatggt gcttatgtaa tattttaatg ataccttaat    2220
tttccatacc agtacacagt aaacaaatat gcaaaagagc tgttgatttt ctgagcactt    2280
tacatcggtg tagaatcact ggtaccatta ctttcattat tatagaaatt ctccgataca    2340
ctatgcatgc tgtctatcgt aggaggcaca ttatctgtca catcccaaat tcttctaaa    2400 aatctaggaa gttttctgtt cttcaatttc agtgcaaaac acatttctga gttttgattt    2460
cctaacgtgc gtaattcagt aagaatagaa agaagtttgg caaacaatat tccacactta    2520
gggtcaccac tatgtcgatt caaaatgtag cactttaatg ttttgatgta ataactttga    2580
atttgttcca caagatctgc ttgttccaat ccaggtcgat ctgaaaaaat cacaattgct    2640
gttattagtg catactccac attgtctaca gtcatagtat acatctgtcg acaaaaatgc    2700
aatagatctt ctattgtatc tgccatacca gccattttat aggagtcacg agtatatgaa    2760
cgattattcg cgaataagat tgaatccgac actgcatcgt accgccgagc cattcgcagc    2820
atcattactt cacttgaaca tgcctttaat aatgttattt gatcttcttg tggtattttg    2880
gtaaaagctg gtaaaccctt tgcaaattcc actataagct gcacagtaag tatggtaatt    2940
tcagttatat gccgaaattc aagagcttca tcttcagctg gtgtacttat cattatcctt    3000
cgtaggtctt cctcagaagg ttgttcatat ccatcttggt accacactaa tcttgcgatc    3060
acatattctt gatttgcagt caaaggtgga acatttcgaa ttctgttttc agcaagaatc    3120
ttgtctgaca aaaatttcac tttagttgct tctggaggta atgggtcgca tttcatgacc    3180
gcaggcaaaa tatcaggctt ctgaagtaat gcagaattcg ctaggggagc agcagatttt    3240
ccaacggtac ctgatattgg tccgatgtcc ttttccttct gtgccttctt ttcctttcgc    3300
ttcatggcgc attggttttc gggaaccacg cactcggggc gcattccgac agccaaacat    3360
ttcttgagcc tacattcctg acatttgcgt cgcatataca tgtccatttc gcacgtgtgc    3420
ccaaacttgc acacgtacac ggcattctta gtcacacttc gtcggaaaaa acctttgcat    3480
ccttcacaag taagagcgtt gtaatgatat ccggaggcac ggtcgccgca cacaagacat    3540
agttcctcct gctgccgcgg cgccggccct ttcttggcct tcttcgcttc gcagccatct    3600
gctgaatagc cgttcaaaga actaggcggt gacaggtctt ctcgtcccat tttaccatta    3660
gggctatagg gatcgcagct gcctgacgac attggcgaag aatagccatt agacaatgtc    3720
gaatatggta agctggatgg gcctggtgat ggtgtgagag gtggcacatg gctgttcgtc    3780
aaactgggac taggtgatcg cttccattct tcgactttgt gctgctgctt gctaccgaaa    3840
gctccattag ataatgcgtc cacgctagta gagggttcac atttaagcag aagatcttca    3900
tgtataactt cgttcaaaac agttccatca gaagaatttg caagatttgt aaccgctcga    3960
```

```
aacattacga atgaaaccgt attatattca atgaactatt tttttactta tttttttgtca    4020 atacatgtgg agttttaaat ttaaatatac cgtaatgcaa atctcgtgcc gaattcctgc    4080
agcccggggg atccactagt tctagagcgg ccgccaccgc ggtggagctc cagcttttgt    4140
tcccttta                                                            4148

<210> SEQ ID NO 16
<211> LENGTH: 1683
<212> TYPE: DNA
<213> ORGANISM: Ctenocephalides felis
<220> FEATURE:
<221> NAME/KEY: CDS
<222> LOCATION: (1)..(1683)

<400> SEQUENCE: 16 atg ttt cga gcg gtt aca aat ctt gca aat tct tct gat gga act gtt         48
Met Phe Arg Ala Val Thr Asn Leu Ala Asn Ser Ser Asp Gly Thr Val
1               5                   10                  15 ttg aac gaa gtt ata cat gaa gat ctt ctg ctt aaa tgt gaa ccc tct         96
Leu Asn Glu Val Ile His Glu Asp Leu Leu Leu Lys Cys Glu Pro Ser
            20                  25                  30 act agc gtg gac gca tta tct aat gga gct ttc ggt agc aag cag cag        144
Thr Ser Val Asp Ala Leu Ser Asn Gly Ala Phe Gly Ser Lys Gln Gln
        35                  40                  45 cac aaa gtc gaa gaa tgg aag cga tca cct agt ccc agt ttg acg aac        192
His Lys Val Glu Glu Trp Lys Arg Ser Pro Ser Pro Ser Leu Thr Asn
    50                  55                  60 agc cat gtg cca cct ctc aca cca tca cca ggc cca tcc agc tta cca        240
Ser His Val Pro Pro Leu Thr Pro Ser Pro Gly Pro Ser Ser Leu Pro
65                  70                  75                  80 tat tcg aca ttg tct aat ggc tat tct tcg cca atg tcg tca ggc agc        288
Tyr Ser Thr Leu Ser Asn Gly Tyr Ser Ser Pro Met Ser Ser Gly Ser
                85                  90                  95 tgc gat ccc tat agc cct aat ggt aaa atg gga cga gaa gac ctg tca        336
Cys Asp Pro Tyr Ser Pro Asn Gly Lys Met Gly Arg Glu Asp Leu Ser
            100                 105                 110 ccg cct agt tct ttg aac ggc tat tca gca gat ggc tgc gaa gcg aag        384
Pro Pro Ser Ser Leu Asn Gly Tyr Ser Ala Asp Gly Cys Glu Ala Lys
        115                 120                 125 aag gcc aag aaa ggg ccg gcg ccg cgg cag cag gag gaa cta tgt ctt        432
Lys Ala Lys Lys Gly Pro Ala Pro Arg Gln Gln Glu Glu Leu Cys Leu
    130                 135                 140 gtg tgc ggc gac cgt gcc tcc gga tat cat tac aac gct ctt act tgt        480
Val Cys Gly Asp Arg Ala Ser Gly Tyr His Tyr Asn Ala Leu Thr Cys
145                 150                 155                 160 gaa gga tgc aaa ggt ttt ttc cga cga agt gtg act aag aat gcc gtg        528
Glu Gly Cys Lys Gly Phe Phe Arg Arg Ser Val Thr Lys Asn Ala Val
                165                 170                 175 tac gtg tgc aag ttt ggg cac acg tgc gaa atg gac atg tat atg cga        576
Tyr Val Cys Lys Phe Gly His Thr Cys Glu Met Asp Met Tyr Met Arg
            180                 185                 190 cgc aaa tgt cag gaa tgt agg ctc aag aaa tgt ttg gct gtc gga atg        624
Arg Lys Cys Gln Glu Cys Arg Leu Lys Lys Cys Leu Ala Val Gly Met
        195                 200                 205 cgc ccc gag tgc gtg gtt ccc gaa aac caa tgc gcc atg aag cga aag        672
Arg Pro Glu Cys Val Val Pro Glu Asn Gln Cys Ala Met Lys Arg Lys
    210                 215                 220 gaa aag aag gca cag aag gaa aag gac atc gga cca ata tca ggt acc        720
Glu Lys Lys Ala Gln Lys Glu Lys Asp Ile Gly Pro Ile Ser Gly Thr
225                 230                 235                 240
```

| | | |
|---|---|---|
| gtt gga aaa tct gct gct ccc cta gcg aat tct gca tta ctt cag aag<br>Val Gly Lys Ser Ala Ala Pro Leu Ala Asn Ser Ala Leu Leu Gln Lys<br>                          245                        250                        255 | 768 |
| cct gat att ttg cct gcg gtc atg aaa tgc gac cca tta cct cca gaa<br>Pro Asp Ile Leu Pro Ala Val Met Lys Cys Asp Pro Leu Pro Pro Glu<br>                    260                        265                        270 | 816 |
| gca act aaa gtg aaa ttt ttg tca gac aag att ctt gct gaa aac aga<br>Ala Thr Lys Val Lys Phe Leu Ser Asp Lys Ile Leu Ala Glu Asn Arg<br>                        275                        280                        285 | 864 |
| att cga aat gtt cca cct ttg act gca aat caa gaa tat gtg atc gca<br>Ile Arg Asn Val Pro Pro Leu Thr Ala Asn Gln Glu Tyr Val Ile Ala<br>290                        295                        300 | 912 |
| aga tta gtg tgg tac caa gat gga tat gaa caa cct tct gag gaa gac<br>Arg Leu Val Trp Tyr Gln Asp Gly Tyr Glu Gln Pro Ser Glu Glu Asp<br>305                        310                        315                        320 | 960 |
| cta cga agg ata atg ata agt aca cca gct gaa gat gaa gct ctt gaa<br>Leu Arg Arg Ile Met Ile Ser Thr Pro Ala Glu Asp Glu Ala Leu Glu<br>                        325                        330                        335 | 1008 |
| ttt cgg cat ata act gaa att acc ata ctt act gtg cag ctt ata gtg<br>Phe Arg His Ile Thr Glu Ile Thr Ile Leu Thr Val Gln Leu Ile Val<br>                        340                        345                        350 | 1056 |
| gaa ttt gca aag ggt tta cca gct ttt acc aaa ata cca caa gaa gat<br>Glu Phe Ala Lys Gly Leu Pro Ala Phe Thr Lys Ile Pro Gln Glu Asp<br>                    355                        360                        365 | 1104 |
| caa ata aca tta tta aag gca tgt tca agt gaa gta atg atg ctg cga<br>Gln Ile Thr Leu Leu Lys Ala Cys Ser Ser Glu Val Met Met Leu Arg<br>370                        375                        380 | 1152 |
| atg gct cgg cgg tac gat gca gtg tcg gat tca atc tta ttc gcg aat<br>Met Ala Arg Arg Tyr Asp Ala Val Ser Asp Ser Ile Leu Phe Ala Asn<br>385                        390                        395                        400 | 1200 |
| aat cgt tca tat act cgt gac tcc tat aaa atg gct ggt atg gca gat<br>Asn Arg Ser Tyr Thr Arg Asp Ser Tyr Lys Met Ala Gly Met Ala Asp<br>                        405                        410                        415 | 1248 |
| aca ata gaa gat cta ttg cat ttt tgt cga cag atg tat act atg act<br>Thr Ile Glu Asp Leu Leu His Phe Cys Arg Gln Met Tyr Thr Met Thr<br>                    420                        425                        430 | 1296 |
| gta gac aat gtg gag tat gca cta ata aca gca att gtg att ttt tca<br>Val Asp Asn Val Glu Tyr Ala Leu Ile Thr Ala Ile Val Ile Phe Ser<br>                        435                        440                        445 | 1344 |
| gat cga cct gga ttg gaa caa gca gat ctt gtg gaa caa att caa agt<br>Asp Arg Pro Gly Leu Glu Gln Ala Asp Leu Val Glu Gln Ile Gln Ser<br>                    450                        455                        460 | 1392 |
| tat tac atc aaa aca tta aag tgc tac att tTg aat cga cat agt ggt<br>Tyr Tyr Ile Lys Thr Leu Lys Cys Tyr Ile Leu Asn Arg His Ser Gly<br>465                        470                        475                        480 | 1440 |
| gac cct aag tgt gga ata ttg ttt gcc aaa ctt ctt tct att ctt act<br>Asp Pro Lys Cys Gly Ile Leu Phe Ala Lys Leu Leu Ser Ile Leu Thr<br>                        485                        490                        495 | 1488 |
| gaa tta cgc acg tta gga aat caa aac tca gaa atg tgt ttt gca ctg<br>Glu Leu Arg Thr Leu Gly Asn Gln Asn Ser Glu Met Cys Phe Ala Leu<br>                    500                        505                        510 | 1536 |
| aaa ttg aag aac aga aaa ctt cct aga ttt tta gaa gaa att tgg gat<br>Lys Leu Lys Asn Arg Lys Leu Pro Arg Phe Leu Glu Glu Ile Trp Asp<br>                        515                        520                        525 | 1584 |
| gtg aca gat aat gtg cct cct acg ata gac agc atg cat agt gta tcg<br>Val Thr Asp Asn Val Pro Pro Thr Ile Asp Ser Met His Ser Val Ser<br>530                        535                        540 | 1632 |
| gag aat ttc tat aat aat gaa agt aat ggt acc agt gat tct aca ccg<br>Glu Asn Phe Tyr Asn Asn Glu Ser Asn Gly Thr Ser Asp Ser Thr Pro<br>545                        550                        555                        560 | 1680 |

```
atg                                                              1683
Met
```

<210> SEQ ID NO 17
<211> LENGTH: 561
<212> TYPE: PRT
<213> ORGANISM: Ctenocephalides felis

<400> SEQUENCE: 17

```
Met Phe Arg Ala Val Thr Asn Leu Ala Asn Ser Ser Asp Gly Thr Val
1               5                   10                  15

Leu Asn Glu Val Ile His Glu Asp Leu Leu Lys Cys Glu Pro Ser
            20                  25                  30

Thr Ser Val Asp Ala Leu Ser Asn Gly Ala Phe Gly Ser Lys Gln Gln
        35                  40                  45

His Lys Val Glu Glu Trp Lys Arg Ser Pro Ser Pro Ser Leu Thr Asn
    50                  55                  60

Ser His Val Pro Pro Leu Thr Pro Ser Pro Gly Pro Ser Ser Leu Pro
65                  70                  75                  80

Tyr Ser Thr Leu Ser Asn Gly Tyr Ser Ser Pro Met Ser Ser Gly Ser
                85                  90                  95

Cys Asp Pro Tyr Ser Pro Asn Gly Lys Met Gly Arg Glu Asp Leu Ser
            100                 105                 110

Pro Pro Ser Ser Leu Asn Gly Tyr Ser Ala Asp Gly Cys Glu Ala Lys
        115                 120                 125

Lys Ala Lys Lys Gly Pro Ala Pro Arg Gln Gln Glu Glu Leu Cys Leu
    130                 135                 140

Val Cys Gly Asp Arg Ala Ser Gly Tyr His Tyr Asn Ala Leu Thr Cys
145                 150                 155                 160

Glu Gly Cys Lys Gly Phe Phe Arg Arg Ser Val Thr Lys Asn Ala Val
                165                 170                 175

Tyr Val Cys Lys Phe Gly His Thr Cys Glu Met Asp Met Tyr Met Arg
            180                 185                 190

Arg Lys Cys Gln Glu Cys Arg Leu Lys Lys Cys Leu Ala Val Gly Met
        195                 200                 205

Arg Pro Glu Cys Val Val Pro Glu Asn Gln Cys Ala Met Lys Arg Lys
    210                 215                 220

Glu Lys Lys Ala Gln Lys Glu Lys Asp Ile Gly Pro Ile Ser Gly Thr
225                 230                 235                 240

Val Gly Lys Ser Ala Ala Pro Leu Ala Asn Ser Ala Leu Leu Gln Lys
                245                 250                 255

Pro Asp Ile Leu Pro Ala Val Met Lys Cys Asp Pro Leu Pro Pro Glu
            260                 265                 270

Ala Thr Lys Val Lys Phe Leu Ser Asp Lys Ile Leu Ala Glu Asn Arg
        275                 280                 285

Ile Arg Asn Val Pro Pro Leu Thr Ala Asn Gln Glu Tyr Val Ile Ala
    290                 295                 300

Arg Leu Val Trp Tyr Gln Asp Gly Tyr Glu Gln Pro Ser Glu Glu Asp
305                 310                 315                 320

Leu Arg Arg Ile Met Ile Ser Thr Pro Ala Glu Asp Glu Ala Leu Glu
                325                 330                 335

Phe Arg His Ile Thr Glu Ile Thr Ile Leu Thr Val Gln Leu Ile Val
            340                 345                 350

Glu Phe Ala Lys Gly Leu Pro Ala Phe Thr Lys Ile Pro Gln Glu Asp
```

-continued

```
                355                 360                 365
Gln Ile Thr Leu Leu Lys Ala Cys Ser Ser Glu Val Met Met Leu Arg
    370                 375                 380

Met Ala Arg Arg Tyr Asp Ala Val Ser Asp Ser Ile Leu Phe Ala Asn
385                 390                 395                 400

Asn Arg Ser Tyr Thr Arg Asp Ser Tyr Lys Met Ala Gly Met Ala Asp
                405                 410                 415

Thr Ile Glu Asp Leu Leu His Phe Cys Arg Gln Met Tyr Thr Met Thr
            420                 425                 430

Val Asp Asn Val Glu Tyr Ala Leu Ile Thr Ala Ile Val Ile Phe Ser
        435                 440                 445

Asp Arg Pro Gly Leu Glu Gln Ala Asp Leu Val Glu Gln Ile Gln Ser
    450                 455                 460

Tyr Tyr Ile Lys Thr Leu Lys Cys Tyr Ile Leu Asn Arg His Ser Gly
465                 470                 475                 480

Asp Pro Lys Cys Gly Ile Leu Phe Ala Lys Leu Leu Ser Ile Leu Thr
                485                 490                 495

Glu Leu Arg Thr Leu Gly Asn Gln Asn Ser Glu Met Cys Phe Ala Leu
            500                 505                 510

Lys Leu Lys Asn Arg Lys Leu Pro Arg Phe Leu Glu Glu Ile Trp Asp
        515                 520                 525

Val Thr Asp Asn Val Pro Pro Thr Ile Asp Ser Met His Ser Val Ser
    530                 535                 540

Glu Asn Phe Tyr Asn Asn Glu Ser Asn Gly Thr Ser Asp Ser Thr Pro
545                 550                 555                 560

Met
```

<210> SEQ ID NO 18
<211> LENGTH: 1683
<212> TYPE: DNA
<213> ORGANISM: Ctenocephalides felis

<400> SEQUENCE: 18

| | | | | | |
|---|---|---|---|---|---|
| catcggtgta | gaatcactgg | taccattact | ttcattatta | tagaaattct | ccgatacact | 60 |
| atgcatgctg | tctatcgtag | gaggcacatt | atctgtcaca | tcccaaattt | cttctaaaaa | 120 |
| tctaggaagt | tttctgttct | tcaatttcag | tgcaaaacac | atttctgagt | tttgatttcc | 180 |
| taacgtgcgt | aattcagtaa | gaatagaaag | aagtttggca | aacaatattc | cacacttagg | 240 |
| gtcaccacta | tgtcgattca | aaatgtagca | ctttaatgtt | ttgatgtaat | aactttgaat | 300 |
| ttgttccaca | agatctgctt | gttccaatcc | aggtcgatct | gaaaaaatca | caattgctgt | 360 |
| tattagtgca | tactccacat | tgtctacagt | catagtatac | atctgtcgac | aaaaatgcaa | 420 |
| tagatcttct | attgtatctg | ccataccagc | cattttatag | gagtcacgag | tatatgaacg | 480 |
| attattcgcg | aataagattg | aatccgacac | tgcatcgtac | cgccgagcca | ttcgcagcat | 540 |
| cattacttca | cttgaacatg | cctttaataa | tgttatttga | tcttcttgtg | gtattttggt | 600 |
| aaaagctggt | aaacccttttg | caaattccac | tataagctgc | acagtaagta | tggtaatttc | 660 |
| agttatatgc | cgaaattcaa | gagcttcatc | ttcagctggt | gtacttatca | ttatccttcg | 720 |
| taggtcttcc | tcagaaggtt | gttcatatcc | atcttggtac | cacactaatc | ttgcgatcac | 780 |
| atattcttga | tttgcagtca | aaggtggaac | atttcgaatt | ctgttttcag | caagaatctt | 840 |
| gtctgacaaa | aatttcactt | tagttgcttc | tggaggtaat | gggtcgcatt | tcatgaccgc | 900 |
| aggcaaaata | tcaggcttct | gaagtaatgc | agaattcgct | aggggagcag | cagattttcc | 960 |

-continued

| | |
|---|---|
| aacggtacct gatattggtc cgatgtcctt ttccttctgt gccttctttt cctttcgctt | 1020 |
| catggcgcat tggttttcgg gaaccacgca ctcgggcgc attccgacag ccaaacattt | 1080 |
| cttgagccta cattcctgac atttgcgtcg catatacatg tccatttcgc acgtgtgccc | 1140 |
| aaacttgcac acgtacacgg cattcttagt cacacttcgt cggaaaaaac ctttgcatcc | 1200 |
| ttcacaagta agagcgttgt aatgatatcc ggaggcacgg tcgccgcaca aagacatag | 1260 |
| ttcctcctgc tgccgcggcg ccggccctt cttggccttc ttcgcttcgc agccatctgc | 1320 |
| tgaatagccg ttcaaagaac taggcggtga caggtcttct cgtcccattt taccattagg | 1380 |
| gctataggga tcgcagctgc ctgacgacat tggcgaagaa tagccattag acaatgtcga | 1440 |
| atatggtaag ctggatgggc ctggtgatgg tgtgagaggt ggcacatggc tgttcgtcaa | 1500 |
| actgggacta ggtgatcgct tccattcttc gactttgtgc tgctgcttgc taccgaaagc | 1560 |
| tccattagat aatgcgtcca cgctagtaga gggttcacat ttaagcagaa gatcttcatg | 1620 |
| tataacttcg ttcaaaacag ttccatcaga agaatttgca agatttgtaa ccgctcgaaa | 1680 |
| cat | 1683 |

<210> SEQ ID NO 19
<211> LENGTH: 160
<212> TYPE: DNA
<213> ORGANISM: Ctenocephalides felis

<400> SEQUENCE: 19

| | |
|---|---|
| cagttgcgaa ggttgtaagg gatttttcaa acggacggta cgaaaagatc tgacgtatgc | 60 |
| ctgtcgagag gatagaaatt gtttgatcga caaaaggcag agaaatcgat gtcagttctg | 120 |
| tcgatatcag aaatgtctcg cctgtggaat gaaacgagaa | 160 |

<210> SEQ ID NO 20
<211> LENGTH: 160
<212> TYPE: DNA
<213> ORGANISM: Ctenocephalides felis

<400> SEQUENCE: 20

| | |
|---|---|
| ttctcgtttc attccacagg cgagacattt ctgatatcga cagaactgac atcgatttct | 60 |
| ctgccttttg tcgatcaaac aatttctatc ctctcgacag gcatacgtca gatcttttcg | 120 |
| taccgtccgt ttgaaaaatc ccttacaacc ttcgcaactg | 160 |

<210> SEQ ID NO 21
<211> LENGTH: 2149
<212> TYPE: DNA
<213> ORGANISM: Ctenocephalides felis

<400> SEQUENCE: 21

| | |
|---|---|
| ccgcggcgat agcatcgaaa cgcgtcgcat ggaacgcatt tgtaattgtt ttctgcataa | 60 |
| aatgcctaaa gtcgcggaca gtcaagtgat tgaagtgatg gtatgcgcgc gactcggttt | 120 |
| gttttgacgt gttcgaagat gaacgatatt ttaaatattt tgtgtttagt tttagtctcg | 180 |
| agataatttt tgtgctgtgt gataagagtt gtgctttcat aaaaaggaat tgtttattag | 240 |
| attttgaatg acagtgcccc atgtgggaga tgacatactg aacgcattag tttatatgtt | 300 |
| gcttataatt gagtatagga ataaactgtt aatttcaatt ttttggtaac tccaaatgtt | 360 |
| acctcaaaaa cttaaagtaa gggtcaaata taaaaaaaag tgtcattaag aaattcaaca | 420 |
| tgactagtac acatatcagt gagtgagttt atattagaaa tgaaggagac gcataaattg | 480 |

```
gtaacttaat taagcattac aatcaactgg gaataaataa atatatcttc taaaatgatg    540
aaaaaagaga agcctatgat gtctgtgacg gctttgattc aaggagccgc tcagaatcaa    600
atatggggac gaggattatc tggccttaca ggcttggccc tcgaccaagg gctgtcaatg    660
agctcgatgg gaccgctctc accgccggat atgaaaccgg atcctgcgct actgaacggc    720
ggcttttcgc ccggcagtgg cggcgcagtt gtcggcagtc ccgctagtcc gccttttggt    780
caaaatcaca caatagtatc aggaaacacg gccacgggcg cccaaacgaa atcaccatac    840
cctccaaatc atcctttgag cgggtcaaaa catctgtgct ccatatgcgg agatagggct    900
tccgggaagc attatggtgt ttacagttgc gaaggttgta agggattttt caaacggacg    960
gtacgaaaag atctgacgta tgcctgtcga gaggatagaa attgtttgat cgacaaaagg   1020
cagagaaatc gatgtcagtt ctgtcgatat cagaaatgtc tcgcctgtgg aatgaaacga   1080
gaagccgtgc aggaagaacg acaacgagga gcaagaata atgaagaaag caacccgaca   1140
agttctgttc gtgatttaac ggtagaaaga attttagaag cagaacaaag gagtgaaact   1200
cgaaatgttg cgacggaccc ggaattgtcg atacaatatt tgcgagtagg accttcatcc   1260
atggtgcctc ctagatacaa gggccctgta tccagtctgt gtcagcaagc aaataaacag   1320
ttatatcagt tagtacaata cgcaaggtgc atgccgcatt ttagtgcttt acaattagag   1380
gatcaagtaa cgttactcag agcagcctgg aatgaattac ttatagcatc tatagcctgg   1440
agaagtattg agtatctaga atccgatgca gaaacaagta cgtccagtat gtctagtgat   1500
acttcaacaa ggagacgcgc tccaccagga ccgcctgaat taatgtgttt ctttcctggt   1560
atgacgttac atcggaatag tgcaatccag gctggcgtcg gacctatttt cgatcgggta   1620
ctgtcagaat taagtgtcaa aatgagaaga atggatttgg acagagcaga attaggctgt   1680
ttgaaggcta taatactgtt taatcctggt aaatgatgta aaaatataac aaaagtttct   1740
gaaatttatt gtaatgcttg atttaaaaaa aatgctaact tgaatgttag cgcagtcttg   1800
tctacggtag tatgacttaa tttaatatat gtaatttaga aacttgaaga acacttgaaa   1860
ttttgacgat ggcttggggc acctaggact aagtgaaatg ttgcaaatat tgttttacaa   1920
ttgttttcaa attgttattg ttttttaaatt ttgctttcat aatgttgatg tattgaatta   1980
gtctgtgaat cacgttaaaa gcttccaact ctttatata ttgaataagt aatctattca   2040
aagcaattat atatcaaata tattaatgca ttttttattat ttaacatttg tgttcataat   2100
tatttaatat agttattaat ttagattaaa aaaaaaaaa aaaaaaaa                 2149

<210> SEQ ID NO 22
<211> LENGTH: 2149
<212> TYPE: DNA
<213> ORGANISM: Ctenocephalides felis

<400> SEQUENCE: 22 ttttttttt ttttttttt ttaatctaaa ttaataacta tattaaataa ttatgaacac     60
aaatgttaaa taataaaaat gcattaatat atttgatata taattgcttt gaatagatta   120
cttattcaat atataaaga gttggaagct tttaacgtga ttcacagact aattcaatac    180
atcaacatta tgaaagcaaa atttaaaaac aataacaatt tgaaaacaat tgtaaaacaa   240
tatttgcaac atttcactta gtcctaggtg ccccaagcca tcgtcaaaat ttcaagtgtt   300
cttcaagttt ctaaattaca tatattaaat taagtcatac taccgtagac aagactgcgc   360
taacattcaa gttagcattt ttttaaatc aagcattaca ataaatttca gaaacttttg   420
ttatattttt acatcattta ccaggattaa acagtattat agccttcaaa cagcctaatt   480
```

| | |
|---|---:|
| ctgctctgtc caaatccatt cttctcattt tgacacttaa ttctgacagt acccgatcga | 540 |
| aaataggtcc gacgccagcc tggattgcac tattccgatg taacgtcata ccaggaaaga | 600 |
| aacacattaa ttcaggcggt cctggtggag cgcgtctcct tgttgaagta tcactagaca | 660 |
| tactggacgt acttgtttct gcatcggatt ctagatactc aatacttctc caggctatag | 720 |
| atgctataag taattcattc caggctgctc tgagtaacgt tacttgatcc tctaattgta | 780 |
| aagcactaaa atgcggcatg caccttgcgt attgtactaa ctgatataac tgtttatttg | 840 |
| cttgctgaca cagactggat acagggccct tgtatctagg aggcaccatg gatgaaggtc | 900 |
| ctactcgcaa atattgtatc gacaattccg ggtccgtcgc aacatttcga gtttcactcc | 960 |
| tttgttctgc ttctaaaatt cttctaccg ttaaatcacg aacagaactt gtcgggttgc | 1020 |
| tttcttcatt attctttgct cctcgttgtc gttcttcctg cacggcttct cgtttcattc | 1080 |
| cacaggcgag acatttctga tatcgacaga actgacatcg atttctctgc cttttgtcga | 1140 |
| tcaaacaatt tctatcctct cgacaggcat acgtcagatc ttttcgtacc gtccgtttga | 1200 |
| aaaatccctt acaaccttcg caactgtaaa caccataatg cttcccggaa gcccatctc | 1260 |
| cgcatatgga gcacagatgt tttgacccgc tcaaggatg atttggaggg tatggtgatt | 1320 |
| tcgtttgggc gcccgtggcc gtgtttcctg tactattgt gtgattttga ccaaaaggcg | 1380 |
| gactagcggg actgccgaca actgcgccgc cactgccggg cgaaaagccg ccgttcagta | 1440 |
| gcgcaggatc cggtttcata tccggcggtg agagcggtcc catcgagctc attgacagcc | 1500 |
| cttggtcgag ggccaagcct gtaaggccag ataatcctcg tccccatatt tgattctgag | 1560 |
| cggctccttg aatcaaagcc gtcacagaca tcataggctt ctctttttc atcattttag | 1620 |
| aagatatatt tatttattcc cagttgattg taatgcttaa ttaagttacc aatttatgcg | 1680 |
| tctccttcat ttctaatata aactcactca ctgatatgtg tactagtcat gttgaatttc | 1740 |
| ttaatgcacac ttttttttat atttgaccct tactttaagt ttttgaggta acatttggag | 1800 |
| ttaccaaaaa attgaaatta acagtttatt cctatactca attataagca acatataaac | 1860 |
| taatgcgttc agtatgtcat ctcccacatg gggcactgtc attcaaaatc taataaacaa | 1920 |
| ttcctttta tgaaagcaca actcttatca cacagcacaa aaattatctc gagactaaaa | 1980 |
| ctaaacacaa aatatttaaa atatcgttca tcttcgaaca cgtcaaaaca aaccgagtcg | 2040 |
| cgcgcatacc atcacttcaa tcacttgact gtccgcgact ttaggcattt tatgcagaaa | 2100 |
| acaattacaa atgcgttcca tgcgacgcgt ttcgatgcta tcgccgcgg | 2149 |

```
<210> SEQ ID NO 23
<211> LENGTH: 1421
<212> TYPE: DNA
<213> ORGANISM: Ctenocephalides felis

<400> SEQUENCE: 23
```

| | |
|---|---:|
| gcggcacgag ggagataggg cttccgggaa gcattatggt gtttacagtt gcgaaggttg | 60 |
| taagggattt ttcaaacgga cggtacgaaa agatctgacg tatgcctgtc gaggagatag | 120 |
| aaattgtttg atcgacaaaa ggcagagaaa tcgatgtcag ttctgtcgat atcagaaatg | 180 |
| tctcgcctgt ggaatgaaac gagaagccgt gcaggaagaa cgacaacgag gagcaaagaa | 240 |
| taatgaagaa agcaacccga caagttctgt tcgtgattta acggtagaaa gaattttaga | 300 |
| agcagaacaa aggagtgaaa ctcgaaatgt tgcgacggac ccggaattgt cgatacaata | 360 |
| tttgcgagta ggaccttcat ccatggtgcc tcctagatac aagggccctg tatccagtct | 420 |

| | |
|---|---|
| gtgtcagcaa gcaaataaac agttatatca gttagtacaa tacgcaaggt gcatgccgca | 480 |
| ttttagtgct ttacaattag aggatcaagt aacgttactc agagcagcct ggaatgaatt | 540 |
| acttatagca tctatagcct ggagaagtat tgagtatcta gaatccgatg cagaaacaag | 600 |
| tacgtccagt atgtctagtg atacttcaac aaggagacgc gctccaccag gaccgcctga | 660 |
| attaatgtgt ttctttcctg gtatgacgtt acatcggaat agtgcaatcc aggctggcgt | 720 |
| cggacctatt ttcgatcggg tactgtcaga attaagtgtc aaaatgagaa gaatggattt | 780 |
| ggacagagca gaattaggct gtttgaaggc tataatactg tttaatcctg atattcgagg | 840 |
| actgaaatgt agacaggaag tggatgcttt acgagaaaag gtttacgcgt gcctggacga | 900 |
| gcattgcagg acgcagcatc cagcggaaga gggtcgtttc gcagccctgc tgcttcgcct | 960 |
| gccagctctg aggtcaatct ctttgaaatg tctcgatcac ctgttttttct tcagattgat | 1020 |
| tggcgatacg ccgcttgaga gttttcttgt ggatttactc gaggccggac ccatcggttg | 1080 |
| agccgattca tggataaaag ataagtttta tgtattaaga tgagaataag taaatattct | 1140 |
| gcaaagttat ttttctgca cgaatatttc tacaagcacg cacttgggat attgattgtc | 1200 |
| tcttgtgatc ttttgaggtg gcggggagga tacgaaccag tgatatttta aaatattttt | 1260 |
| aattattaga gattaggata gcggtataag tactgtaatg catatataca tatatgcttt | 1320 |
| tgatttatat tagaagtttt tctgcatcat ccagtgaatt aaaataagat ataataagga | 1380 |
| aaagtccata tataaaaaaa aaaaaaaaaa aaaaaaaaa a | 1421 |

<210> SEQ ID NO 24
<211> LENGTH: 1421
<212> TYPE: DNA
<213> ORGANISM: Ctenocephalides felis

<400> SEQUENCE: 24

| | |
|---|---|
| tttttttttt tttttttttt ttttttttat atatggactt ttccttatta tatcttattt | 60 |
| taattcactg gatgatgcag aaaaacttct aatataaatc aaaagcatat atgtatatat | 120 |
| gcattacagt acttataccg ctatcctaat ctctaataat taaaaatatt ttaaaatatc | 180 |
| actggttcgt atcctccccg ccacctcaaa agatcacaag agacaatcaa tatcccaagt | 240 |
| gcgtgcttgt agaaatattc gtgcagaaaa aataactttg cagaatattt acttattctc | 300 |
| atcttaatac ataaaactta tcttttatcc atgaatcggc tcaaccgatg ggtccggcct | 360 |
| cgagtaaatc cacaagaaaa ctctcaagcg gcgtatcgcc aatcaatctg aagaaaaaca | 420 |
| ggtgatcgag acatttcaaa gagattgacc tcagagctgg caggcgaagc agcagggctg | 480 |
| cgaaacgacc ctcttccgct ggatgctgcg tcctgcaatg ctcgtccagg cacgcgtaaa | 540 |
| ccttttctcg taaagcatcc acttcctgtc tacatttcag tcctcgaata tcaggattaa | 600 |
| acagtattat agccttcaaa cagcctaatt ctgctctgtc caaatccatt cttctcattt | 660 |
| tgacacttaa tttctgacagt acccgatcga aaataggtcc gacgcagcc tggattgcac | 720 |
| tattccgatg taacgtcata ccaggaaaga aacacattaa ttcaggcggt cctggtggag | 780 |
| cgcgtctcct tgttgaagta tcactagaca tactggacgt acttgttcct gcatcggatt | 840 |
| ctagatactc aatacttctc caggctatag atgctataag taattcattc caggctgctc | 900 |
| tgagtaacgt tacttgatcc tctaattgta agcactaaa atgcggcatg caccttgcgt | 960 |
| attgtactaa ctgatataac tgtttatttg cttgctgaca cagactggat acagggccct | 1020 |
| tgtatctagg aggcaccatg gatgaaggtc ctactcgcaa atattgtatc gacaattccg | 1080 |
| ggtccgtcgc aacatttcga gtttcactcc tttgttctgc ttctaaaatt ctttctaccg | 1140 |

```
ttaaatcacg aacagaactt gtcgggttgc tttcttcatt attctttgct cctcgttgtc      1200
gttcttcctg cacggcttct cgtttcattc cacaggcgag acatttctga tatcgacaga      1260
actgacatcg atttctctgc cttttgtcga tcaaacaatt tctatctcct cgacaggcat      1320
acgtcagatc ttttcgtacc gtccgtttga aaaatcccct acaaccttcg caactgtaaa      1380
caccataatg cttcccggaa gccctatctc cctcgtgccg c                          1421

<210> SEQ ID NO 25
<211> LENGTH: 819
<212> TYPE: DNA
<213> ORGANISM: Ctenocephalides felis

<400> SEQUENCE: 25
aacaaaagct ggagctccac cgcggtggcg gccgctctag aactagtgga tcccccgggc       60
tgcaggaatt cggcacgaga ttttatgtag gttacaataa attttaaatt aaaattatgt      120
tgcacaatta cttttaacaa gttttttatt ttatcgttaa gtagtgcgtt atgttaattc      180
aaaataaatc gtttaatgaa cgaaattcat gagtttgttg aaggaaatag ttgatagttc      240 atcgaccttta agagtgacag tacgcggcca tgtttataca aatattaaat aatgttgctt      300
tattaaagtt cagttcaaaa aagctaaaat aagtgaaaaa gtgatactgc tagtttagtg      360
gaacaataat ggaaagtgca gacagaggct tggccttcga ccaagggctg tcaatgagct      420
cgatgggacc gctctcaccg ccggatatga accggatcc tgtgctactg aacggcggct      480
tttcgcccgg cagtggcggc gcagttgtcg gcagtcccgc tagtccgcct ttcggtcaaa      540
atcacacaat agtatcagga aacacggcca cgggcgccca aacgaaatca ccataccctc      600
caaatcatcc tttgagcggg tcaaaacatc tgtgctccat atgcggagat agggcttccg      660
ggaagcatta tggtgtttac agttgcgaag gttgtaaggg attttttcaaa cggacggtac      720 gaaaagatct gacgtatgcc tgtcgagaag atagaaattg tttgatcgac aaaaggcaga      780
gaaatcgatg tcagttctgt cgatatcaga aatgtctcg                             819

<210> SEQ ID NO 26
<211> LENGTH: 1749
<212> TYPE: DNA
<213> ORGANISM: Ctenocephalides felis
<220> FEATURE:
<221> NAME/KEY: CDS
<222> LOCATION: (306)..(1652)

<400> SEQUENCE: 26
tagtggaccc cccgggctgc aggaattcgg cacgagattt taaattaaaa ttatgttgca       60
caattacttt taacaagttt tttattttat cgttaagtag tgcgttatgt taattcaaaa      120
taaatcgttt aatgaacgaa attcatgagt ttgttgaagg aaatagttga tagttcatcg      180
accttacaga gtgacagtac gcggccatgt ttatacaaat attaataat gttgctttat      240 taaagttcag ttcaaaaaag ctaaaataag tgaaaagtg atactgctag tttagtggaa      300 caata atg gaa agt gca gac aga ggc ttg gcc ctc gac caa ggg ctg tca       350
      Met Glu Ser Ala Asp Arg Gly Leu Ala Leu Asp Gln Gly Leu Ser
       1               5                  10                  15 atg agc tcg atg gga ccg ctc tca ccg ccg gat atg aaa ccg gat cct        398
Met Ser Ser Met Gly Pro Leu Ser Pro Pro Asp Met Lys Pro Asp Pro
            20                  25                  30 gcg cta ctg aac ggc ggc ttt tcg ccc ggc agt ggc ggc gca gtt gtc        446
Ala Leu Leu Asn Gly Gly Phe Ser Pro Gly Ser Gly Gly Ala Val Val
        35                  40                  45
```

```
ggc agt ccc gct agt ccg cct ttt ggt caa aat cac aca ata gta tca      494
Gly Ser Pro Ala Ser Pro Pro Phe Gly Gln Asn His Thr Ile Val Ser
         50                  55                  60 gga aac acg gcc acg ggc gcc caa acg aaa tca cca tac cct cca aat      542
Gly Asn Thr Ala Thr Gly Ala Gln Thr Lys Ser Pro Tyr Pro Pro Asn
 65                  70                  75 cat cct ttg agc ggg tca aaa cat ctg tgc tcc ata tgc gga gat agg      590
His Pro Leu Ser Gly Ser Lys His Leu Cys Ser Ile Cys Gly Asp Arg
 80                  85                  90                  95 gct tcc ggg aag cat tat ggt gtt tac agt tgc gaa ggt tgt aag gga      638
Ala Ser Gly Lys His Tyr Gly Val Tyr Ser Cys Glu Gly Cys Lys Gly
                 100                 105                 110 ttt ttc aaa cgg acg gta cga aaa gat ctg acg tat gcc tgt cga gag      686
Phe Phe Lys Arg Thr Val Arg Lys Asp Leu Thr Tyr Ala Cys Arg Glu
             115                 120                 125 gat aga aat tgt ttg atc gac aaa agg cag aga aat cga tgt cag ttc      734
Asp Arg Asn Cys Leu Ile Asp Lys Arg Gln Arg Asn Arg Cys Gln Phe
         130                 135                 140 tgt cga tat cag aaa tgt ctc gcc tgt gga atg aaa cga gaa gcc gtg      782
Cys Arg Tyr Gln Lys Cys Leu Ala Cys Gly Met Lys Arg Glu Ala Val
 145                 150                 155 cag gaa gaa cga caa cga gga gca aag aat aat gaa gaa agc aac ccg      830
Gln Glu Glu Arg Gln Arg Gly Ala Lys Asn Asn Glu Glu Ser Asn Pro
160                 165                 170                 175 aca agt tct gtt cgt gat tta acg gta gaa aga att tta gaa gca gaa      878
Thr Ser Ser Val Arg Asp Leu Thr Val Glu Arg Ile Leu Glu Ala Glu
                 180                 185                 190 caa agg agt gaa act cga aat gtt gcg acg gac ccg gaa ttg tcg ata      926
Gln Arg Ser Glu Thr Arg Asn Val Ala Thr Asp Pro Glu Leu Ser Ile
             195                 200                 205 caa tat ttg cga gta gga cct tca tcc atg gtg cct cct aga tac aag      974
Gln Tyr Leu Arg Val Gly Pro Ser Ser Met Val Pro Pro Arg Tyr Lys
         210                 215                 220 ggc cct gta tcc agt ctg tgt cag caa gca aat aaa cag tta tat cag     1022
Gly Pro Val Ser Ser Leu Cys Gln Gln Ala Asn Lys Gln Leu Tyr Gln
 225                 230                 235 tta gta caa tac gca agg tgc atg ccg cat ttt agt gct tta caa tta     1070
Leu Val Gln Tyr Ala Arg Cys Met Pro His Phe Ser Ala Leu Gln Leu
240                 245                 250                 255 gag gat caa gta acg tta ctc aga gca gcc tgg aat gaa tta ctt ata     1118
Glu Asp Gln Val Thr Leu Leu Arg Ala Ala Trp Asn Glu Leu Leu Ile
                 260                 265                 270 gca tct ata gcc tgg aga agt att gag tat cta gaa tcc gat gca gaa     1166
Ala Ser Ile Ala Trp Arg Ser Ile Glu Tyr Leu Glu Ser Asp Ala Glu
             275                 280                 285 aca agt acg tcc agt atg tct agt gat act tca aca agg aga cgc gct     1214
Thr Ser Thr Ser Ser Met Ser Ser Asp Thr Ser Thr Arg Arg Arg Ala
         290                 295                 300 cca cca gga ccg cct gaa tta atg tgt ttc ttt cct ggt atg acg tta     1262
Pro Pro Gly Pro Pro Glu Leu Met Cys Phe Phe Pro Gly Met Thr Leu
 305                 310                 315 cat cgg aat agt gca atc cag gct ggc gtc gga cct att ttc gat cgg     1310
His Arg Asn Ser Ala Ile Gln Ala Gly Val Gly Pro Ile Phe Asp Arg
320                 325                 330                 335 gta ctg tca gaa tta agt gtc aaa atg aga aga atg gat ttg gac aga     1358
Val Leu Ser Glu Leu Ser Val Lys Met Arg Arg Met Asp Leu Asp Arg
                 340                 345                 350 gca gaa tta ggc tgt ttg aag gct ata ata ctg ttt aat cct gat att     1406
Ala Glu Leu Gly Cys Leu Lys Ala Ile Ile Leu Phe Asn Pro Asp Ile
```

```
                355                 360                  365
cga gga ctg aaa tgt aga cag gaa gtg gat gct tta cga gaa aag gtt    1454
Arg Gly Leu Lys Cys Arg Gln Glu Val Asp Ala Leu Arg Glu Lys Val
        370                 375                 380 tac gcg tgc ctg gac gag cat tgc agg acg cag cat cca gcg gaa gag    1502
Tyr Ala Cys Leu Asp Glu His Cys Arg Thr Gln His Pro Ala Glu Glu
385                 390                 395 ggt cgt ttc gca gcc ctg ctg ctt cgc ctg cca gct ctg agg tca atc    1550
Gly Arg Phe Ala Ala Leu Leu Leu Arg Leu Pro Ala Leu Arg Ser Ile
400                 405                 410                 415 tct ttg aaa tgt ctc gat cac ctg ttt ttc ttc aga ttg att ggc gat    1598
Ser Leu Lys Cys Leu Asp His Leu Phe Phe Phe Arg Leu Ile Gly Asp
                420                 425                 430 acg ccg ctt gag agt ttt ctt gtg gat tta ctc gag gcc gga ccg atc    1646
Thr Pro Leu Glu Ser Phe Leu Val Asp Leu Leu Glu Ala Gly Pro Ile
            435                 440                 445 ggt tga gccgattcat ggataaaaga taagttttat gtattaagat gagaataagt    1702
Gly aaatattctg caaagttatt ttttctgcac gaatatttct acaagca                1749

<210> SEQ ID NO 27
<211> LENGTH: 448
<212> TYPE: PRT
<213> ORGANISM: Ctenocephalides felis

<400> SEQUENCE: 27

Met Glu Ser Ala Asp Arg Gly Leu Ala Leu Asp Gln Gly Leu Ser Met
1               5                   10                  15

Ser Ser Met Gly Pro Leu Ser Pro Asp Met Lys Pro Asp Pro Ala
            20                  25                  30

Leu Leu Asn Gly Gly Phe Ser Pro Gly Ser Gly Gly Ala Val Val Gly
                35                  40                  45

Ser Pro Ala Ser Pro Pro Phe Gly Gln Asn His Thr Ile Val Ser Gly
        50                  55                  60

Asn Thr Ala Thr Gly Ala Gln Thr Lys Ser Pro Tyr Pro Pro Asn His
65                  70                  75                  80

Pro Leu Ser Gly Ser Lys His Leu Cys Ser Ile Cys Gly Asp Arg Ala
                85                  90                  95

Ser Gly Lys His Tyr Gly Val Tyr Ser Cys Glu Gly Cys Lys Gly Phe
            100                 105                 110

Phe Lys Arg Thr Val Arg Lys Asp Leu Thr Tyr Ala Cys Arg Glu Asp
        115                 120                 125

Arg Asn Cys Leu Ile Asp Lys Arg Gln Arg Asn Arg Cys Gln Phe Cys
    130                 135                 140

Arg Tyr Gln Lys Cys Leu Ala Cys Gly Met Lys Arg Glu Ala Val Gln
145                 150                 155                 160

Glu Glu Arg Gln Arg Gly Ala Lys Asn Asn Glu Ser Asn Pro Thr
                165                 170                 175

Ser Ser Val Arg Asp Leu Thr Val Glu Arg Ile Leu Glu Ala Glu Gln
            180                 185                 190

Arg Ser Glu Thr Arg Asn Val Ala Thr Asp Pro Glu Leu Ser Ile Gln
        195                 200                 205

Tyr Leu Arg Val Gly Pro Ser Ser Met Val Pro Pro Arg Tyr Lys Gly
    210                 215                 220

Pro Val Ser Ser Leu Cys Gln Gln Ala Asn Lys Gln Leu Tyr Gln Leu
225                 230                 235                 240
```

```
Val Gln Tyr Ala Arg Cys Met Pro His Phe Ser Ala Leu Gln Leu Glu
            245                 250                 255

Asp Gln Val Thr Leu Leu Arg Ala Ala Trp Asn Glu Leu Leu Ile Ala
            260                 265                 270

Ser Ile Ala Trp Arg Ser Ile Glu Tyr Leu Glu Ser Asp Ala Glu Thr
            275                 280                 285

Ser Thr Ser Ser Met Ser Ser Asp Thr Ser Thr Arg Arg Arg Ala Pro
            290                 295                 300

Pro Gly Pro Pro Glu Leu Met Cys Phe Phe Pro Gly Met Thr Leu His
305                 310                 315                 320

Arg Asn Ser Ala Ile Gln Ala Gly Val Gly Pro Ile Phe Asp Arg Val
            325                 330                 335

Leu Ser Glu Leu Ser Val Lys Met Arg Met Asp Leu Asp Arg Ala
            340                 345                 350

Glu Leu Gly Cys Leu Lys Ala Ile Ile Leu Phe Asn Pro Asp Ile Arg
            355                 360                 365

Gly Leu Lys Cys Arg Gln Glu Val Asp Ala Leu Arg Glu Lys Val Tyr
370                 375                 380

Ala Cys Leu Asp Glu His Cys Arg Thr Gln His Pro Ala Glu Glu Gly
385                 390                 395                 400

Arg Phe Ala Ala Leu Leu Arg Leu Pro Ala Leu Arg Ser Ile Ser
            405                 410                 415

Leu Lys Cys Leu Asp His Leu Phe Phe Phe Arg Leu Ile Gly Asp Thr
            420                 425                 430

Pro Leu Glu Ser Phe Leu Val Asp Leu Leu Glu Ala Gly Pro Ile Gly
            435                 440                 445

<210> SEQ ID NO 28
<211> LENGTH: 1749
<212> TYPE: DNA
<213> ORGANISM: Ctenocephalides felis

<400> SEQUENCE: 28
tgcttgtaga aatattcgtg cagaaaaaat aactttgcag aatatttact tattctcatc      60
ttaatacata aaacttatct tttatccatg aatcggctca accgatcggt ccggcctcga     120
gtaaatccac aagaaaactc tcaagcggcg tatcgccaat caatctgaag aaaaacaggt     180
gatcgagaca tttcaaagag attgacctca gagctggcag gcgaagcagc agggctgcga     240
aacgaccctc ttccgctgga tgctgcgtcc tgcaatgctc gtccaggcac gcgtaaacct     300
tttctcgtaa agcatccact tcctgtctac atttcagtcc tcgaatatca ggattaaaca     360
gtattatagc cttcaaacag cctaattctg ctctgtccaa atccattctt ctcatttga      420 cacttaattc tgacagtacc cgatcgaaaa taggtccgac gccagcctgg attgcactat     480
tccgatgtaa cgtcatacca ggaaagaaac acattaattc aggcggtcct ggtggagcgc     540
gtctccttgt tgaagtatca ctagacatac tggacgtact tgtttctgca tcggattcta     600
gatactcaat aacttctccag gctatagatg ctataagtaa ttcattccag gctgctctga     660
gtaacgttac ttgatcctct aattgtaaag cactaaaatg cggcatgcac cttgcgtatt     720
gtactaactg atataactgt ttatttgctt gctgacacag actggataca gggcccttgt     780
atctaggagg caccatggat gaaggtccta ctcgcaaata ttgtatcgac aattccgggt     840
ccgtcgcaac atttcgagtt tcactccttt gttctgcttc taaaattctt tctaccgtta     900
aatcacgaac agaacttgtc gggttgcttt cttcattatt ctttgctcct cgttgtcgtt     960
```

```
cttcctgcac ggcttctcgt ttcattccac aggcgagaca tttctgatat cgacagaact   1020
gacatcgatt tctctgcctt tgtcgatca  aacaatttct atcctctcga caggcatacg   1080
tcagatcttt tcgtaccgtc cgtttgaaaa atcccttaca accttcgcaa ctgtaaacac   1140
cataatgctt cccggaagcc ctatctccgc atatggagca cagatgtttt gacccgctca   1200
aaggatgatt tggagggtat ggtgatttcg tttgggcgcc cgtggccgtg tttcctgata   1260
ctattgtgtg attttgacca aaaggcggac tagcgggact gccgacaact cgccgccac    1320 tgccgggcga aaagccgccg ttcagtagcg caggatccgg tttcatatcc ggcggtgaga   1380
gcggtcccat cgagctcatt gacagccctt ggtcgagggc caagcctctg tctgcacttt   1440
ccattattgt tccactaaac tagcagtatc actttttcac ttattttagc ttttttgaac   1500
tgaactttaa taaagcaaca ttatttaata tttgtataaa catggccgcg tactgtcact   1560
ctgtaaggtc gatgaactat caactatttc cttcaacaaa ctcatgaatt tcgttcatta   1620
aacgatttat tttgaattaa cataacgcac tacttaacga taaaataaaa aacttgttaa   1680
aagtaattgt gcaacataat tttaatttaa aatctcgtgc cgaattcctg cagcccgggg   1740
ggtccacta                                                           1749

<210> SEQ ID NO 29
<211> LENGTH: 1344
<212> TYPE: DNA
<213> ORGANISM: Ctenocephalides felis
<220> FEATURE:
<221> NAME/KEY: CDS
<222> LOCATION: (1)..(1344)

<400> SEQUENCE: 29 atg gaa agt gca gac aga ggc ttg gcc ctc gac caa ggg ctg tca atg         48
Met Glu Ser Ala Asp Arg Gly Leu Ala Leu Asp Gln Gly Leu Ser Met
1               5                   10                  15 agc tcg atg gga ccg ctc tca ccg ccg gat atg aaa ccg gat cct gcg         96
Ser Ser Met Gly Pro Leu Ser Pro Pro Asp Met Lys Pro Asp Pro Ala
            20                  25                  30 cta ctg aac ggc ggc ttt tcg ccc ggt agt ggc ggc gca gtt gtc ggc        144
Leu Leu Asn Gly Gly Phe Ser Pro Gly Ser Gly Gly Ala Val Val Gly
        35                  40                  45 agt ccc gct agt ccg cct ttt ggt caa aat cac aca ata gta tca gga        192
Ser Pro Ala Ser Pro Pro Phe Gly Gln Asn His Thr Ile Val Ser Gly
    50                  55                  60 aac acg gcc acg ggc gcc caa acg aaa tca cca tac cct cca aat cat        240
Asn Thr Ala Thr Gly Ala Gln Thr Lys Ser Pro Tyr Pro Pro Asn His
65                  70                  75                  80 cct ttg agc ggg tca aaa cat ctg tgc tcc ata tgc gga gat agg gct        288
Pro Leu Ser Gly Ser Lys His Leu Cys Ser Ile Cys Gly Asp Arg Ala
                85                  90                  95 tcc ggg aag cat tat ggt gtt tac agt tgc gaa ggt tgt aag gga ttt        336
Ser Gly Lys His Tyr Gly Val Tyr Ser Cys Glu Gly Cys Lys Gly Phe
            100                 105                 110 ttc aaa cgg acg gta cga aaa gat ctg acg tat gcc tgt cga gag gat        384
Phe Lys Arg Thr Val Arg Lys Asp Leu Thr Tyr Ala Cys Arg Glu Asp
        115                 120                 125 aga aat tgt ttg atc gac aaa agg cag aga aat cga tgt cag ttc tgt        432
Arg Asn Cys Leu Ile Asp Lys Arg Gln Arg Asn Arg Cys Gln Phe Cys
    130                 135                 140 cga tat cag aaa tgt ctc gcc tgt gga atg aaa cga gaa gcc gtg cag        480
Arg Tyr Gln Lys Cys Leu Ala Cys Gly Met Lys Arg Glu Ala Val Gln
145                 150                 155                 160
```

```
gaa gaa cga caa cga gga gca aag aat aat gaa gaa agc aac ccg aca         528
Glu Glu Arg Gln Arg Gly Ala Lys Asn Asn Glu Glu Ser Asn Pro Thr
                165                 170                 175 agt tct gtt cgt gat tta acg gta gaa aga att tta gaa gca gaa caa         576
Ser Ser Val Arg Asp Leu Thr Val Glu Arg Ile Leu Glu Ala Glu Gln
        180                 185                 190 agg agt gaa act cga aat gtt gcg acg gac ccg gaa ttg tcg ata caa         624
Arg Ser Glu Thr Arg Asn Val Ala Thr Asp Pro Glu Leu Ser Ile Gln
            195                 200                 205 tat ttg cga gta gga cct tca tcc atg gtg cct cct aga tac aag ggc         672
Tyr Leu Arg Val Gly Pro Ser Ser Met Val Pro Pro Arg Tyr Lys Gly
    210                 215                 220 cct gta tcc agt ctg tgt cag caa gca aat aaa cag tta tat cag tta         720
Pro Val Ser Ser Leu Cys Gln Gln Ala Asn Lys Gln Leu Tyr Gln Leu
225                 230                 235                 240 gta caa tac gca agg tgc atg ccg cat ttt agt gct tta caa tta gag         768
Val Gln Tyr Ala Arg Cys Met Pro His Phe Ser Ala Leu Gln Leu Glu
                245                 250                 255 gat caa gta acg tta ctc aga gca gcc tgg aat gaa tta ctt ata gca         816
Asp Gln Val Thr Leu Leu Arg Ala Ala Trp Asn Glu Leu Leu Ile Ala
        260                 265                 270 tct ata gcc tgg aga agt att gag tat cta gaa tcc gat gca gaa aca         864
Ser Ile Ala Trp Arg Ser Ile Glu Tyr Leu Glu Ser Asp Ala Glu Thr
            275                 280                 285 agt acg tcc agt atg tct agt gat act tca aca agg aga cgc gct cca         912
Ser Thr Ser Ser Met Ser Ser Asp Thr Ser Thr Arg Arg Arg Ala Pro
    290                 295                 300 cca gga ccg cct gaa tta atg tgt ttc ttt cct ggt atg acg tta cat         960
Pro Gly Pro Pro Glu Leu Met Cys Phe Phe Pro Gly Met Thr Leu His
305                 310                 315                 320 cgg aat agt gca atc cag gct ggc gtc gga cct att ttc gat cgg gta        1008
Arg Asn Ser Ala Ile Gln Ala Gly Val Gly Pro Ile Phe Asp Arg Val
                325                 330                 335 ctg tca gaa tta agt gtc aaa atg aga aga atg gat ttg gac aga gca        1056
Leu Ser Glu Leu Ser Val Lys Met Arg Arg Met Asp Leu Asp Arg Ala
        340                 345                 350 gaa tta ggc tgt ttg aag gct ata ata ctg ttt aat cct gat att cga        1104
Glu Leu Gly Cys Leu Lys Ala Ile Ile Leu Phe Asn Pro Asp Ile Arg
            355                 360                 365 gga ctg aaa tgt aga cag gaa gtg gat gct tta cga gaa aag gtt tac        1152
Gly Leu Lys Cys Arg Gln Glu Val Asp Ala Leu Arg Glu Lys Val Tyr
    370                 375                 380 gcg tgc ctg gac gag cat tgc agg acg cag cat cca gcg gaa gag ggt        1200
Ala Cys Leu Asp Glu His Cys Arg Thr Gln His Pro Ala Glu Glu Gly
385                 390                 395                 400 cgt ttc gca gcc ctg ctg ctt cgc ctg cca gct ctg agg tca atc tct        1248
Arg Phe Ala Ala Leu Leu Leu Arg Leu Pro Ala Leu Arg Ser Ile Ser
                405                 410                 415 ttg aaa tgt ctc gat cac ctg ttt ttc aga ttg att ggc gat acg             1296
Leu Lys Cys Leu Asp His Leu Phe Phe Arg Leu Ile Gly Asp Thr
        420                 425                 430 ccg ctt gag agt ttt ctt gtg gat tta ctc gag gcc gga ccg atc ggt        1344
Pro Leu Glu Ser Phe Leu Val Asp Leu Leu Glu Ala Gly Pro Ile Gly
            435                 440                 445
```

<210> SEQ ID NO 30
<211> LENGTH: 448
<212> TYPE: PRT
<213> ORGANISM: Ctenocephalides felis

```
<400> SEQUENCE: 30

Met Glu Ser Ala Asp Arg Gly Leu Ala Leu Asp Gln Gly Leu Ser Met
1               5                   10                  15

Ser Ser Met Gly Pro Leu Ser Pro Pro Asp Met Lys Pro Asp Pro Ala
            20                  25                  30

Leu Leu Asn Gly Gly Phe Ser Pro Gly Ser Gly Ala Val Val Gly
                35                  40                  45

Ser Pro Ala Ser Pro Pro Phe Gly Gln Asn His Thr Ile Val Ser Gly
        50                  55                  60

Asn Thr Ala Thr Gly Ala Gln Thr Lys Ser Pro Tyr Pro Pro Asn His
65                  70                  75                  80

Pro Leu Ser Gly Ser Lys His Leu Cys Ser Ile Cys Gly Asp Arg Ala
                85                  90                  95

Ser Gly Lys His Tyr Gly Val Tyr Ser Cys Glu Gly Cys Lys Gly Phe
            100                 105                 110

Phe Lys Arg Thr Val Arg Lys Asp Leu Thr Tyr Ala Cys Arg Glu Asp
        115                 120                 125

Arg Asn Cys Leu Ile Asp Lys Arg Gln Arg Asn Arg Cys Gln Phe Cys
130                 135                 140

Arg Tyr Gln Lys Cys Leu Ala Cys Gly Met Lys Arg Glu Ala Val Gln
145                 150                 155                 160

Glu Glu Arg Gln Arg Gly Ala Lys Asn Asn Glu Ser Asn Pro Thr
                165                 170                 175

Ser Ser Val Arg Asp Leu Thr Val Glu Arg Ile Leu Glu Ala Glu Gln
            180                 185                 190

Arg Ser Glu Thr Arg Asn Val Ala Thr Asp Pro Glu Leu Ser Ile Gln
        195                 200                 205

Tyr Leu Arg Val Gly Pro Ser Ser Met Val Pro Pro Arg Tyr Lys Gly
        210                 215                 220

Pro Val Ser Ser Leu Cys Gln Gln Ala Asn Lys Gln Leu Tyr Gln Leu
225                 230                 235                 240

Val Gln Tyr Ala Arg Cys Met Pro His Phe Ser Ala Leu Gln Leu Glu
                245                 250                 255

Asp Gln Val Thr Leu Leu Arg Ala Ala Trp Asn Glu Leu Leu Ile Ala
            260                 265                 270

Ser Ile Ala Trp Arg Ser Ile Glu Tyr Leu Glu Ser Asp Ala Glu Thr
        275                 280                 285

Ser Thr Ser Ser Met Ser Ser Asp Thr Ser Thr Arg Arg Arg Ala Pro
            290                 295                 300

Pro Gly Pro Pro Glu Leu Met Cys Phe Phe Pro Gly Met Thr Leu His
305                 310                 315                 320

Arg Asn Ser Ala Ile Gln Ala Gly Val Gly Pro Ile Phe Asp Arg Val
                325                 330                 335

Leu Ser Glu Leu Ser Val Lys Met Arg Arg Met Asp Leu Asp Arg Ala
            340                 345                 350

Glu Leu Gly Cys Leu Lys Ala Ile Ile Leu Phe Asn Pro Asp Ile Arg
        355                 360                 365

Gly Leu Lys Cys Arg Gln Glu Val Asp Ala Leu Arg Glu Lys Val Tyr
    370                 375                 380

Ala Cys Leu Asp Glu His Cys Arg Thr Gln His Pro Ala Glu Glu Gly
385                 390                 395                 400

Arg Phe Ala Ala Leu Leu Leu Arg Leu Pro Ala Leu Arg Ser Ile Ser
                405                 410                 415
```

Leu Lys Cys Leu Asp His Leu Phe Phe Phe Arg Leu Ile Gly Asp Thr
        420                 425                 430

Pro Leu Glu Ser Phe Leu Val Asp Leu Leu Glu Ala Gly Pro Ile Gly
        435                 440                 445

<210> SEQ ID NO 31
<211> LENGTH: 1344
<212> TYPE: DNA
<213> ORGANISM: Ctenocephalides felis

<400> SEQUENCE: 31

| | | |
|---|---|---|
| accgatcggt ccggcctcga gtaaatccac aagaaaactc tcaagcggcg tatcgccaat | 60 |
| caatctgaag aaaaacaggt gatcgagaca tttcaaagag attgacctca gagctggcag | 120 |
| gcgaagcagc agggctgcga acgaccctc ttccgctgga tgctgcgtcc tgcaatgctc | 180 |
| gtccaggcac gcgtaaacct tttctcgtaa agcatccact tcctgtctac atttcagtcc | 240 |
| tcgaatatca ggattaaaca gtattatagc cttcaaacag cctaattctg ctctgtccaa | 300 |
| atccattctt ctcattttga cacttaattc tgacagtacc cgatcgaaaa taggtccgac | 360 |
| gccagcctgg attgcactat tccgatgtaa cgtcatacca ggaaagaaac acattaattc | 420 |
| aggcggtcct ggtggagcgc gtctccttgt tgaagtatca ctagacatac tggacgtact | 480 |
| tgtttctgca tcggattcta gatactcaat acttctccag gctatagatg ctataagtaa | 540 |
| ttcattccag gctgctctga gtaacgttac ttgatcctct aattgtaaag cactaaaatg | 600 |
| cggcatgcac cttgcgtatt gtactaactg atataactgt ttatttgctt gctgacacag | 660 |
| actggataca gggcccttgt atctaggagg caccatggat gaaggtccta ctcgcaaata | 720 |
| ttgtatcgac aattccgggt ccgtcgcaac atttcgagtt tcactccttt gttctgcttc | 780 |
| taaaattctt tctaccgtta aatcacgaac agaacttgtc gggttgcttt cttcattatt | 840 |
| cttgctcct cgttgtcgtt cttcctgcac ggcttctcgt ttcattccac aggcgagaca | 900 |
| tttctgatat cgacagaact gacatcgatt tctctgcctt tgtcgatca aacaatttct | 960 |
| atcctctcga caggcatacg tcagatcttt tcgtaccgtc cgtttgaaaa tcccttaca | 1020 |
| accttcgcaa ctgtaaacac cataatgctt cccggaagcc ctatctccgc atatggagca | 1080 |
| cagatgtttt gacccgctca aaggatgatt tggagggtat ggtgatttcg tttgggcgcc | 1140 |
| cgtggccgtg tttcctgata ctattgtgtg atttgacca aaaggcggac tagcgggact | 1200 |
| gccgacaact gcgccgccac tgccgggcga aaagccgccg ttcagtagcg caggatccgg | 1260 |
| tttcatatcc ggcggtgaga gcggtcccat cgagctcatt gacagcccctt ggtcgagggc | 1320 |
| caagcctctg tctgcacttt ccat | 1344 |

<210> SEQ ID NO 32
<211> LENGTH: 1975
<212> TYPE: DNA
<213> ORGANISM: Ctenocephalides felis
<220> FEATURE:
<221> NAME/KEY: CDS
<222> LOCATION: (454)..(1878)

<400> SEQUENCE: 32

| | | |
|---|---|---|
| agtcaagtga ttgaagtgat ggtatgcgcg cgactcggtt tgttttgacg tgttcgaaga | 60 |
| tgaacgatat tttaaatatt ttgtgtttag ttttagtctc gagataattt ttgtgctgtg | 120 |
| tgataagagt tgtgctttca taaaaaggaa ttgtttatta gatttgaat gacagtgccc | 180 |
| catgtgggag atgacatact gaacgtatta gtttatatgt tgcttataat tgagtatagg | 240 |

```
aataaactgt taatttcaat tttttggtaa ctccaaatgt tacctcaaaa acttaaagta      300
agggtcaaat ataaaaaaag tgtcattaag aaattcaaca tgactagtac acatatcagt      360
gagtgagttt atattagaaa tgaaggagac gcataaatgg taacttaatt aagcattaca      420
atcaactggg aataaataaa tatatcttct aaa atg atg aaa aaa gag aag cct      474
                                    Met Met Lys Lys Glu Lys Pro
                                     1               5 atg atg tct gtg acg gct ttg att caa gga gcc gct cag aat caa ata        522
Met Met Ser Val Thr Ala Leu Ile Gln Gly Ala Ala Gln Asn Gln Ile
         10              15                  20 tgg gga cga gga tta tct ggc ctt aca ggc ttg gcc ctc gac caa ggg        570
Trp Gly Arg Gly Leu Ser Gly Leu Thr Gly Leu Ala Leu Asp Gln Gly
     25              30                  35 ctg tca atg agc tcg atg gga ccg ctc tca ctg ccg gat atg aaa ccg        618
Leu Ser Met Ser Ser Met Gly Pro Leu Ser Leu Pro Asp Met Lys Pro
40              45                  50                  55 gat cct gcg cta ctg aac ggc ggc ttt tcg ccc ggc agt ggc ggc gca        666
Asp Pro Ala Leu Leu Asn Gly Gly Phe Ser Pro Gly Ser Gly Gly Ala
                 60                  65                  70 gtt gtc ggc agt ccc gct agt ccg cct ttt ggt caa aat cac aca ata        714
Val Val Gly Ser Pro Ala Ser Pro Pro Phe Gly Gln Asn His Thr Ile
             75                  80                  85 gta tca gga aac acg gcc acg ggc gcc caa acg aaa tca cca tac cct        762
Val Ser Gly Asn Thr Ala Thr Gly Ala Gln Thr Lys Ser Pro Tyr Pro
                 90                  95                 100 cca aat cat cct ttg agc ggg tca aaa cat ctg tgc tcc ata tgc gga        810
Pro Asn His Pro Leu Ser Gly Ser Lys His Leu Cys Ser Ile Cys Gly
        105                 110                 115 gat agg gct tcc ggg aag cat tat ggt gtt tac agt tgc gaa ggt tgt        858
Asp Arg Ala Ser Gly Lys His Tyr Gly Val Tyr Ser Cys Glu Gly Cys
120                 125                 130                 135 aag gga ttt ttc aaa cgg acg gta cga aaa gat ctg acg tat gcc tgt        906
Lys Gly Phe Phe Lys Arg Thr Val Arg Lys Asp Leu Thr Tyr Ala Cys
                140                 145                 150 cga gag gat aga aat tgt ttg atc gac aaa agg cag aga aat cga tgt        954
Arg Glu Asp Arg Asn Cys Leu Ile Asp Lys Arg Gln Arg Asn Arg Cys
            155                 160                 165 cag ttc tgt cga tat cag aaa tgt ctc gcc tgt gga atg aaa cga gaa       1002
Gln Phe Cys Arg Tyr Gln Lys Cys Leu Ala Cys Gly Met Lys Arg Glu
        170                 175                 180 gcc gtg cag gaa gaa cga caa cga gga gca aag aat aat gaa gaa agc       1050
Ala Val Gln Glu Glu Arg Gln Arg Gly Ala Lys Asn Asn Glu Glu Ser
    185                 190                 195 aac ccg aca agt tct gtt cgt gat tta acg gta gaa aga att tta gaa       1098
Asn Pro Thr Ser Ser Val Arg Asp Leu Thr Val Glu Arg Ile Leu Glu
200                 205                 210                 215 gca gaa caa agg agt gaa act cga aat gtt gcg acg gac ccg gaa ttg       1146
Ala Glu Gln Arg Ser Glu Thr Arg Asn Val Ala Thr Asp Pro Glu Leu
                220                 225                 230 tcg ata caa tat ttg cga gta gga cct tca tcc atg gtg cct cct aga       1194
Ser Ile Gln Tyr Leu Arg Val Gly Pro Ser Ser Met Val Pro Pro Arg
            235                 240                 245 tac aag ggc cct gta tcc agt ctg tgt cag caa gca aat aaa cag tta       1242
Tyr Lys Gly Pro Val Ser Ser Leu Cys Gln Gln Ala Asn Lys Gln Leu
        250                 255                 260 tat cag tta gta caa tac gca agg tgc atg ccg cat ttt agt gct tta       1290
Tyr Gln Leu Val Gln Tyr Ala Arg Cys Met Pro His Phe Ser Ala Leu
    265                 270                 275
```

```
caa tta gag gat caa gta acg tta ctc aga gca gcc tgg aat gaa tta    1338
Gln Leu Glu Asp Gln Val Thr Leu Leu Arg Ala Ala Trp Asn Glu Leu
280                 285                 290                 295 ctt ata gca tct ata gcc tgg aga agt att gag tat cta gaa tcc gat    1386
Leu Ile Ala Ser Ile Ala Trp Arg Ser Ile Glu Tyr Leu Glu Ser Asp
                300                 305                 310 gca gaa aca agt acg tcc agt atg tct agt gat act tca aca agg aga    1434
Ala Glu Thr Ser Thr Ser Ser Met Ser Ser Asp Thr Ser Thr Arg Arg
            315                 320                 325 cgc gct cca cca gga ccg cct gaa tta atg tgt ttc ttt cct ggt atg    1482
Arg Ala Pro Pro Gly Pro Pro Glu Leu Met Cys Phe Phe Pro Gly Met
        330                 335                 340 acg tta cat cgg aat agt gca atc cag gct ggc gtc gga cct att ttc    1530
Thr Leu His Arg Asn Ser Ala Ile Gln Ala Gly Val Gly Pro Ile Phe
    345                 350                 355 gat cgg gta ctg tca gaa tta agt gtc aaa atg aga aga atg gat ttg    1578
Asp Arg Val Leu Ser Glu Leu Ser Val Lys Met Arg Arg Met Asp Leu
360                 365                 370                 375 gac aga gca gaa tta ggc tgt ttg aag gct ata ata ctg ttt aat cct    1626
Asp Arg Ala Glu Leu Gly Cys Leu Lys Ala Ile Ile Leu Phe Asn Pro
                380                 385                 390 gat att cga gga ctg aaa tgt aga cag gaa gtg gat gct tta cga gaa    1674
Asp Ile Arg Gly Leu Lys Cys Arg Gln Glu Val Asp Ala Leu Arg Glu
            395                 400                 405 aag gtt tac gcg tgc ctg gac gag cat tgc agg acg cag cat cca gcg    1722
Lys Val Tyr Ala Cys Leu Asp Glu His Cys Arg Thr Gln His Pro Ala
        410                 415                 420 gaa gag ggt cgt ttc gca gcc ctg ctg ctt cgc ctg cca gct ctg agg    1770
Glu Glu Gly Arg Phe Ala Ala Leu Leu Leu Arg Leu Pro Ala Leu Arg
    425                 430                 435 tca atc tct ttg aaa tgt ctc gat cac ctg ttt ttc ttc aga ttg att    1818
Ser Ile Ser Leu Lys Cys Leu Asp His Leu Phe Phe Phe Arg Leu Ile
440                 445                 450                 455 ggc gat acg ccg ctt gag agt ttt ctt gtg gat tta ctc gag gcc gga    1866
Gly Asp Thr Pro Leu Glu Ser Phe Leu Val Asp Leu Leu Glu Ala Gly
                460                 465                 470 ccg atc ggt tga gccgattcat ggataaaaga taagttttat gtattaagat       1918
Pro Ile Gly gagaataagt aaatattctg caaagttatt ttttctgcac gaatatttct acaagca    1975

<210> SEQ ID NO 33
<211> LENGTH: 474
<212> TYPE: PRT
<213> ORGANISM: Ctenocephalides felis

<400> SEQUENCE: 33

Met Met Lys Lys Glu Lys Pro Met Met Ser Val Thr Ala Leu Ile Gln
1               5                   10                  15

Gly Ala Ala Gln Asn Gln Ile Trp Gly Arg Gly Leu Ser Gly Leu Thr
            20                  25                  30

Gly Leu Ala Leu Asp Gln Gly Leu Ser Met Ser Ser Met Gly Pro Leu
        35                  40                  45

Ser Leu Pro Asp Met Lys Pro Asp Pro Ala Leu Leu Asn Gly Gly Phe
    50                  55                  60

Ser Pro Gly Ser Gly Gly Ala Val Val Gly Ser Pro Ala Ser Pro Pro
65                  70                  75                  80

Phe Gly Gln Asn His Thr Ile Val Ser Gly Asn Thr Ala Thr Gly Ala
                85                  90                  95
```

```
Gln Thr Lys Ser Pro Tyr Pro Pro Asn His Pro Leu Ser Gly Ser Lys
            100                 105                 110

His Leu Cys Ser Ile Cys Gly Asp Arg Ala Ser Gly Lys His Tyr Gly
        115                 120                 125

Val Tyr Ser Cys Glu Gly Cys Lys Gly Phe Phe Lys Arg Thr Val Arg
    130                 135                 140

Lys Asp Leu Thr Tyr Ala Cys Arg Glu Asp Arg Asn Cys Leu Ile Asp
145                 150                 155                 160

Lys Arg Gln Arg Asn Arg Cys Gln Phe Cys Arg Tyr Gln Lys Cys Leu
                165                 170                 175

Ala Cys Gly Met Lys Arg Glu Ala Val Gln Glu Glu Arg Gln Arg Gly
            180                 185                 190

Ala Lys Asn Asn Glu Glu Ser Asn Pro Thr Ser Ser Val Arg Asp Leu
        195                 200                 205

Thr Val Glu Arg Ile Leu Glu Ala Glu Gln Arg Ser Glu Thr Arg Asn
    210                 215                 220

Val Ala Thr Asp Pro Glu Leu Ser Ile Gln Tyr Leu Arg Val Gly Pro
225                 230                 235                 240

Ser Ser Met Val Pro Pro Arg Tyr Lys Gly Pro Val Ser Ser Leu Cys
                245                 250                 255

Gln Gln Ala Asn Lys Gln Leu Tyr Gln Leu Val Gln Tyr Ala Arg Cys
            260                 265                 270

Met Pro His Phe Ser Ala Leu Gln Leu Glu Asp Gln Val Thr Leu Leu
        275                 280                 285

Arg Ala Ala Trp Asn Glu Leu Leu Ile Ala Ser Ile Ala Trp Arg Ser
    290                 295                 300

Ile Glu Tyr Leu Glu Ser Asp Ala Glu Thr Ser Thr Ser Ser Met Ser
305                 310                 315                 320

Ser Asp Thr Ser Thr Arg Arg Ala Pro Pro Gly Pro Pro Glu Leu
                325                 330                 335

Met Cys Phe Phe Pro Gly Met Thr Leu His Arg Asn Ser Ala Ile Gln
            340                 345                 350

Ala Gly Val Gly Pro Ile Phe Asp Arg Val Leu Ser Glu Leu Ser Val
        355                 360                 365

Lys Met Arg Arg Met Asp Leu Asp Arg Ala Glu Leu Gly Cys Leu Lys
    370                 375                 380

Ala Ile Ile Leu Phe Asn Pro Asp Ile Arg Gly Leu Lys Cys Arg Gln
385                 390                 395                 400

Glu Val Asp Ala Leu Arg Glu Lys Val Tyr Ala Cys Leu Asp Glu His
                405                 410                 415

Cys Arg Thr Gln His Pro Ala Glu Glu Gly Arg Phe Ala Ala Leu Leu
            420                 425                 430

Leu Arg Leu Pro Ala Leu Arg Ser Ile Ser Leu Lys Cys Leu Asp His
        435                 440                 445

Leu Phe Phe Phe Arg Leu Ile Gly Asp Thr Pro Leu Glu Ser Phe Leu
    450                 455                 460

Val Asp Leu Leu Glu Ala Gly Pro Ile Gly
465                 470
```

<210> SEQ ID NO 34
<211> LENGTH: 1975
<212> TYPE: DNA
<213> ORGANISM: Ctenocephalides felis

<400> SEQUENCE: 34

```
tgcttgtaga aatattcgtg cagaaaaaat aactttgcag aatatttact tattctcatc    60
ttaatacata aaacttatct tttatccatg aatcggctca accgatcggt ccggcctcga   120
gtaaatccac aagaaaactc tcaagcggcg tatcgccaat caatctgaag aaaaacaggt   180
gatcgagaca tttcaaagag attgacctca gagctggcag gcgaagcagc agggctgcga   240
aacgaccctc ttccgctgga tgctgcgtcc tgcaatgctc gtccaggcac gcgtaaacct   300
tttctcgtaa agcatccact tcctgtctac atttcagtcc tcgaatatca ggattaaaca   360
gtattatagc cttcaaacag cctaattctg ctctgtccaa atccattctt ctcattttga   420
cacttaattc tgacagtacc cgatcgaaaa taggtccgac gccagcctgg attgcactat   480
tccgatgtaa cgtcatacca ggaaagaaac acattaattc aggcggtcct ggtggagcgc   540
gtctccttgt tgaagtatca ctagacatac tggacgtact tgtttctgca tcggattcta   600
gatactcaat acttctccag gctatagatg ctataagtaa ttcattccag gctgctctga   660
gtaacgttac ttgatcctct aattgtaaag cactaaaatg cggcatgcac cttgcgtatt   720
gtactaactg atataactgt ttatttgctt gctgacacag actggataca gggcccttgt   780
atctaggagg caccatggat gaaggtccta ctcgcaaata ttgtatcgac aattccgggt   840
ccgtcgcaac atttcgagtt tcactccttt gttctgcttc taaaattctt tctaccgtta   900
aatcacgaac agaacttgtc gggttgcttt cttcattatt ctttgctcct cgttgtcgtt   960
cttcctgcac ggcttctcgt ttcattccac aggcgagaca tttctgatat cgacagaact  1020
gacatcgatt tctctgcctt tgtcgatca aacaatttct atcctctcga caggcatacg  1080
tcagatcttt tcgtaccgtc cgtttgaaaa atcccttaca accttcgcaa ctgtaaacac  1140
cataatgctt cccggaagcc ctatctccgc atatggagca cagatgtttt gacccgctca  1200
aaggatgatt tggagggtat ggtgatttcg tttgggcgcc cgtggccgtg tttcctgata  1260
ctattgtgtg attttgacca aaaggcggac tagcgggact gccgacaact cgccgccac  1320 tgccgggcga aaagccgccg ttcagtagcg caggatccgg tttcatatcc ggcagtgaga  1380
gcggtcccat cgagctcatt gacagccctt ggtcgagggc caagcctgta aggccagata  1440
atcctcgtcc ccatatttga ttctgagcgg ctccttgaat caaagccgtc acagacatca  1500
taggcttctc ttttttcatc attttagaag atatatttat ttattcccag ttgattgtaa  1560
tgcttaatta agttaccatt tatgcgtctc cttcatttct aatataaact cactcactga  1620
tatgtgtact agtcatgttg aatttcttaa tgcacttttt tttatatttg acccttactt  1680
taagttttgt aggtaacatt tggagttacc aaaaaattga aattaacagt ttattcctat  1740
actcaattat aagcaacata taaactaata cgttcagtat gtcatctccc acatggggca  1800
ctgtcattca aaatctaata aacaattcct ttttatgaaa gcacaactct tatcacacag  1860
cacaaaaatt atctcgagac taaaactaaa cacaaaatat ttaaaatatc gttcatcttc  1920
gaacacgtca aaacaaaccg agtcgcgcgc ataccatcac ttcaatcact tgact         1975
```

<210> SEQ ID NO 35
<211> LENGTH: 1422
<212> TYPE: DNA
<213> ORGANISM: Ctenocephalides felis
<220> FEATURE:
<221> NAME/KEY: CDS
<222> LOCATION: (1)..(1422)

<400> SEQUENCE: 35

```
atg atg aaa aaa gag aag cct atg atg tct gtg acg gct ttg att caa    48
```

```
                                                      -continued

Met Met Lys Lys Glu Lys Pro Met Met Ser Val Thr Ala Leu Ile Gln
 1               5                  10                  15 gga gcc gct cag aat caa ata tgg gga cga gga tta tct ggc tta aca      96
Gly Ala Ala Gln Asn Gln Ile Trp Gly Arg Gly Leu Ser Gly Leu Thr
             20                  25                  30 ggc ttg gcc ctc gac caa ggg ctg tca atg agc tcg atg gga ccg ctc     144
Gly Leu Ala Leu Asp Gln Gly Leu Ser Met Ser Ser Met Gly Pro Leu
             35                  40                  45 tca ctg ccg gat atg aaa ccg gat cct gcg cta ctg aac ggc ggc ttt     192
Ser Leu Pro Asp Met Lys Pro Asp Pro Ala Leu Leu Asn Gly Gly Phe
 50                  55                  60 tcg ccc ggc agt ggc ggc gca gtt gtc ggc agt ccc gct agt ccg cct     240
Ser Pro Gly Ser Gly Gly Ala Val Val Gly Ser Pro Ala Ser Pro Pro
 65                  70                  75                  80 ttt ggt caa aat cac aca ata gta tca gga aac acg gcc acg ggc gcc     288
Phe Gly Gln Asn His Thr Ile Val Ser Gly Asn Thr Ala Thr Gly Ala
                 85                  90                  95 caa acg aaa tca cca tac cct cca aat cat cct ttg agc ggg tca aaa     336
Gln Thr Lys Ser Pro Tyr Pro Pro Asn His Pro Leu Ser Gly Ser Lys
            100                 105                 110 cat ctg tgc tcc ata tgc gga gat agg gct tcc ggg aag cat tat ggt     384
His Leu Cys Ser Ile Cys Gly Asp Arg Ala Ser Gly Lys His Tyr Gly
            115                 120                 125 gtt tac agt tgc gaa ggt tgt aag gga ttt ttc aaa cgg acg gta cga     432
Val Tyr Ser Cys Glu Gly Cys Lys Gly Phe Phe Lys Arg Thr Val Arg
        130                 135                 140 aaa gat ctg acg tat gcc tgt cga gag gat aga aat tgt ttg atc gac     480
Lys Asp Leu Thr Tyr Ala Cys Arg Glu Asp Arg Asn Cys Leu Ile Asp
145                 150                 155                 160 aaa agg cag aga aat cga tgt cag ttc tgt cga tat cag aaa tgt ctc     528
Lys Arg Gln Arg Asn Arg Cys Gln Phe Cys Arg Tyr Gln Lys Cys Leu
                165                 170                 175 gcc tgt gga atg aaa cga gaa gcc gtg cag gaa gaa cga caa cga gga     576
Ala Cys Gly Met Lys Arg Glu Ala Val Gln Glu Glu Arg Gln Arg Gly
            180                 185                 190 gca aag aat aat gaa gaa agc aac ccg aca agt tct gtt cgt gat tta     624
Ala Lys Asn Asn Glu Glu Ser Asn Pro Thr Ser Ser Val Arg Asp Leu
            195                 200                 205 acg gta gaa aga att tta gaa gca gaa caa agg agt gaa act cga aat     672
Thr Val Glu Arg Ile Leu Glu Ala Glu Gln Arg Ser Glu Thr Arg Asn
        210                 215                 220 gtt gcg acg gac ccg gaa ttg tcg ata caa tat ttg cga gta gga cct     720
Val Ala Thr Asp Pro Glu Leu Ser Ile Gln Tyr Leu Arg Val Gly Pro
225                 230                 235                 240 tca tcc atg gtg cct cct aga tac aag ggc cct gta tcc agt ctg tgt     768
Ser Ser Met Val Pro Pro Arg Tyr Lys Gly Pro Val Ser Ser Leu Cys
                245                 250                 255 cag caa gca aat aaa cag tta tat cag tta gta caa tac gca agg tgc     816
Gln Gln Ala Asn Lys Gln Leu Tyr Gln Leu Val Gln Tyr Ala Arg Cys
            260                 265                 270 atg ccg cat ttt agt gct tta caa tta gag gat caa gta acg tta ctc     864
Met Pro His Phe Ser Ala Leu Gln Leu Glu Asp Gln Val Thr Leu Leu
            275                 280                 285 aga gca gcc tgg aat gaa tta ctt ata gca tct ata gcc tgg aga agt     912
Arg Ala Ala Trp Asn Glu Leu Leu Ile Ala Ser Ile Ala Trp Arg Ser
        290                 295                 300 att gag tat cta gaa tcc gat gca gaa aca agt acg tcc agt atg tct     960
Ile Glu Tyr Leu Glu Ser Asp Ala Glu Thr Ser Thr Ser Ser Met Ser
305                 310                 315                 320
```

```
agt gat act tca aca agg aga cgc gct cca cca gga ccg cct gaa tta    1008
Ser Asp Thr Ser Thr Arg Arg Arg Ala Pro Pro Gly Pro Pro Glu Leu
                325                 330                 335 atg tgt ttc ttt cct ggt atg acg tta cat cgg aat agt gca atc cag    1056
Met Cys Phe Phe Pro Gly Met Thr Leu His Arg Asn Ser Ala Ile Gln
            340                 345                 350 gct ggc gtc gga cct att ttc gat cgg gta ctg tca gaa tta agt gtc    1104
Ala Gly Val Gly Pro Ile Phe Asp Arg Val Leu Ser Glu Leu Ser Val
        355                 360                 365 aaa atg aga aga atg gat ttg gac aga gca gaa tta ggc tgt ttg aag    1152
Lys Met Arg Arg Met Asp Leu Asp Arg Ala Glu Leu Gly Cys Leu Lys
    370                 375                 380 gct ata ata ctg ttt aat cct gat att cga gga ctg aaa tgt aga cag    1200
Ala Ile Ile Leu Phe Asn Pro Asp Ile Arg Gly Leu Lys Cys Arg Gln
385                 390                 395                 400 gaa gtg gat gct tta cga gaa aag gtt tac gcg tgc ctg gac gag cat    1248
Glu Val Asp Ala Leu Arg Glu Lys Val Tyr Ala Cys Leu Asp Glu His
                405                 410                 415 tgc agg acg cag cat cca gcg gaa gag ggt cgt ttc gca gcc ctg ctg    1296
Cys Arg Thr Gln His Pro Ala Glu Glu Gly Arg Phe Ala Ala Leu Leu
            420                 425                 430 ctt cgc ctg cca gct ctg agg tca atc tct ttg aaa tgt ctc gat cac    1344
Leu Arg Leu Pro Ala Leu Arg Ser Ile Ser Leu Lys Cys Leu Asp His
        435                 440                 445 ctg ttt ttc ttc aga ttg att ggc gat acg ccg ctt gag agt ttt ctt    1392
Leu Phe Phe Phe Arg Leu Ile Gly Asp Thr Pro Leu Glu Ser Phe Leu
    450                 455                 460 gtg gat tta ctc gag gcc gga ccg atc ggt                            1422
Val Asp Leu Leu Glu Ala Gly Pro Ile Gly
465                 470

<210> SEQ ID NO 36
<211> LENGTH: 474
<212> TYPE: PRT
<213> ORGANISM: Ctenocephalides felis

<400> SEQUENCE: 36

Met Met Lys Lys Glu Lys Pro Met Met Ser Val Thr Ala Leu Ile Gln
1               5                   10                  15

Gly Ala Ala Gln Asn Gln Ile Trp Gly Arg Gly Leu Ser Gly Leu Thr
            20                  25                  30

Gly Leu Ala Leu Asp Gln Gly Leu Ser Met Ser Ser Met Gly Pro Leu
        35                  40                  45

Ser Leu Pro Asp Met Lys Pro Asp Pro Ala Leu Leu Asn Gly Gly Phe
    50                  55                  60

Ser Pro Gly Ser Gly Gly Ala Val Val Gly Ser Pro Ala Ser Pro Pro
65                  70                  75                  80

Phe Gly Gln Asn His Thr Ile Val Ser Gly Asn Thr Ala Thr Gly Ala
                85                  90                  95

Gln Thr Lys Ser Pro Tyr Pro Asn His Pro Leu Ser Gly Ser Lys
            100                 105                 110

His Leu Cys Ser Ile Cys Gly Asp Arg Ala Ser Gly Lys His Tyr Gly
        115                 120                 125

Val Tyr Ser Cys Glu Gly Cys Lys Gly Phe Phe Lys Arg Thr Val Arg
    130                 135                 140

Lys Asp Leu Thr Tyr Ala Cys Arg Glu Asp Arg Asn Cys Leu Ile Asp
145                 150                 155                 160

Lys Arg Gln Arg Asn Arg Cys Gln Phe Cys Arg Tyr Gln Lys Cys Leu
```

|  | 165 |  |  | 170 |  |  | 175 |  |
|---|---|---|---|---|---|---|---|---|

Ala Cys Gly Met Lys Arg Glu Ala Val Gln Glu Arg Gln Arg Gly
            180                          185                          190

Ala Lys Asn Asn Glu Glu Ser Asn Pro Thr Ser Ser Val Arg Asp Leu
         195                          200                          205

Thr Val Glu Arg Ile Leu Glu Ala Glu Gln Arg Ser Glu Thr Arg Asn
         210                          215                          220

Val Ala Thr Asp Pro Glu Leu Ser Ile Gln Tyr Leu Arg Val Gly Pro
225                    230                       235                    240

Ser Ser Met Val Pro Pro Arg Tyr Lys Gly Pro Val Ser Ser Leu Cys
         245                          250                          255

Gln Gln Ala Asn Lys Gln Leu Tyr Gln Leu Val Gln Tyr Ala Arg Cys
         260                          265                          270

Met Pro His Phe Ser Ala Leu Gln Leu Glu Asp Gln Val Thr Leu Leu
         275                          280                          285

Arg Ala Ala Trp Asn Glu Leu Leu Ile Ala Ser Ile Ala Trp Arg Ser
         290                          295                          300

Ile Glu Tyr Leu Glu Ser Asp Ala Glu Thr Ser Thr Ser Ser Met Ser
305                    310                       315                    320

Ser Asp Thr Ser Thr Arg Arg Ala Pro Pro Gly Pro Pro Glu Leu
         325                          330                          335

Met Cys Phe Phe Pro Gly Met Thr Leu His Arg Asn Ser Ala Ile Gln
         340                          345                          350

Ala Gly Val Gly Pro Ile Phe Asp Arg Val Leu Ser Glu Leu Ser Val
         355                          360                          365

Lys Met Arg Arg Met Asp Leu Asp Arg Ala Glu Leu Gly Cys Leu Lys
         370                          375                          380

Ala Ile Ile Leu Phe Asn Pro Asp Ile Arg Gly Leu Lys Cys Arg Gln
385                    390                       395                    400

Glu Val Asp Ala Leu Arg Glu Lys Val Tyr Ala Cys Leu Asp Glu His
         405                          410                          415

Cys Arg Thr Gln His Pro Ala Glu Glu Gly Arg Phe Ala Ala Leu Leu
         420                          425                          430

Leu Arg Leu Pro Ala Leu Arg Ser Ile Ser Leu Lys Cys Leu Asp His
         435                          440                          445

Leu Phe Phe Phe Arg Leu Ile Gly Asp Thr Pro Leu Glu Ser Phe Leu
         450                          455                          460

Val Asp Leu Leu Glu Ala Gly Pro Ile Gly
465                    470

<210> SEQ ID NO 37
<211> LENGTH: 1422
<212> TYPE: DNA
<213> ORGANISM: Ctenocephalides felis

<400> SEQUENCE: 37

| accgatcggt | ccggcctcga | gtaaatccac | aagaaaactc | tcaagcggcg | tatcgccaat | 60 |
|---|---|---|---|---|---|---|
| caatctgaag | aaaaacaggt | gatcgagaca | tttcaaagag | attgacctca | gagctggcag | 120 |
| gcgaagcagc | agggctgcga | acgacccctc | ttccgctgga | tgctgcgtcc | tgcaatgctc | 180 |
| gtccaggcac | gcgtaaacct | ttctcgtaa | agcatccact | tcctgtctac | atttcagtcc | 240 |
| tcgaatatca | ggattaaaca | gtattatagc | cttcaaacag | cctaattctg | ctctgtccaa | 300 |
| atccattctt | ctcattttga | cacttaattc | tgacagtacc | cgatcgaaaa | taggtccgac | 360 |

-continued

```
gccagcctgg attgcactat tccgatgtaa cgtcatacca ggaaagaaac acattaattc      420
aggcggtcct ggtggagcgc gtctccttgt tgaagtatca ctagacatac tggacgtact      480
tgtttctgca tcggattcta gatactcaat acttctccag gctatagatg ctataagtaa      540
ttcattccag gctgctctga gtaacgttac ttgatcctct aattgtaaag cactaaaatg      600
cggcatgcac cttgcgtatt gtactaactg atataactgt ttatttgctt gctgacacag      660
actggataca gggcccttgt atctaggagg caccatggat gaaggtccta ctcgcaaata      720
ttgtatcgac aattccgggt ccgtcgcaac atttcgagtt tcactccttt gttctgcttc      780
taaaattctt tctaccgtta aatcacgaac agaacttgtc gggttgcttt cttcattatt      840
ctttgctcct cgttgtcgtt cttcctgcac ggcttctcgt ttcattccac aggcgagaca      900
tttctgatat cgacagaact gacatcgatt tctctgcctt tgtcgatca aacaatttct      960 atcctctcga caggcatacg tcagatcttt tcgtaccgtc cgtttgaaaa atcccttaca     1020
accttcgcaa ctgtaaacac cataatgctt cccggaagcc ctatctccgc atatggagca     1080
cagatgtttt gacccgctca aggatgatt tggagggtat ggtgatttcg tttgggcgcc      1140
cgtggccgtg tttcctgata ctattgtgtg atttgacca aaaggcggac tagcgggact      1200
gccgacaact gcgccgccac tgccgggcga aaagccgccg ttcagtagcg caggatccgg     1260
tttcatatcc ggcagtgaga gcggtcccat cgagctcatt gacagccctt ggtcgagggc     1320
caagcctgta aggccagata atcctcgtcc ccatatttga ttctgagcgg ctccttgaat     1380
caaagccgtc acagacatca taggcttctc tttttttcatc at                       1422
```

<210> SEQ ID NO 38
<211> LENGTH: 612
<212> TYPE: DNA
<213> ORGANISM: Ctenocephalides felis

<400> SEQUENCE: 38

```
tctgaggaag acctacgaag gataatgata agtacaccag ctgaagatga agctcttgaa       60
tttcggcata taactgaaat taccatactt actgtgcagc ttatagtgga atttgcaaag      120
ggtttaccag cttttaccaa aataccacaa gaagatcaaa taacattatt aaaggcatgt      180
tcaagtgaag taatgatgct gcgaatggct cggcggtacg atgcagtgtc ggattcaatc      240
ttattcgcga ataatcgttc atatactcgt gactcctata aaatggctgg tatggcagat      300
acaatagaag atctattgca ttttttgtcga cagatgtata ctatgactgt agacaatgtg      360
gagtatgcac taataacagc aattgtgatt ttttcagatc gacctggatt ggaacaagca      420
gatcttgtgg aacaaattca aagttattac atcaaaacat taaagtgcta cattttgaat      480
cgacatagtg gtgaccctaa gtgtggaata ttgtttgcca aacttctttc tattcttact      540
gaattacgca cgttaggaaa tcaaaactca gaaatgtgtt ttgcactgaa attgaagaac      600
agaaaacttc ct                                                          612
```

<210> SEQ ID NO 39
<211> LENGTH: 612
<212> TYPE: DNA
<213> ORGANISM: Ctenocephalides felis

<400> SEQUENCE: 39

```
aggaagtttt ctgttcttca atttcagtgc aaaacacatt tctgagtttt gatttcctaa       60
cgtgcgtaat tcagtaagaa tagaaagaag tttggcaaac aatattccac acttagggtc      120
accactatgt cgattcaaaa tgtagcactt taatgttttg atgtaataac tttgaatttg      180
```

```
ttccacaaga tctgcttgtt ccaatccagg tcgatctgaa aaaatcacaa ttgctgttat      240
tagtgcatac tccacattgt ctacagtcat agtatacatc tgtcgacaaa aatgcaatag      300
atcttctatt gtatctgcca taccagccat tttataggag tcacgagtat atgaacgatt      360
attcgcgaat aagattgaat ccgacactgc atcgtaccgc cgagccattc gcagcatcat      420
tacttcactt gaacatgcct ttaataatgt tatttgatct tcttgtggta ttttggtaaa      480
agctggtaaa ccctttgcaa attccactat aagctgcaca gtaagtatgg taatttcagt      540
tatatgccga aattcaagag cttcatcttc agctggtgta cttatcatta tccttcgtag      600
gtcttcctca ga                                                         612

<210> SEQ ID NO 40
<211> LENGTH: 776
<212> TYPE: DNA
<213> ORGANISM: Ctenocephalides felis

<400> SEQUENCE: 40
gaaagaattt tagaagcaga acaaaggagt gaaactcgaa atgttgcgac ggacccggaa       60
ttgtcgatac aatatttgcg agtaggacct tcatccatgg tgcctcctag atacaagggc      120
cctgtatcca gtctgtgtca gcaagcaaat aaacagttat atcagttagt acaatacgca      180
aggtgcatgc cgcattttag tgctttacaa ttagaggatc aagtaacgtt actcagagca      240
gcctggaatg aattacttat agcatctata gcctggagaa gtattgagta tctagaatcc      300
gatgcagaaa caagtacgtc cagtatgtct agtgatactt caacaaggag acgcgctcca      360
ccaggaccgc ctgaattaat gtgtttcttt cctggtatga cgttacatcg aatagtgca       420 atccaggctg gcgtcggacc tatttttcgat cgggtactgt cagaattaag tgtcaaaatg     480
agaagaatgg atttggacag agcagaatta ggctgtttga aggctataat actgtttaat     540
cctgatattc gaggactgaa atgtagacag gaagtggatg ctttacgaga aaaggtttac     600
gcgtgcctgg acgagcattg caggacgcag catccagcgg aagagggtcg tttcgcagcc      660
ctgctgcttc gcctgccagc tctgaggtca atctctttga aatgtctcga tcacctgttt      720
ttcttcagat tgattggcga tacgccgctt gagagttttc ttgtggattt actcga          776

<210> SEQ ID NO 41
<211> LENGTH: 776
<212> TYPE: DNA
<213> ORGANISM: Ctenocephalides felis

<400> SEQUENCE: 41
tcgagtaaat ccacaagaaa actctcaagc ggcgtatcgc caatcaatct gaagaaaaac       60
aggtgatcga gacatttcaa agagattgac ctcagagctg gcaggcgaag cagcagggct      120
gcgaaacgac cctcttccgc tggatgctgc gtcctgcaat gctcgtccag gcacgcgtaa      180
accttttctc gtaaagcatc cacttcctgt ctacatttca gtcctcgaat atcaggatta      240
aacagtatta tagccttcaa acagcctaat tctgctctgt ccaaatccat tcttctcatt      300
ttgacactta attctgacag tacccgatcg aaaataggtc cgacgccagc ctggattgca      360
ctattccgat gtaacgtcat accaggaaag aaacacatta attcaggcgg tcctggtgga      420
gcgcgtctcc ttgttgaagt atcactagac atactggacg tacttgtttc tgcatcggat      480
tctagatact caatacttct ccaggctata gatgctataa gtaattcatt ccaggctgct      540
ctgagtaacg ttacttgatc ctctaattgt aaagcactaa aatgcggcat gcaccttgcg      600
```

```
tattgtacta actgatataa ctgtttattt gcttgctgac acagactgga tacagggccc      660
ttgtatctag gaggcaccat ggatgaaggt cctactcgca aatattgtat cgacaattcc      720
gggtccgtcg caacatttcg agtttcactc ctttgttctg cttctaaaat tctttc         776
```

<210> SEQ ID NO 42
<211> LENGTH: 943
<212> TYPE: DNA
<213> ORGANISM: Ctenocephalides felis

<400> SEQUENCE: 42

```
gaggtatata ttaatgtatc gattaaataa ggaggaataa accatggggg gttctcatca       60
tcatcatcat catggtatgg ctagcatgac tggtggacag caaatgggtc gggatctgta      120
cgacgatgac gataaggatc cctctgttcg agatttaacg gtagaaagaa ttttagaagc      180
ggaacaaagg agtgaaactc gaaatgttgc gacggacccg aattgtcga tacaatattt       240 gcgagtagga ccttcatcca tggtgcctcc tagatacaag ggcctgtat ccagtctgtg       300 tcagcaagca aataaacagt tatatcagtt agtacaatac gcaaggtgca tgccgcattt      360
tagtgcttta caattagagg atcaagtaac gttactcaga gcagcctgga atgaattact      420
tatagcatct atagcctgga gaagtattga gtatctagaa tccgatgcag aaacaagtac      480
gtccagtatg tctagtgata cttcaacaag gagacgcgct ccaccaggac cgcctgaatt      540
aatgtgtttc cttcctggta tgacgttaca tcggaatagt gcaatccagg ctggcgtcgg      600
acctaatttc gatcgggtac tgtcagaatt aagtgtcaaa atgagaagaa tggatttgga      660
cagagcagaa ttaggctgtt tgaaggctat aatactgttt aatcctgata ttcgaggact      720
gaaatgtaga caggaagtgg atgctttacg agaaaaggtt tacgcgtgcc tggacgagca      780
ttgcaggacg cagcatccag cggaagaggg tcgtttcgca gccctgctgc ttcgcctgcc      840
agctctgagg tcaatctctt tgaaatgtct cgatcacctg ttttcttca gattgattgg       900 cgatacgccg cttgagagtt tcttgtgga tttactcgag gcc                         943
```

<210> SEQ ID NO 43
<211> LENGTH: 943
<212> TYPE: DNA
<213> ORGANISM: Ctenocephalides felis

<400> SEQUENCE: 43

```
ggcctcgagt aaatccacaa gaaaactctc aagcggcgta tcgccaatca atctgaagaa       60
aaacaggtga tcgagacatt tcaaagagat tgacctcaga gctggcaggc gaagcagcag      120
ggctgcgaaa cgaccctctt ccgctggatg ctgcgtcctg caatgctcgt ccaggcacgc      180
gtaaaccttt tctcgtaaag catccacttc ctgtctacat ttcagtcctc gaatatcagg      240
attaaacagt attatagcct tcaaacagcc taattctgct ctgtccaaat ccattcttct      300
cattttgaca cttaattctg acagtacccg atcgaaatta gtccgacgc cagcctggat      360 tgcactattc cgatgtaacg tcataccagg aaggaaacac attaattcag gcggtcctgg      420
tggagcgcgt ctccttgttg aagtatcact agacatactg gacgtacttg tttctgcatc      480
ggattctaga tactcaatac ttctccaggc tatagatgct ataagtaatt cattccaggc      540
tgctctgagt aacgttactt gatcctctaa ttgtaaagca ctaaaatgcg gcatgcacct      600
tgcgtattgt actaactgat ataactgttt atttgcttgc tgacacagac tggatacagg      660
gcccttgtat ctaggaggca ccatggatga aggtcctact cgcaaatatt gtatcgacaa      720
ttccgggtcc gtcgcaacat ttcgagtttc actcctttgt tccgcttcta aaattctttc      780
```

```
taccgttaaa tctcgaacag agggatcctt atcgtcatcg tcgtacagat cccgacccat      840
ttgctgtcca ccagtcatgc tagccatacc atgatgatga tgatgatgag aacccccat      900 ggtttattcc tccttattta atcgatacat taatatatac ctc                       943
```

```
<210> SEQ ID NO 44
<211> LENGTH: 21
<212> TYPE: DNA
<213> ORGANISM: Artificial
<220> FEATURE:
<223> OTHER INFORMATION: Synthetic Primer

<400> SEQUENCE: 44
tgygaaatgg ayatgtayat g                                                21

<210> SEQ ID NO 45
<211> LENGTH: 20
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (15)..(15)
<223> OTHER INFORMATION: n = unknown

<400> SEQUENCE: 45
ccyttwgcra attcnacdat                                                  20

<210> SEQ ID NO 46
<211> LENGTH: 18
<212> TYPE: DNA
<213> ORGANISM: Artificial
<220> FEATURE:
<223> OTHER INFORMATION: Synthetic Primer

<400> SEQUENCE: 46
ggttcccgaa aaccaatg                                                    18

<210> SEQ ID NO 47
<211> LENGTH: 19
<212> TYPE: DNA
<213> ORGANISM: Artificial
<220> FEATURE:
<223> OTHER INFORMATION: Synthetic Primer

<400> SEQUENCE: 47
gccgaaattc aagagcttc                                                   19

<210> SEQ ID NO 48
<211> LENGTH: 18
<212> TYPE: DNA
<213> ORGANISM: Artificial
<220> FEATURE:
<223> OTHER INFORMATION: Synthetic Primer

<400> SEQUENCE: 48
gtcaggaatg taggctca                                                    18

<210> SEQ ID NO 49
<211> LENGTH: 20
<212> TYPE: DNA
<213> ORGANISM: Artificial
<220> FEATURE:
<223> OTHER INFORMATION: Synthetic Primer
```

```
<400> SEQUENCE: 49
aattaaccct cactaaaggg                                              20

<210> SEQ ID NO 50
<211> LENGTH: 20
<212> TYPE: DNA
<213> ORGANISM: Artificial
<220> FEATURE:
<223> OTHER INFORMATION: Synthetic Primer

<400> SEQUENCE: 50
ggwaaacayt atggwgtwta                                              20

<210> SEQ ID NO 51
<211> LENGTH: 18
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (10)..(10)
<223> OTHER INFORMATION: n = unknown

<400> SEQUENCE: 51
ttcttcytgn acwhcttc                                                18

<210> SEQ ID NO 52
<211> LENGTH: 20
<212> TYPE: DNA
<213> ORGANISM: Artificial
<220> FEATURE:
<223> OTHER INFORMATION: Synthetic Primer

<400> SEQUENCE: 52
ttctcgtttc attccacagg                                              20

<210> SEQ ID NO 53
<211> LENGTH: 29
<212> TYPE: DNA
<213> ORGANISM: Artificial
<220> FEATURE:
<223> OTHER INFORMATION: Synthetic Primer

<400> SEQUENCE: 53
aaagggaaca aaagctggag ctccaccgc                                    29

<210> SEQ ID NO 54
<211> LENGTH: 28
<212> TYPE: DNA
<213> ORGANISM: Artificial
<220> FEATURE:
<223> OTHER INFORMATION: Synthetic Primer

<400> SEQUENCE: 54
ttaaaatatc actggttcgt atcctccc                                     28

<210> SEQ ID NO 55
<211> LENGTH: 26
<212> TYPE: DNA
<213> ORGANISM: Artificial
<220> FEATURE:
<223> OTHER INFORMATION: Synthetic Primer

<400> SEQUENCE: 55
ggcggccgct ctagaactag tggatc                                       26
```

<210> SEQ ID NO 56
<211> LENGTH: 23
<212> TYPE: DNA
<213> ORGANISM: Artificial
<220> FEATURE:
<223> OTHER INFORMATION: Synthetic Primer

<400> SEQUENCE: 56
agacaatcaa tatcccaagt gcg                                       23

<210> SEQ ID NO 57
<211> LENGTH: 27
<212> TYPE: DNA
<213> ORGANISM: Artificial
<220> FEATURE:
<223> OTHER INFORMATION: Synthetic Primer

<400> SEQUENCE: 57
ctgcataaaa tgcctaaagt cgcggac                                   27

<210> SEQ ID NO 58
<211> LENGTH: 30
<212> TYPE: DNA
<213> ORGANISM: Artificial
<220> FEATURE:
<223> OTHER INFORMATION: Synthetic Primer

<400> SEQUENCE: 58
gcgggatccc aagatggata tgaacaacct                                30

<210> SEQ ID NO 59
<211> LENGTH: 36
<212> TYPE: DNA
<213> ORGANISM: Artificial
<220> FEATURE:
<223> OTHER INFORMATION: Synthetic Primer

<400> SEQUENCE: 59
gcggaattct caatcccaaa tttcttctaa aaatct                         36

<210> SEQ ID NO 60
<211> LENGTH: 31
<212> TYPE: DNA
<213> ORGANISM: Artificial
<220> FEATURE:
<223> OTHER INFORMATION: Synthetic Primer

<400> SEQUENCE: 60
gcgggatccc tctgttcgag atttaacggt a                              31

<210> SEQ ID NO 61
<211> LENGTH: 27
<212> TYPE: DNA
<213> ORGANISM: Artificial
<220> FEATURE:
<223> OTHER INFORMATION: Synthetic Primer

<400> SEQUENCE: 61
gcgaagcttt caaccgatgg gtccgcc                                   27

<210> SEQ ID NO 62
<211> LENGTH: 36
<212> TYPE: DNA
<213> ORGANISM: Artificial
<220> FEATURE:

<223> OTHER INFORMATION: Synthetic Primer

<400> SEQUENCE: 62
gcgcccgggg gattaacttt attattaaaa attaaa          36

<210> SEQ ID NO 63
<211> LENGTH: 33
<212> TYPE: DNA
<213> ORGANISM: Artificial
<220> FEATURE:
<223> OTHER INFORMATION: Synthetic Primer

<400> SEQUENCE: 63
gcgcgcggcc gcaagctttc aaccgatggg tcc          33

<210> SEQ ID NO 64
<211> LENGTH: 66
<212> TYPE: PRT
<213> ORGANISM: Ctenocephalides felis

<400> SEQUENCE: 64

Cys Leu Val Cys Gly Asp Arg Ala Ser Gly Tyr His Tyr Asn Ala Leu
1               5                   10                  15

Thr Cys Glu Gly Cys Lys Gly Phe Phe Arg Arg Ser Val Thr Lys Asn
            20                  25                  30

Ala Val Tyr Val Cys Lys Phe Gly His Thr Cys Glu Met Asp Met Tyr
        35                  40                  45

Met Arg Arg Lys Cys Gln Glu Cys Arg Leu Lys Lys Cys Leu Ala Val
    50                  55                  60

Gly Met
65

<210> SEQ ID NO 65
<211> LENGTH: 219
<212> TYPE: PRT
<213> ORGANISM: Ctenocephalides felis

<400> SEQUENCE: 65

Gln Asp Gly Tyr Glu Gln Pro Ser Glu Glu Asp Leu Arg Arg Ile Met
1               5                   10                  15

Ile Ser Thr Pro Ala Glu Asp Glu Ala Leu Glu Phe Arg His Ile Thr
            20                  25                  30

Glu Ile Thr Ile Leu Thr Val Gln Leu Ile Val Glu Phe Ala Lys Gly
        35                  40                  45

Leu Pro Ala Phe Thr Lys Ile Pro Gln Glu Asp Gln Ile Thr Leu Leu
    50                  55                  60

Lys Ala Cys Ser Ser Glu Val Met Met Leu Arg Met Ala Arg Arg Tyr
65                  70                  75                  80

Asp Ala Val Ser Asp Ser Ile Leu Phe Ala Asn Asn Arg Ser Tyr Thr
                85                  90                  95

Arg Asp Ser Tyr Lys Met Ala Gly Met Ala Asp Thr Ile Glu Asp Leu
            100                 105                 110

Leu His Phe Cys Arg Gln Met Tyr Thr Met Thr Val Asp Asn Val Glu
        115                 120                 125

Tyr Ala Leu Ile Thr Ala Ile Val Ile Phe Ser Asp Arg Pro Gly Leu
    130                 135                 140

Glu Gln Ala Asp Leu Val Glu Gln Ile Gln Ser Tyr Tyr Ile Lys Thr
145                 150                 155                 160

```
Leu Lys Cys Tyr Ile Leu Asn Arg His Ser Gly Asp Pro Lys Cys Gly
            165                 170                 175

Ile Leu Phe Ala Lys Leu Leu Ser Ile Leu Thr Glu Leu Arg Thr Leu
            180                 185                 190

Gly Asn Gln Asn Ser Glu Met Cys Phe Ala Leu Lys Leu Lys Asn Arg
            195                 200                 205

Lys Leu Pro Arg Phe Leu Glu Glu Ile Trp Asp
    210                 215

<210> SEQ ID NO 66
<211> LENGTH: 66
<212> TYPE: PRT
<213> ORGANISM: Ctenocephalides felis

<400> SEQUENCE: 66

Cys Leu Val Cys Gly Asp Arg Ala Ser Gly Tyr His Tyr Asn Ala Leu
1               5                   10                  15

Thr Cys Glu Gly Cys Lys Gly Phe Phe Arg Arg Ser Val Thr Lys Asn
            20                  25                  30

Ala Val Tyr Val Cys Lys Phe Gly His Thr Cys Glu Met Asp Met Tyr
            35                  40                  45

Met Arg Arg Lys Cys Gln Glu Cys Arg Leu Lys Lys Cys Leu Ala Val
        50                  55                  60

Gly Met
65

<210> SEQ ID NO 67
<211> LENGTH: 219
<212> TYPE: PRT
<213> ORGANISM: Ctenocephalides felis

<400> SEQUENCE: 67

Gln Asp Gly Tyr Glu Gln Pro Ser Glu Glu Asp Leu Arg Arg Ile Met
1               5                   10                  15

Ile Ser Thr Pro Ala Glu Asp Glu Ala Leu Glu Phe Arg His Ile Thr
            20                  25                  30

Glu Ile Thr Ile Leu Thr Val Gln Leu Ile Val Glu Phe Ala Lys Gly
            35                  40                  45

Leu Pro Ala Phe Thr Lys Ile Pro Gln Glu Asp Gln Ile Thr Leu Leu
        50                  55                  60

Lys Ala Cys Ser Ser Glu Val Met Met Leu Arg Met Ala Arg Arg Tyr
65                  70                  75                  80

Asp Ala Val Ser Asp Ser Ile Leu Phe Ala Asn Asn Arg Ser Tyr Thr
            85                  90                  95

Arg Asp Ser Tyr Lys Met Ala Gly Met Ala Asp Thr Ile Glu Asp Leu
            100                 105                 110

Leu His Phe Cys Arg Gln Met Tyr Thr Met Thr Val Asp Asn Val Glu
            115                 120                 125

Tyr Ala Leu Ile Thr Ala Ile Val Ile Phe Ser Asp Arg Pro Gly Leu
        130                 135                 140

Glu Gln Ala Asp Leu Val Glu Gln Ile Gln Ser Tyr Tyr Ile Lys Thr
145                 150                 155                 160

Leu Lys Cys Tyr Ile Leu Asn Arg His Ser Gly Asp Pro Lys Cys Gly
            165                 170                 175

Ile Leu Phe Ala Lys Leu Leu Ser Ile Leu Thr Glu Leu Arg Thr Leu
            180                 185                 190
```

```
Gly Asn Gln Asn Ser Glu Met Cys Phe Ala Leu Lys Leu Lys Asn Arg
            195                 200                 205

Lys Leu Pro Arg Phe Leu Glu Glu Ile Trp Asp
    210                 215

<210> SEQ ID NO 68
<211> LENGTH: 66
<212> TYPE: PRT
<213> ORGANISM: Ctenocephalides felis

<400> SEQUENCE: 68

Cys Ser Ile Cys Gly Asp Arg Ala Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30

Leu Thr Tyr Ala Cys Arg Glu Asp Arg Asn Cys Leu Ile Asp Lys Arg
        35                  40                  45

Gln Arg Asn Arg Cys Gln Phe Cys Arg Tyr Gln Lys Cys Leu Ala Cys
    50                  55                  60

Gly Met
65

<210> SEQ ID NO 69
<211> LENGTH: 271
<212> TYPE: PRT
<213> ORGANISM: Ctenocephalides felis

<400> SEQUENCE: 69

Ser Val Arg Asp Leu Thr Val Glu Arg Ile Leu Glu Ala Glu Gln Arg
1               5                   10                  15

Ser Glu Thr Arg Asn Val Ala Thr Asp Pro Glu Leu Ser Ile Gln Tyr
            20                  25                  30

Leu Arg Val Gly Pro Ser Ser Met Val Pro Arg Tyr Lys Gly Pro
        35                  40                  45

Val Ser Ser Leu Cys Gln Gln Ala Asn Lys Gln Leu Tyr Gln Leu Val
    50                  55                  60

Gln Tyr Ala Arg Cys Met Pro His Phe Ser Ala Leu Gln Leu Glu Asp
65              70                  75                  80

Gln Val Thr Leu Leu Arg Ala Ala Trp Asn Glu Leu Leu Ile Ala Ser
            85                  90                  95

Ile Ala Trp Arg Ser Ile Glu Tyr Leu Glu Ser Asp Ala Glu Thr Ser
            100                 105                 110

Thr Ser Ser Met Ser Ser Asp Thr Ser Thr Arg Arg Arg Ala Pro Pro
        115                 120                 125

Gly Pro Pro Glu Leu Met Cys Phe Phe Pro Gly Met Thr Leu His Arg
    130                 135                 140

Asn Ser Ala Ile Gln Ala Gly Val Gly Pro Ile Phe Asp Arg Val Leu
145                 150                 155                 160

Ser Glu Leu Ser Val Lys Met Arg Arg Met Asp Leu Asp Arg Ala Glu
            165                 170                 175

Leu Gly Cys Leu Lys Ala Ile Ile Leu Phe Asn Pro Asp Ile Arg Gly
        180                 185                 190

Leu Lys Cys Arg Gln Glu Val Asp Ala Leu Arg Glu Lys Val Tyr Ala
    195                 200                 205

Cys Leu Asp Glu His Cys Arg Thr Gln His Pro Ala Glu Glu Gly Arg
    210                 215                 220
```

```
Phe Ala Ala Leu Leu Leu Arg Leu Pro Ala Leu Arg Ser Ile Ser Leu
225                 230                 235                 240

Lys Cys Leu Asp His Leu Phe Phe Arg Leu Ile Gly Asp Thr Pro
            245                 250                 255

Leu Glu Ser Phe Leu Val Asp Leu Leu Glu Ala Gly Pro Ile Gly
        260                 265                 270
```

<210> SEQ ID NO 70
<211> LENGTH: 66
<212> TYPE: PRT
<213> ORGANISM: Ctenocephalides felis

<400> SEQUENCE: 70

```
Cys Ser Ile Cys Gly Asp Arg Ala Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30

Leu Thr Tyr Ala Cys Arg Glu Asp Arg Asn Cys Leu Ile Asp Lys Arg
        35                  40                  45

Gln Arg Asn Arg Cys Gln Phe Cys Arg Tyr Gln Lys Cys Leu Ala Cys
    50                  55                  60

Gly Met
65
```

<210> SEQ ID NO 71
<211> LENGTH: 271
<212> TYPE: PRT
<213> ORGANISM: Ctenocephalides felis

<400> SEQUENCE: 71

```
Ser Val Arg Asp Leu Thr Val Glu Arg Ile Leu Glu Ala Glu Gln Arg
1               5                   10                  15

Ser Glu Thr Arg Asn Val Ala Thr Asp Pro Glu Leu Ser Ile Gln Tyr
            20                  25                  30

Leu Arg Val Gly Pro Ser Ser Met Val Pro Arg Tyr Lys Gly Pro
        35                  40                  45

Val Ser Ser Leu Cys Gln Gln Ala Asn Lys Gln Leu Tyr Gln Leu Val
    50                  55                  60

Gln Tyr Ala Arg Cys Met Pro His Phe Ser Ala Leu Gln Leu Glu Asp
65                  70                  75                  80

Gln Val Thr Leu Leu Arg Ala Ala Trp Asn Glu Leu Leu Ile Ala Ser
            85                  90                  95

Ile Ala Trp Arg Ser Ile Glu Tyr Leu Glu Ser Asp Ala Glu Thr Ser
        100                 105                 110

Thr Ser Ser Met Ser Ser Asp Thr Ser Thr Arg Arg Ala Pro Pro
    115                 120                 125

Gly Pro Pro Glu Leu Met Cys Phe Phe Pro Gly Met Thr Leu His Arg
        130                 135                 140

Asn Ser Ala Ile Gln Ala Gly Val Gly Pro Ile Phe Asp Arg Val Leu
145                 150                 155                 160

Ser Glu Leu Ser Val Lys Met Arg Arg Met Asp Leu Asp Arg Ala Glu
            165                 170                 175

Leu Gly Cys Leu Lys Ala Ile Ile Leu Phe Asn Pro Asp Ile Arg Gly
        180                 185                 190

Leu Lys Cys Arg Gln Glu Val Asp Ala Leu Arg Glu Lys Val Tyr Ala
    195                 200                 205
```

```
Cys Leu Asp Glu His Cys Arg Thr Gln His Pro Ala Glu Glu Gly Arg
        210                 215                 220

Phe Ala Ala Leu Leu Leu Arg Leu Pro Ala Leu Arg Ser Ile Ser Leu
225                 230                 235                 240

Lys Cys Leu Asp His Leu Phe Phe Phe Arg Leu Ile Gly Asp Thr Pro
                    245                 250                 255

Leu Glu Ser Phe Leu Val Asp Leu Leu Glu Ala Gly Pro Ile Gly
            260                 265                 270

<210> SEQ ID NO 72
<211> LENGTH: 461
<212> TYPE: PRT
<213> ORGANISM: Manduca sexta

<400> SEQUENCE: 72

Met Ser Ser Val Ala Lys Lys Asp Lys Arg Thr Met Ser Val Thr Ala
1               5                   10                  15

Leu Ile Asn Arg Ala Trp Pro Leu Thr Pro Ala Pro His Gln Gln Gln
            20                  25                  30

Ser Met Pro Ser Ser Gln Pro Ser Asn Phe Leu Gln Pro Leu Ala Thr
        35                  40                  45

Pro Ser Thr Thr Pro Ser Val Glu Leu Asp Ile Gln Trp Leu Asn Ile
50                  55                  60

Glu Pro Gly Phe Met Ser Pro Met Ser Pro Glu Met Lys Pro Asp
65                  70                  75                  80

Thr Ala Met Leu Asp Gly Leu Arg Asp Ser Thr Pro Pro Ala
                85                  90                  95

Phe Lys Asn Tyr Pro Pro Asn His Pro Leu Ser Gly Ser Lys His Leu
                100                 105                 110

Cys Ser Ile Cys Gly Asp Arg Ala Ser Gly Lys His Tyr Gly Val Tyr
            115                 120                 125

Ser Cys Glu Gly Cys Lys Gly Phe Phe Lys Arg Thr Val Arg Lys Asp
        130                 135                 140

Leu Thr Tyr Ala Cys Arg Glu Asp Arg Asn Cys Ile Ile Asp Lys Arg
145                 150                 155                 160

Gln Arg Asn Arg Cys Gln Tyr Cys Arg Tyr Gln Lys Cys Leu Ala Cys
                165                 170                 175

Gly Met Lys Arg Glu Ala Val Gln Glu Glu Arg Gln Arg Ala Ala Arg
            180                 185                 190

Gly Thr Glu Asp Ala His Pro Ser Ser Ser Val Gln Glu Leu Ser Ile
        195                 200                 205

Glu Arg Leu Leu Glu Ile Glu Ser Leu Val Ala Asp Pro Pro Glu Glu
210                 215                 220

Phe Gln Phe Leu Arg Val Gly Pro Glu Ser Gly Val Pro Ala Lys Tyr
225                 230                 235                 240

Arg Ala Pro Val Ser Ser Leu Cys Gln Ile Gly Asn Lys Gln Ile Ala
                245                 250                 255

Ala Leu Val Val Trp Ala Arg Asp Ile Pro His Phe Gly Gln Leu Glu
            260                 265                 270

Leu Glu Asp Gln Ile Leu Leu Ile Lys Asn Ser Trp Asn Glu Leu Leu
        275                 280                 285

Leu Phe Ala Ile Ala Trp Arg Ser Met Glu Tyr Leu Thr Asp Glu Arg
290                 295                 300

Glu Asn Val Asp Ser Arg Ser Thr Ala Pro Pro Gln Leu Met Cys Leu
305                 310                 315                 320
```

```
Met Pro Gly Met Thr Leu His Arg Asn Ser Ala Leu Gln Ala Gly Val
            325                 330                 335

Gly Gln Ile Phe Asp Arg Val Leu Ser Glu Leu Ser Leu Lys Met Arg
        340                 345                 350

Thr Leu Arg Met Asp Gln Ala Glu Tyr Val Ala Leu Lys Ala Ile Ile
            355                 360                 365

Leu Leu Asn Pro Asp Val Lys Gly Leu Lys Asn Lys Pro Glu Val Val
        370                 375                 380

Val Leu Arg Glu Lys Met Phe Ser Cys Leu Asp Glu Tyr Val Arg Arg
385                 390                 395                 400

Ser Arg Cys Ala Glu Glu Gly Arg Phe Ala Ala Leu Leu Leu Arg Leu
                405                 410                 415

Pro Ala Leu Arg Ser Ile Ser Leu Lys Cys Phe Glu His Leu Tyr Phe
            420                 425                 430

Phe His Leu Val Ala Asp Thr Ser Ile Ala Ser Tyr Ile His Asp Ala
        435                 440                 445

Leu Arg Asn His Ala Pro Ser Ile Asp Thr Ser Ile Leu
        450                 455                 460

<210> SEQ ID NO 73
<211> LENGTH: 463
<212> TYPE: PRT
<213> ORGANISM: Homo sapiens

<400> SEQUENCE: 73

Met Tyr Gly Asn Tyr Ser His Phe Met Lys Phe Pro Ala Gly Tyr Gly
1               5                   10                  15

Gly Ser Pro Gly His Thr Gly Ser Thr Ser Met Ser Pro Ser Ala Ala
            20                  25                  30

Leu Ser Thr Gly Lys Pro Met Asp Ser His Pro Ser Tyr Thr Asp Thr
        35                  40                  45

Pro Val Ser Ala Pro Arg Thr Leu Ser Ala Val Gly Thr Pro Leu Asn
    50                  55                  60

Ala Leu Gly Ser Pro Tyr Arg Val Ile Thr Ser Ala Met Gly Pro Pro
65                  70                  75                  80

Ser Gly Ala Leu Ala Ala Pro Gly Ile Asn Leu Val Ala Pro Pro
                85                  90                  95

Ser Ser Gln Leu Asn Val Val Asn Ser Val Ser Ser Glu Asp Ile
            100                 105                 110

Lys Pro Leu Pro Gly Leu Pro Gly Ile Gly Asn Met Asn Tyr Pro Ser
        115                 120                 125

Thr Ser Pro Gly Ser Leu Val Lys His Ile Cys Ala Ile Cys Gly Asp
    130                 135                 140

Arg Ser Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
            180                 185                 190

Tyr Cys Arg Tyr Gln Lys Cys Leu Val Met Gly Met Lys Arg Glu Ala
        195                 200                 205

Val Gln Glu Glu Arg Gln Arg Ser Arg Glu Arg Ala Glu Ser Glu Ala
    210                 215                 220

Glu Cys Ala Thr Ser Gly His Glu Asp Met Pro Val Glu Arg Ile Leu
```

-continued

```
                225                 230                 235                 240

Glu Ala Glu Leu Ala Val Glu Pro Lys Thr Glu Ser Tyr Gly Asp Met
                245                 250                 255

Asn Met Glu Asn Ser Thr Asn Asp Pro Val Thr Asn Ile Cys His Ala
            260                 265                 270

Ala Asp Lys Gln Leu Phe Thr Leu Val Glu Trp Ala Lys Arg Ile Pro
        275                 280                 285

His Phe Ser Asp Leu Thr Leu Glu Asp Gln Val Ile Leu Leu Arg Ala
    290                 295                 300

Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
                325                 330                 335

Ser Ala His Ser Ala Gly Val Gly Ser Ile Phe Asp Arg Val Leu Thr
            340                 345                 350

Glu Leu Val Ser Lys Met Lys Asp Met Gln Met Asp Lys Ser Glu Leu
        355                 360                 365

Gly Cys Leu Arg Ala Ile Val Leu Phe Asn Pro Asp Ala Lys Gly Leu
    370                 375                 380

Ser Asn Pro Ser Glu Val Glu Thr Leu Arg Glu Lys Val Tyr Ala Thr
385                 390                 395                 400

Leu Glu Ala Tyr Thr Lys Gln Lys Tyr Pro Glu Gln Pro Gly Arg Phe
                405                 410                 415

Ala Lys Leu Leu Leu Arg Leu Pro Ala Leu Arg Ser Ile Gly Leu Lys
            420                 425                 430

Cys Leu Glu His Leu Phe Phe Phe Lys Leu Ile Gly Asp Thr Pro Ile
        435                 440                 445

Asp Thr Phe Leu Met Glu Met Leu Glu Thr Pro Leu Gln Ile Thr
    450                 455                 460

<210> SEQ ID NO 74
<211> LENGTH: 232
<212> TYPE: DNA
<213> ORGANISM: Mus musculus

<400> SEQUENCE: 74
cggtttcaga gcacatgcat gttgtcaggg ccagcctgct ccgccgctcg ctaagctgtt      60
actccgagct acctgctggg gaattcacct ccacgtagcc cggggtgtct cctcccatc     120 ccagagtcag aaaagttgtc ctctctaaca ccaaagagga gaattcactt tctgggaaca     180
agtgcaagac actgacacgc aaggacgtga taaattccta gaaagataaa at            232

<210> SEQ ID NO 75
<211> LENGTH: 878
<212> TYPE: PRT
<213> ORGANISM: Drosophila melanogaster

<400> SEQUENCE: 75

Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Gln Asp Leu Trp Leu Cys Gly Asn Glu Ser Gly Ser Phe Gly Gly
    50                  55                  60
```

```
Ser Asn Gly His Gly Leu Ser Gln Gln Gln Ser Val Ile Thr Leu
 65                  70                  75                  80

Ala Met His Gly Cys Ser Ser Thr Leu Pro Ala Gln Thr Thr Ile Ile
                 85                  90                  95

Pro Ile Asn Gly Asn Ala Asn Gly Asn Gly Gly Ser Thr Asn Gly Gln
            100                 105                 110

Tyr Val Pro Gly Ala Thr Asn Leu Gly Ala Leu Ala Asn Gly Met Leu
            115                 120                 125

Asn Gly Gly Phe Asn Gly Met Gln Gln Gln Ile Gln Asn Gly His Gly
        130                 135                 140

Leu Ile Asn Ser Thr Thr Pro Ser Thr Pro Thr Thr Pro Leu His Leu
145                 150                 155                 160

Gln Gln Asn Leu Gly Gly Ala Gly Gly Gly Ile Gly Gly Met Gly
                165                 170                 175

Ile Leu His His Ala Asn Gly Thr Pro Asn Gly Leu Ile Gly Val Val
                180                 185                 190

Gly Gly Gly Gly Gly Val Gly Leu Gly Val Gly Gly Gly Val Gly
            195                 200                 205

Gly Leu Gly Met Gln His Thr Pro Arg Ser Asp Ser Val Asn Ser Ile
        210                 215                 220

Ser Ser Gly Arg Asp Asp Leu Ser Pro Ser Ser Ser Leu Asn Gly Tyr
225                 230                 235                 240

Ser Ala Asn Glu Ser Cys Asp Ala Lys Lys Ser Lys Lys Gly Pro Ala
                245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
        275                 280                 285

Arg Arg Ser Val Thr Lys Ser Ala Val Tyr Cys Cys Lys Phe Gly Arg
        290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Met Arg Pro Glu Cys Val Val Pro
                325                 330                 335

Glu Asn Gln Cys Ala Met Lys Arg Arg Glu Lys Lys Ala Gln Lys Glu
            340                 345                 350

Lys Asp Lys Met Thr Thr Ser Pro Ser Ser Gln His Gly Gly Asn Gly
            355                 360                 365

Ser Leu Ala Ser Gly Gly Gly Gln Asp Phe Val Lys Lys Glu Ile Leu
    370                 375                 380

Asp Leu Met Thr Cys Glu Pro Pro Gln His Ala Thr Ile Pro Leu Leu
385                 390                 395                 400

Pro Asp Glu Ile Leu Ala Lys Cys Gln Ala Arg Asn Ile Pro Ser Leu
            405                 410                 415

Thr Tyr Asn Gln Leu Ala Val Ile Tyr Lys Leu Ile Trp Tyr Gln Asp
            420                 425                 430

Gly Tyr Glu Gln Pro Ser Glu Glu Asp Leu Arg Arg Ile Met Ser Gln
        435                 440                 445

Pro Asp Glu Asn Glu Ser Gln Thr Asp Val Ser Phe Arg His Ile Thr
            450                 455                 460

Glu Ile Thr Ile Leu Thr Val Gln Leu Ile Val Glu Phe Ala Lys Gly
465                 470                 475                 480
```

-continued

```
Leu Pro Ala Phe Thr Lys Ile Pro Gln Glu Asp Gln Ile Thr Leu Leu
                485             490             495
Lys Ala Cys Ser Ser Glu Val Met Met Leu Arg Met Ala Arg Arg Tyr
            500             505             510
Asp His Ser Ser Asp Ser Ile Phe Phe Ala Asn Asn Arg Ser Tyr Thr
        515             520             525
Arg Asp Ser Tyr Lys Met Ala Gly Met Ala Asp Asn Ile Glu Asp Leu
    530             535             540
Leu His Phe Cys Arg Gln Met Phe Ser Met Lys Val Asp Asn Val Glu
545             550             555             560
Tyr Ala Leu Leu Thr Ala Ile Val Ile Phe Ser Asp Arg Pro Gly Leu
                565             570             575
Glu Lys Ala Gln Leu Val Glu Ala Ile Gln Ser Tyr Tyr Ile Asp Thr
            580             585             590
Leu Arg Ile Tyr Ile Leu Asn Arg His Cys Gly Asp Ser Met Ser Leu
        595             600             605
Val Phe Tyr Ala Lys Leu Leu Ser Ile Leu Thr Glu Leu Arg Thr Leu
    610             615             620
Gly Asn Gln Asn Ala Glu Met Cys Phe Ser Leu Lys Leu Lys Asn Arg
625             630             635             640
Lys Leu Pro Lys Phe Leu Glu Glu Ile Trp Asp Val His Ala Ile Pro
                645             650             655
Pro Ser Val Gln Ser His Leu Gln Ile Thr Gln Glu Glu Asn Glu Arg
            660             665             670
Leu Glu Arg Ala Glu Arg Met Arg Ala Ser Val Gly Gly Ala Ile Thr
        675             680             685
Ala Gly Ile Asp Cys Asp Ser Ala Ser Thr Ser Ala Ala Ala Ala Ala
    690             695             700
Ala Gln His Gln Pro Gln Pro Gln Pro Gln Pro Gln Pro Ser Ser Leu
705             710             715             720
Thr Gln Asn Asp Ser Gln His Gln Thr Gln Pro Gln Leu Gln Pro Gln
                725             730             735
Leu Pro Pro Gln Leu Gln Gly Gln Leu Gln Pro Gln Leu Gln Pro Gln
            740             745             750
Leu Gln Thr Gln Leu Gln Pro Gln Ile Gln Pro Gln Pro Gln Leu Leu
        755             760             765
Pro Val Ser Ala Pro Val Pro Ala Ser Val Thr Ala Pro Gly Ser Leu
    770             775             780
Ser Ala Val Ser Thr Ser Ser Glu Tyr Met Gly Gly Ser Ala Ala Ile
785             790             795             800
Gly Pro Ile Thr Pro Ala Thr Thr Ser Ser Ile Thr Ala Ala Val Thr
                805             810             815
Ala Ser Ser Thr Thr Ser Ala Val Pro Met Gly Asn Gly Val Gly Val
            820             825             830
Gly Val Gly Val Gly Gly Asn Val Ser Met Tyr Ala Asn Ala Gln Thr
        835             840             845
Ala Met Ala Leu Met Gly Val Ala Leu His Ser His Gln Glu Gln Leu
    850             855             860
Ile Gly Gly Val Ala Val Lys Ser Glu His Ser Thr Thr Ala
865             870             875

<210> SEQ ID NO 76
<211> LENGTH: 3336
<212> TYPE: DNA
```

<213> ORGANISM: Lucilia cuprina

<400> SEQUENCE: 76

```
ttttttttcga tttttcttgt tgtttcttct ccaacataaa tgacgtttag tttaacatca    60
ttattatcta taagaaatga aaacaacaac aaatgtgcct gtgtttatgt gtgcgtgtgt   120
gtgtatctaa ctaaataaaa ggtattaaac tacaaaaaca aatccttaag ggaatcaatt   180
ggttggaatc tggggttttt ttaaatttat gcgctgctgg catataaaaa aaacaacaac   240
aaaaacaaac acagacctaa aacaaaaatc tgttgaaatt tacaaaaaag tgcaaaaaaa   300
tctcctgaat taaaagctta aattgaaaaa aagcaaaaa taattttttt attttgaaat    360
ttttaacttg ttgctgtttt ttattaaaat tattttataa ttttttgctg taaacggttg   420
acctgcttaa caaattgtga tacaaatata caacaacaaa aaaacaaaca aattggatta   480
ttttaccaac aacaaaaaca acaaacccctt gttataacta cttcaaaaaa ctacctgtca   540
aatggattat tatataaaaa caacttctta aagaaaatta ataaaaaaac gtttatttt    600
tggttaattt ctaactcctg aaacaataat accccccaaa aaagcacttt atttgtacat   660
ccccacacat aaaacacttt tatactttttc aagatcaaac aaaagtataa aagaaaaaat   720
ttcttttcaa aatctgtttc caaatgatga aacgacgttg gtctaataat ggcggttttg   780
ccgctttaaa aatgttagaa gaatcctcct cagaagtaac ctcctcctca aatggtctgg   840
tcttgtcatc ggatataaat atgtcacctt cctcgttgga ttcacccgtt tatggcgatc   900
aggaaatgtg gctgtgtaac gattcagctt catataataa cagtcatcag catagtgtta   960
taacttcgct gcagggctgc acctcatcat tgccggccca aacaaccatt atacctctgt  1020
cagctttacc caattccaat aatgcctccc tgaataatca aaatcaaaat tatcaaaatg  1080
gtaattccat gaatacaaat ttatcggtta acacaaataa cagtgttgga ggaggtggag  1140
gtggtggtgg tgtacccggt atgacttcac tcaatggtct gggtggtggt ggtggcagtc  1200
aagtgaataa tcacaatcac agccacaatc atttacacca caacagcaac agtaatcaca  1260
gtaatagcag ttcccaccac acaaatggcc acatgggtat tggcggcggt ggtggtggct  1320
tatcggtcaa tattaatggt cccaatatcg ttagcaatgc ccaacagtta aactcgttac  1380
aggcctcaca aaatggccaa gttattcatg ccaatattgg cattcacagt atcatcagta  1440
atggattaaa tcatcatcac catcatcata tgaataacag tagtatgatg catcatacac  1500
ccagatctga atcagctaat tccatatcat caggtcgtga tgatctttca ccctcgagca  1560
gtcttaatgg cttctcaaca agcgatgcta gtgatgttaa gaaaatcaaa aaaggtcctg  1620
cgccccgttt acaagaggaa ctgtgtctgg tgtgtggtga tcgggcgtcc ggttatcatt  1680
ataacgcact cacctgtgaa ggctgtaagg ggttctttcg acggagtgtt accaaaaatg  1740
cggtgtattg ttgtaaattt ggtcatgcct gcgaaatgga catgtatatg cgacgtaaat  1800
gtcaggaatg taggctgaaa aaatgtttgg ctgtgggcat gcggccggaa tgtgtggtgc  1860
ccgaaaacca gtgtgcaatg aaacgacgcg aaaagaaagc acaaaagag aaggataaaa  1920
tacagaccag tgtgtgtgca acggaaatta aaaaggaaat actcgattta atgacatgtg  1980
aaccgccatc acatccaacg tgtccgctgt tacctgaaga cattttggct aaatgtcaag  2040
ctcgtaatat acctccttta tcgtacaatc aattggcagt tatatataaa ttaatatggt  2100
atcaagatgg ctacgaacag ccatccgagg aagatctcaa acgtataatg agttcacccg  2160
atgaaaatga aagtcaacac gatgcatcat ttcgtcatat aacagaaatc actatactaa  2220
cagtacaatt aattgtggaa tttgccaagg gtttgccagc gtttaccaaa ataccacaag  2280
```

-continued

```
aggatcaaat aacactatta aaggcctgct catcagaagt tatgatgttg cgaatggcac    2340
gacgttacga tcacaattca gattcgatat tctttgccaa taatcgatcg tatacgcgtg    2400
actcttataa aatggctggc atggctgata atattgagga tctgctgcat ttctgtcgac    2460
aaatgtactc gatgaaagtg gacaatgtcg aatatgctct actcactgcc attgtgatct    2520
tttccgatcg gccgggtctc gaagaagcca aactagtcga agcgatacaa agttactaca    2580
tcgatacact ccgcatttac atacttaatc gccattgcgg cgatcccatg agtctcgtat    2640
tctttgccaa gcttctgtca attctaaccg aactgcgtac gttgggcaat caaaatgccg    2700
aaatgtgttt ctcgttgaaa ttgaaaaatc gcaaactgcc aaaattcctc gaagagatct    2760
gggatgtaca tgccattcca ccctcagtgc agtcacacat acaggctacc caggcggaaa    2820
aggccgccca ggaagctcag gcaacaacat cggccatttc agcagccgcc acctcatctt    2880
cctccataaa tacctcgatg gcaacatcat cctcatcatc gttatcgcca tcggcggcct    2940
caacacccaa tggtggtgcc gtcgattatg ttggcaccga tatgagtatg agtttagtac    3000
aatcggataa tgcatagcaa tagcttttaa caactactac tattgccaac gaagagaaga    3060
gtgctgattg tggtggtagt gttaatatcg tccctgagat agtagctgac attgaagaga    3120
cgttgatgat aatgatgttg ttgatgacgg tgatgatgac gatgttgttg atgatgatgt    3180
gacaatgaga gagttgtgtt attaaatact tcttctattt caagtggctg ttaactttat    3240
ccaacatcat cataagttgg aatagaaaag tgatgaaaat taatagatca agagacagaa    3300
accgcaagtg acaaattaaa caaaaaaaaa aaaaaa                              3336
```

<210> SEQ ID NO 77
<211> LENGTH: 507
<212> TYPE: PRT
<213> ORGANISM: Drosophila melanogaster

<400> SEQUENCE: 77

```
Met Asp Asn Cys Asp Gln Asp Ala Ser Phe Arg Leu Ser His Ile Lys
1               5                   10                  15

Glu Glu Val Lys Pro Asp Ile Ser Gln Leu Asn Asp Ser Asn Asn Ser
            20                  25                  30

Ser Phe Ser Pro Lys Ala Glu Ser Pro Val Pro Phe Met Gln Ala Met
        35                  40                  45

Ser Met Val His Val Leu Pro Gly Ser Asn Ser Ala Ser Ser Asn Asn
    50                  55                  60

Asn Ser Ala Gly Asp Ala Gln Met Ala Gln Ala Pro Asn Ser Ala Gly
65                  70                  75                  80

Gly Ser Ala Ala Ala Val Gln Gln Gln Tyr Pro Pro Asn His Pro
                85                  90                  95

Leu Ser Gly Ser Lys His Leu Cys Ser Ile Cys Gly Asp Arg Ala Ser
            100                 105                 110

Gly Lys His Tyr Gly Val Tyr Ser Cys Glu Gly Cys Lys Gly Phe Phe
        115                 120                 125

Lys Arg Thr Val Arg Lys Asp Leu Thr Tyr Ala Cys Arg Glu Asn Arg
    130                 135                 140

Asn Cys Ile Ile Asp Lys Arg Gln Arg Asn Arg Cys Gln Tyr Cys Arg
145                 150                 155                 160

Tyr Gln Lys Cys Leu Thr Cys Gly Met Lys Arg Glu Ala Val Gln Glu
                165                 170                 175

Glu Arg Gln Arg Gly Ala Arg Asn Ala Ala Gly Arg Leu Ser Ala Ser
```

-continued

```
                180                 185                 190
Gly Gly Gly Ser Ser Gly Pro Gly Ser Val Gly Ser Ser Gln
            195                 200                 205

Gly Gly Gly Gly Glu Gly Gly Val Ser Gly Met Gly Ser Gly Asn
        210                  215                 220

Gly Ser Asp Asp Phe Met Thr Asn Ser Val Ser Arg Asp Phe Ser Ile
225                 230                 235                 240

Glu Arg Ile Ile Glu Ala Glu Gln Arg Ala Glu Thr Gln Cys Gly Asp
                245                 250                 255

Arg Ala Leu Thr Phe Leu Arg Val Gly Pro Tyr Ser Thr Val Gln Pro
            260                 265                 270

Asp Tyr Lys Gly Ala Val Ser Ala Leu Cys Gln Val Val Asn Lys Gln
            275                 280                 285

Leu Phe Gln Met Val Glu Tyr Ala Arg Met Met Pro His Phe Ala Gln
            290                 295                 300

Val Pro Leu Asp Asp Gln Val Ile Leu Leu Lys Ala Ala Trp Ile Glu
305                 310                 315                 320

Leu Leu Ile Ala Asn Val Ala Trp Cys Ser Ile Val Ser Leu Asp Asp
                325                 330                 335

Gly Gly Gly Gly Gly Gly Gly Leu Gly His Asp Gly Ser Phe Glu
            340                 345                 350

Arg Arg Ser Pro Gly Leu Gln Pro Gln Gln Leu Phe Leu Asn Gln Ser
            355                 360                 365

Phe Ser Tyr His Arg Asn Ser Ala Ile Lys Ala Gly Val Ser Ala Ile
            370                 375                 380

Phe Asp Arg Ile Leu Ser Glu Leu Ser Val Lys Met Lys Arg Leu Asn
385                 390                 395                 400

Leu Asp Arg Arg Glu Leu Ser Cys Leu Lys Ala Ile Ile Leu Tyr Asn
                405                 410                 415

Pro Asp Ile Arg Gly Ile Lys Ser Arg Ala Glu Ile Glu Met Cys Arg
                420                 425                 430

Glu Lys Val Tyr Ala Cys Leu Asp Glu His Cys Arg Leu Glu His Pro
            435                 440                 445

Gly Asp Asp Gly Arg Phe Ala Gln Leu Leu Leu Arg Leu Pro Ala Leu
450                 455                 460

Arg Ser Ile Ser Leu Lys Cys Gln Asp His Leu Phe Leu Phe Arg Ile
465                 470                 475                 480

Thr Ser Asp Arg Pro Leu Glu Glu Leu Phe Leu Glu Gln Leu Glu Ala
                485                 490                 495

Pro Pro Pro Pro Gly Leu Ala Met Lys Leu Glu
            500                 505
```

<210> SEQ ID NO 78
<211> LENGTH: 2028
<212> TYPE: DNA
<213> ORGANISM: Manduca sexta

<400> SEQUENCE: 78

| | |
|---|---|
| cgcggaatcc gcaaaatcga tgcacgatct gcaaacgaca ttcatcacaa attaaccatc | 60 |
| aaacgagccg cagcaactat tacgaaggcc ggcgactgac gactcaatt attcagatga | 120 |
| tactagtcca acatataaaa tattataaaa tgtctagccc cataactcgc catttgtagc | 180 |
| tataaagact aaaaatgcag ttatagcaac ccgttttgaa cataaagaca gatttattca | 240 |
| cgtatgattg tgtgtggacc ttgagtgcgc cgagtgagac cttcacgccg gtaaccgcgc | 300 |

```
ggaagttgac ggtttttaacg aaaccttcga ccgagtgcag tgagtttcta gtaatgtgag        360
gatgcttgtg cgtggtcatg tcgagcgtgg cgaaaaaaga caagcgcacg atgtcggtga        420
cggcgctgat caacagggct tggccgttga cgccggcgcc gcaccagcag cagtcgatgc        480
cttcttcaca gccctctaac ttcctgcagc cactggctac gccctctacc acacccagcg        540
ttgagcttga catacaatgg ctgaacatag agccggggtt tatgtcgccg atgtcgccgc        600
ccgagatgaa accagacacg gcaatgctcg acggactccg agacgattcg acgccacccc        660
ctgccttcaa gaactaccct cccaaccatc ctctgagcgg ctccaaacac ctctgctcta        720
tatgtggtga cagagcttcg ggaaaacatt acggcgtgta cagttgcgaa ggttgtaagg        780 gcttttttcaa acggacagta aggaaagacc tcacgtacgc gtgccgcgag ataggaact         840 gcatcattga caaacgtcaa aggaaccgtt gtcagtactg ccgctatcag aaatgtctgg        900
cgtgcggcat gaagagggag gcggtgcaag aagagaggca gagggcggcg agaggcaccg        960
aggacgccca cccaagtagc tccgtgcaag agctgtcgat cgagcggctg ctagagattg       1020
agtcgctggt cgcggacccg cccgaagagt tccagtttct tcgcgtgggt cccgaaagtg       1080
gtgtaccagc caagtaccgc gcacctgtct ctagcctctg tcagataggc aacaaacaga       1140
tagcggcgct agtggtgtgg gcgcgcgaca ttccacattt cggacagctg gagctcgagg       1200
atcagatact gctcatcaag aactcatgga acgagttgct tttgttcgcg atcgcttgga       1260
gatctatgga gtacctcacg gatgaacgag agaacgtcga ctcgcgaagc accgcgccgc       1320
cacaactcat gtgtctaatg ccaggcatga cgctgcaccg caactcggcg ctgcaggcgg       1380
gcgtggggca gatcttcgac cgcgtgctgt cggagttgtc gctgaagatg cgcacgctgc       1440
gcatggacca ggccgagtac gtcgcgctca aggccatcat actgctcaac ccagacgtaa       1500
aaggactaaa gaacaaaccg gaagtggtgg ttctgcgtga aagatgttc tcgtgcctgg        1560 acgagtacgt gcggcggtcg cgctgcgcgg aggagggtcg gttcgccgcg ctgctgctgc       1620
gcctgcccgc gctgcgctcc atctcgctca gtgcttcga gcatctctac ttcttccacc        1680
tcgtcgccga caccagcatc gcctcctaca tacacgacgc gctgcgcaac cacgcgccct       1740
ccatcgacac cagcatactg tagactcgca acaccgcca caccgctcgt tacatgcgat        1800
ctgttgcgtg ctgcggttgc ggcttgtagt ttaacgatct ttggcttgaa ggtactcaat       1860
gagtaatatt ttttttcatat cgaaaaaatt ggagcgttta ctcgttgaca tcgtatccaa       1920
agggcgtttt aaggctgtat tgccacgaga ttataaaggc gtgttgggtc tctttcgtgg       1980
atagtttgat cgaaccaaac cacgatgatc tggtgtgtcc acgtcgac                    2028
```

<210> SEQ ID NO 79
<211> LENGTH: 2184
<212> TYPE: DNA
<213> ORGANISM: Drosophila melanogaster

<400> SEQUENCE: 79

```
aacaaagaat gcccaacgga ccaaaagcgg acggacggac acggtggcgt tggcaaagtg          60 aaacccaac agagaggcga aagcgagcca agacacacca catacacacg aagagaacga         120
gcaagaagaa accggtaggc ggaggaggcg ctgcccccag ttcctccaat atcccagca         180 ccacatcaca agcccaggat ggacaactgc gaccaggacg ccagctttcg gctgagccac        240
atcaaggagg aggtcaagcc ggacatctcg cagctgaacg acagcaacaa cagcagcttt        300
tcgcccaagg ccgagagtcc cgtgcccttc atgcaggcca tgtccatggt ccacgtgctg        360
```

```
cccggctcca actccgccag ctccaacaac aacagcgctg gagatgccca aatggcgcag      420
gcgcccaatt cggctggagg ctctgccgcc gctgcagtcc agcagcagta ccgcctaac      480 catccgctga gcggcagcaa gcacctctgc tctatttgcg gggatcgggc cagtggcaag      540
cactacggcg tgtacagctg tgagggctgc aagggcttct ttaaacgcac agtgcgcaag      600
gatctcacat acgcttgcag ggagaaccgc aactgcatca tagacaagcg gcagaggaac      660
cgctgccagt actgccgcta ccagaagtgc ctaacctgcg gcatgaagcg cgaagcggtc      720
caggaggagc gtcaacgcgg cgcccgcaat gcggcgggta ggctcagcgc cagcggaggc      780
ggcagtagcg gtccaggttc ggtaggcgga tccagctctc aaggcggagg aggagaaggc      840
ggcgtttctg gcggaatggg cagcggcaac ggttctgatg acttcatgac caatagcgtg      900
tccagggatt tctcgatcga gcgcatcata gaggccgagc agcgagcgga gacccaatgc      960
ggcgatcgtg cactgacgtt cctgcgcgtt ggtccctatt ccacagtcca gccggactac     1020
aagggtgccg tgtcggccct gtgccaagtg gtcaacaaac agctcttcca gatggtcgaa     1080
tacgcgcgca tgatgccgca ctttgcccag gtgccgctgg acgaccaggt gattctgctg     1140
aaagccgctt ggatcgagct gctcattgcg aacgtggcct ggtgcagcat cgtttcgctg     1200
gatgacggcg gtggcggcgg gggcggtgga ctaggccacg atggctcctt tgagcgacga     1260
tcaccgggcc ttcagcccca gcagctgttc ctcaaccaga gcttctcgta ccatcgcaac     1320
agtgcgatca aagccggtgt gtcagccatc ttcgaccgca tattgtcgga gctgagtgta     1380
aagatgaagc ggctgaatct cgaccgacgc gagctgtcct gcttgaaggc catcatactg     1440
tacaacccgg acatacgcgg gatcaagagc cgggcggaga tcgagatgtg ccgcgagaag     1500
gtgtacgctt gcctggacga gcactgccgc ctggaacatc cgggcgacga tggacgcttt     1560
gcgcaactgc tgctgcgtct gcccgctttg cgatcgatca gcctgaagtg ccaggatcac     1620
ctgttcctct tccgcattac cagcgaccgg ccgctggagg agctctttct cgagcagctg     1680
gaggcgccgc cgccacccgg cctggcgatg aaactggagt agggtcccga ctctaaaggc     1740 gccccgttc tccctccgaa aatgcttcat tgtgattgcg tttgtttgca tttctcctct     1800
ctactccctt ataccctaca aaggccccct aatattacgc aaaatgtgta tgtaattgtt     1860
tatttttttt ttattaccta atattattat tattattgat atagaaaatg ttttccttaa     1920
gatgaagatt agcctcctcg acgtttatgt cccagtaaac gaaaaacaaa caaaatccaa     1980
aacttgaaaa gaacacaaaa cacgaacgag aaaatgcaca caagcaaaag taaaagtaaa     2040
agttaaacta aagctaaacg agtaaagata ttaaaataac ggttaaaatt aatgcatagt     2100
tatgatctac agacgtatgt aaacatacaa attcagcata aatatatatg tcagcaggca     2160
tatctgcggt gcaggccccg ttct                                             2184
```

FLEA ULTRASPIRACLE NUCLEIC ACID MOLECULES

CROSS REFERENCE TO RELATED APPLICATIONS

The present application is a Divisional of U.S. patent application Ser. No. 10/855,541, filed May 27, 2004, now U.S. Pat. No. 7,208,589 entitled "FLEA ULTRASPIRACLE NUCLEIC ACID MOLECULES AND USES THEREOF"; which is a Divisional of U.S. patent application Ser. No. 10/065,200, filed Sep. 25, 2002, now U.S. Pat. No. 6,767,721 B2, entitled "FLEA ECDYSONE NUCLEIC ACID MOLECULES AND USES THEREOF"; which is a Divisional of U.S. patent application Ser. No. 09/435,019, filed Nov. 5, 1999, now U.S. Pat. No. 6,489,140 B1, entitled "FLEA ECDYSONE AND ULTRASPIRACLE NUCLEIC ACID MOLECULES, PROTEINS AND USES THEREOF"; which claims priority to U.S. Provisional Patent Application Ser. No. 60/107,559, filed Nov. 6, 1998; and all of foregoing are incorporated herein by reference.

FIELD OF THE INVENTION

The present invention relates to flea ecdysone and ultraspiracle nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from flea infestation.

BACKGROUND OF THE INVENTION

Flea infestation of animals is a health and economic concern because fleas are known to cause and/or transmit a variety of diseases. Fleas directly cause a variety of diseases, including allergies, and also carry a variety of infectious agents including, but not limited to, endoparasites (e.g., nematodes, cestodes, trematodes and protozoa), bacteria and viruses. In particular, the bites of fleas are a problem for animals maintained as pets because the infestation becomes a source of annoyance not only for the pet but also for the pet owner who may find his or her home generally contaminated with insects. As such, fleas are a problem not only when they are on an animal but also when they are in the general environment of the animal.

Bites from fleas are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of flea infestation has prompted the development of reagents capable of controlling flea infestation. Commonly encountered methods to control flea infestation are generally focused on use of insecticides. While some of these products are efficacious, most, at best, offer protection of a very limited duration. Furthermore, many of the methods are often not successful in reducing flea populations. In particular, insecticides have been used to prevent flea infestation of animals by adding such insecticides to shampoos, powders, collars, sprays, foggers and liquid bath treatments (i.e., dips). Reduction of flea infestation on the pet has been unsuccessful for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Flea populations, however, have been found to become resistant to insecticides.

20-Hydroxyecdysone (ecdysone) is the insect steroid hormone which regulates molting and metamorphosis. The ability of ecdysone to have a pleiotropic effect upon various tissues is dependent upon the formation of a complex of ecdysone with its receptor (EcR) and its heterodimeric partner, ultraspiracle (USP). This complex then binds to ecdysone response elements (EcRE) found within the promoters of insect genes, and thereby affecting DNA transcription. EcR by itself has been reported to be incapable of high affinity binding or transcriptional activation, rather, these activities appear to be dependent upon heterodimer formation with USP, Yao et al., 1993, Nature 366, 476-479.

Prior investigators have described certain insect EcR protein or nucleic acid sequences, including for example, *Bombyx mori*, Swevers et al., 1995, Insect Biochem. Mol. Biol. 25(7), 857-866; *Drosophila melanogaster*, Koelle et al., 1991, Cell 67(1), 59-77; and *Manduca sexta*, Fujiwara et al., 1995, Insect Biochem. Mol Biol. 25(7), 845-856; and certain insect USP protein and nucleic acid sequences, including for example, *Bombyx mori*, Tzertzinis et al., 1994, J. Mol. Biol. 238, 479-486; *Drosophila melanogaster*, Oro et al., 1990, Nature, 347(6290) 298-301; and *Manduca sexta*, Jindra et al., GenBank Accession 1718061 (SEQ ID NO:72). Prior investigators have also described mammalian homologs of EcR and USP, Giguere et al., 1987, Nature 330(6149), 624-629; Cooke et al., 1996, GenBank Accession 1350913 (SEQ ID NO:73); Leid et al., 1992, Cell 68(2), 377-395; and amphibian homologs, Blumberg et al., 1992, Proc. Natl. Acad. Sci., U.S.A. 89(6), 2321-2325.

Identification of flea EcR and USP of the present invention is surprising, however, due to the source from which these molecules were identified. Most lepidopterans and dipterans are better characterized, relative to *C. felis*, with respect to visible signs of molting, the only stages which should possess high levels of ecdysone. Ecdysone is necessary for the up regulation of mRNA encoding EcR and USP. Therefore, the lack of clear, easily visible signs of molting in *C. felis* make the likelihood of finding cDNA containing EcR or USP message in the larval and prepupal cDNA unexpected.

Thus, there remains a need to develop a reagent and a method to protect animals from flea infestation.

SUMMARY OF THE INVENTION

The present invention relates to a novel product and process for protection of animals from flea infestation. Identification of flea EcR and USP of the present invention is surprising, however, due to the source from which these molecules were identified. Most lepidopterans and dipterans are better characterized, relative to *C. felis*, with respect to visible signs of molting, the only stages which should possess high levels of ecdysone. Ecdysone is necessary for the up regulation of mRNA encoding EcR and USP. Therefore, the lack of clear, easily visible signs of molting in *C. felis* make the likelihood of finding cDNA containing EcR or USP message in the larval and prepupal cDNA unexpected.

According to the present invention there are provided flea ecdysone receptor (EcR) or ultraspiracle (USP) proteins, and mimetopes thereof; flea EcR and USP nucleic acid molecules, including those that encode such proteins; antibodies raised against such EcR and USP proteins (i.e., anti-flea EcR and USP antibodies); and compounds that inhibit flea EcR and USP activity (i.e., inhibitory compounds or inhibitors).

The present invention also includes methods to obtain such proteins, mimetopes, nucleic acid molecules, antibodies and inhibitory compounds. Also included in the present invention are therapeutic compositions comprising a protective compound derived from a protein of the present invention that inhibits the binding between ecdysone receptor and ecdysone.

One embodiment of the present invention is an isolated nucleic acid molecule having at least about 34 nucleotides which hybridizes with a nucleic acid sequence having SEQ ID NO:5, SEQ ID NO:7, SEQ ID NO:8, SEQ ID NO:10, SEQ ID NO:13, SEQ ID NO:15, SEQ ID NO:16 and/or SEQ ID NO:18 under conditions that allow about 30% base pair mismatch. Another embodiment of the present invention is an isolated nucleic acid molecule having at least about 30 nucleotides which hybridizes with a nucleic acid sequence having SEQ ID NO:26, SEQ ID NO:28, SEQ ID NO:29, SEQ ID NO:31, SEQ ID NO:32, SEQ ID NO:34, SEQ ID NO:35 and/or SEQ ID NO:37 under conditions that allow about 30% base pair mismatch.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

The present invention also relates to mimetopes of flea EcR and/or USP proteins as well as to isolated antibodies that selectively bind to flea EcR and/or USP proteins or mimetopes thereof. Also included are methods, including recombinant methods, to produce proteins, mimetopes and antibodies of the present invention.

Another embodiment of the present invention includes an isolated flea ecdysone receptor protein selected from the group consisting of a protein comprising (a) an amino acid sequence that is at least about 70% identical to an amino acid sequence selected from the group consisting of SEQ ID NO:6 and/or SEQ ID NO:14, wherein said protein is at least about 71 amino acids residues in length; (b) a protein consisting of an amino acid sequence having SEQ ID NO:64 and/or SEQ ID NO:65, and fragments thereof, wherein said protein has at least a portion of an ecdysone receptor DNA binding domain; (c) a protein consisting of an amino acid sequence having SEQ ID NO:66 and/or SEQ ID NO:67, and fragments thereof, wherein said protein has at least a portion of an ecdysone receptor ligand binding domain; or (d) a protein encoded by an allelic variant of nucleic acid molecules encoding any protein of (a), (b), and/or (c).

Another embodiment of the present invention includes an isolated flea ultraspiracle protein selected from the group consisting of: (a) a protein comprising an amino acid sequence that is at least about 70% identical to an amino acid sequence selected from the group consisting of SEQ ID NO:27 and SEQ ID NO:33, wherein said protein is at least about 72 amino acid residues in length; (b) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of an ultraspiracle protein that is capable of affecting binding of ecdysone receptor to ecdysone; and (c) a protein encoded by an allelic variant of a nucleic acid molecule which encodes any protein of (a) or (b).

Another embodiment of the present invention includes an isolated protein encoded by a nucleic acid molecule having a nucleic acid sequence selected from the group consisting of SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35.

Another embodiment of the present invention includes a method to identify a compound capable of inhibiting EcR activity, the method comprising: (a) contacting an isolated flea EcR protein comprising an amino acid sequence selected from the group consisting of SEQ ID NO:6 and SEQ ID NO:14, with a putative inhibitory compound under conditions in which, in the absence of the putative inhibitory compound, the protein has EcR activity, and (b) determining if the putative inhibitory compound inhibits EcR activity.

Another embodiment of the present invention includes a method to identify a compound capable of inhibiting flea activity, the method comprising: (a) contacting an isolated flea USP protein comprising an amino acid sequence consisting of SEQ ID NO:27 and SEQ ID NO:33, with a putative inhibitory compound under conditions in which, in the absence of the putative inhibitory compound, the protein has USP activity, and (b) determining if the putative inhibitory compound inhibits USP activity.

DETAILED DESCRIPTION OF THE INVENTION

The present invention provides for isolated flea ecdysone (EcR) and ultraspiracle (USP) proteins, isolated flea Eck and USP nucleic acid molecules, isolated antibodies directed against flea EcR and USP proteins, and compounds able to inhibit flea EcR and/or USP function (i.e., inhibitory compounds). As used herein, the terms isolated flea EcR and USP proteins and isolated flea EcR and USP nucleic acid molecules refer to EcR and USP proteins and EcR and USP nucleic acid molecules derived from fleas; as such the proteins and nucleic acid molecules can be isolated from an organism or prepared recombinantly or synthetically. Flea EcR nucleic acid molecules of known length are denoted "nECR$_{\#}$", for example nECR$_{4148}$, wherein "#" refers to the number of nucleotides in that molecule, and EcR proteins of known length are denoted "Pecr$_{\#}$" (for example Pecr$_{562}$) wherein "#" refers to the number of amino acid residues in that molecule. Similarly, USP nucleic acid molecules and proteins of known length are denoted "nUSP$_{\#}$" and "Pusp$_{\#}$", respectively. The proteins and nucleic acid molecules of the present invention can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from flea infestation as well as in other applications, such as those disclosed below.

Flea EcR and USP proteins and nucleic acid molecules of the present invention have utility because they represent novel targets for anti-arthropod vaccines and chemotherapeutic drugs. The products and processes of the present invention are advantageous because they enable the inhibition of arthropod development, metamorphosis, feeding, digestion and reproduction processes that involve EcR and/or USP proteins. While not being bound by theory, it is believed that expression of arthropod EcR and USP proteins are developmentally regulated, thereby suggesting that EcR and USP proteins are involved in arthropod development and/or reproduction. The present invention is particularly advantageous because the proteins of the present invention were identified in larval fleas, thereby suggesting the importance of the proteins as developmental proteins.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain an EcR and/or USP formulation of the present invention include, but are not limited to, unfed or fed $1^{st}$ instar larvae; fed $3^{rd}$ instar larvae, fed wandering larvae, fed prepupal larvae, fed pupae and whole unfed or fed adult fleas. Preferred flea tissue from which to obtain an EcR and/or USP formulation of the present invention includes third instar larvae, wandering larvae, prepupal larvae, pupae, and adult fleas.

In a preferred embodiment, a formulation of the present invention comprises a flea EcR protein comprising amino acid sequence SEQ ID NO:6 or SEQ ID NO:14, and/or a flea USP protein comprising amino acid sequence SEQ ID NO:27 or SEQ ID NO:33.

One embodiment of the present invention is an isolated protein that includes a flea EcR and/or USP protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea EcR and/or USP proteins of the present invention can be full-length proteins or any homolog of such proteins. An isolated protein of the present invention, including a homolog, can be identified in a straight-forward manner by the protein's ability to elicit an immune response against a flea EcR or USP protein or by the protein's EcR or USP activity. Examples of flea EcR and USP homolog proteins include flea EcR and USP proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a flea EcR or USP protein, and/or of binding to an antibody directed against a flea EcR or USP protein. That is, when the homolog is administered to an animal as an immunogen, using techniques known to those skilled in the art, the animal will produce an immune response against at least one epitope of a natural flea EcR or USP protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids in length.

In one embodiment of the present invention a flea homolog protein has EcR or USP activity. Examples of methods to detect EcR and/or USP activity are disclosed herein. Flea EcR and USP homolog proteins can be the result of natural allelic variation or natural mutation. Flea EcR and USP protein homologs of the present invention can also be produced using techniques known in the art including, but not limited to, direct modifications to the protein or modifications to the gene encoding the protein using, for example, classic or recombinant DNA techniques to effect random or targeted mutagenesis.

Flea EcR and USP proteins of the present invention are encoded by flea EcR and USP nucleic acid molecules, respectively. As used herein, flea EcR and USP nucleic acid molecules include nucleic acid sequences related to natural flea EcR and USP genes, and, preferably, to Ctenocephalides felis EcR and USP genes. As used herein, flea EcR and USP genes include all regions such as regulatory regions that control production of flea EcR and USP proteins encoded by such genes (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a fill-length, i.e., a complete protein as would be initially translated in its natural millieu, prior to any post-translational modifications.

One embodiment of the present invention is a C. felis EcR gene that includes the nucleic acid sequence SEQ ID NO:5, SEQ ID NO:8, SEQ ID NO:13, and/or SEQ ID NO:16, as well as the complements of any of these nucleic acid sequences; and a C. felis USP gene that includes the nucleic acid sequence SEQ ID NO:26, SEQ ID NO:29, SEQ ID NO:32, and/or SEQ ID NO:35 as well as the complements of any of these nucleic acid sequences. These nucleic acid sequences are further described herein. For example, nucleic acid sequence SEQ ID NO:8 represents the deduced sequence of the coding strand of a C. felis cDNA (complementary DNA) denoted herein as C. felis EcR nucleic acid molecule $nECR_{680}$, the production of which is disclosed in the Examples. Nucleic acid molecule $nECR_{680}$ comprises an apparently full-length coding region. The complement of SEQ ID NO:8 (represented herein by SEQ ID NO:10) refers to the nucleic acid sequence of the strand complementary to the strand having SEQ ID NO:8, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:8 (as well as other nucleic acid and protein sequences presented herein) represents an apparent nucleic acid sequence of the nucleic acid molecule encoding an EcR protein of the present invention.

In another embodiment, an EcR gene or nucleic acid molecule can be an allelic variant that includes a similar but not identical sequence to SEQ ID NO:5, SEQ ID NO:7, SEQ ID NO:8, SEQ ID NO:10, SEQ ID NO:13, SEQ ID NO:15, SEQ ID NO:16, and/or SEQ ID NO:18, or any other *C. felis* EcR nucleic acid sequence cited herein and a USP gene or nucleic acid molecule can be an allelic variant that includes a similar but not identical sequence to SEQ ID NO:26, SEQ ID NO:28, SEQ ID NO:29, SEQ ID NO:31, SEQ ID NO:32, SEQ ID NO:34, SEQ ID NO:35, and/or SEQ ID NO:37, or any other *C. felis* USP nucleic acid sequence cited herein. For example, an allelic variant of a *C. felis* EcR gene including SEQ ID NO:8 is a gene that occurs at essentially the same locus (or loci) in the genome as the gene including SEQ ID NO:8, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea such as *C. felis*, since the genome is diploid, and sexual reproduction will result in the reassortment of alleles.

In one embodiment of the present invention, isolated EcR and USP proteins are encoded by nucleic acid molecules that hybridize under stringent hybridization conditions to genes encoding flea EcR and USP proteins respectively. The minimal size of EcR and USP proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea EcR or USP nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea EcR or USP protein is typically at least about 12 to about 15 nucleotides in length if the nucleic acid molecule is GC-rich and at least about 15 to about 17 bases in length if it is AT-rich. The minimal size of a nucleic acid molecule used to encode an EcR or USP protein homolog of the present invention is from about 12 to about 18 nucleotides in length. Thus, the minimal size of EcR or USP protein homologs of the present invention is from about 4 to about 6 amino acids in length. There is no limit, other than a practical limit, on the maximal size of a nucleic acid molecule encoding a flea EcR or USP protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% G+C) - 500/n - 0.61(\% \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Stringent hybridization conditions are commonly understood by those skilled in the art to be those experimental conditions that will allow about 30% base pair mismatch (i.e., about 70% identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a C. felis nucleic acid molecule of about 150 bp in length, the following conditions could preferably be used. The average G+C content of C. felis DNA is about 43%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base pair mismatch. For example, in a wash solution comprising 1×SSC and 0% formamide, the $T_m$ of perfect hybrids would be about 82° C.:

$$81.5° C.+16.6 \log(0.15M)+(0.41\times43)-(500/150)-(0.61\times0)=82° C.$$

Thus, to achieve hybridization with nucleic acid molecules having about 30% base pair mismatch, hybridization washes would be carried out at a temperature of about 52° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 52° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the GAP program with pair-wise comparisons within the program GCG™ Version 9.0-UNIX, hereinafter referred to as default parameters.

Another embodiment of the present invention includes flea EcR and USP proteins. A preferred flea EcR protein includes a protein encoded by a nucleic acid molecule which is at least about 34 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:10, SEQ ID NO:15, and SEQ ID NO:18.

A preferred flea USP protein includes a protein encoded by a nucleic acid molecule which is at least about 30 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:28, SEQ ID NO:31, SEQ ID NO:34, and SEQ ID NO:37.

Another embodiment of the present invention includes a flea EcR protein encoded by a nucleic acid molecule comprising at least about 34 base pairs, wherein said nucleic acid molecule hybridizes, in a solution comprising 1×SSC and 0% formamide, at a temperature of about 52° C., to an isolated nucleic acid molecule selected from the group consisting of SEQ ID NO:7, SEQ ID NO:10, SEQ ID NO:15, and SEQ ID NO:18.

Another embodiment of the present invention includes a flea USP protein encoded by a nucleic acid molecule comprising at least about 30 base pairs, wherein said nucleic acid molecule hybridizes, in a solution comprising 1×SSC and 0% formamide, at a temperature of about 52° C., to an isolated nucleic acid molecule selected from the group consisting of SEQ ID NO:28, SEQ ID NO:31, SEQ ID NO:34, and SEQ ID NO:37.

Another preferred flea EcR protein of the present invention includes a protein which is encoded by a nucleic acid molecule that is preferably about 70% identical, more preferably about 75% identical, more preferably about 80% identical, more preferably about 85% identical, more preferably about 90% identical, and even more preferably about 95% identical to a nucleic acid molecule having the nucleic acid sequence SEQ ID NO:5, SEQ ID NO:8, SEQ ID NO:13, and/or SEQ ID NO:16; also preferred are fragments (i.e. portions) of such proteins encoded by nucleic acid molecules which are at least about 30 nucleotides. Percent identity as used herein is determined using the Compare function by maximum matching within the program DNAsis Version 2.1 using default parameters.

Another preferred flea USP protein of the present invention includes a protein which is encoded by a nucleic acid molecule that is preferably about 70% identical, more preferably about 75% identical, more preferably about 80% identical, more preferably about 85% identical, more preferably about 90% identical, and even more preferably about 95% identical to a nucleic acid molecule having the nucleic acid sequence SEQ ID NO:26, SEQ ID NO:29, SEQ ID NO:32, and/or SEQ ID NO:35; also preferred are fragments (i.e. portions) of such proteins encoded by nucleic acid molecules which are at least about 34 nucleotides. Percent identity as used herein is determined using the Compare function by maximum matching within the program DNAsis Version 2.1 using default parameters.

Additional preferred flea EcR proteins of the present invention include proteins having the amino acid sequence SEQ ID NO:6 or SEQ ID NO:14, and proteins comprising homologs of a protein having the amino acid sequence SEQ ID NO:6 or SEQ ID NO:14, wherein such a homolog comprises at least one epitope that elicits an immune response against a protein having an amino acid sequence SEQ ID NO:6 or SEQ ID NO:14. Likewise, also preferred are proteins encoded by nucleic acid molecules comprising nucleic acid sequence SEQ ID NO:5, SEQ ID NO:8, SEQ ID NO:13, and/or SEQ ID NO:16, or by homologs thereof.

Additional preferred flea USP proteins of the present invention include proteins having the amino acid sequence SEQ ID NO:27 or SEQ ID NO:33, and proteins comprising homologs of a protein having the amino acid sequence SEQ ID NO:27 or SEQ ID NO:33, wherein such a homolog comprises at least one epitope that elicits an immune response against a protein having an amino acid sequence SEQ ID NO:27 or SEQ ID NO:33. Likewise, also preferred are proteins encoded by nucleic acid molecules comprising nucleic acid sequence SEQ ID NO:26, SEQ ID NO:29, SEQ ID NO:32, and/or SEQ ID NO:35, or by homologs thereof.

A preferred isolated protein of the present invention is a protein encoded by at least one of the following nucleic acid molecules: $nECR_{2822}$, $nECR_{1680}$, $nECR_{666}$, $nECR_{4148}$, $nECR_{1683}$, $nECR_{612}$ $nUSP_{1749}$, $nUSP_{1344}$, $nUSP_{1975}$, $nUSP_{1422}$, $nUSP_{776}$, or $nUSP_{943}$ or allelic variants of any of these nucleic acid molecules. Another preferred isolated protein is encoded by a nucleic acid molecule having nucleic acid sequence SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35; or a protein encoded by an allelic variant of any of these listed nucleic acid molecule.

Translation of SEQ ID NO:8, the coding strand of $nECR_{1680}$, yields a protein of about 560 amino acids, denoted herein as $PECR_{560}$, the amino acid sequence of which is presented in SEQ ID NO:6, assuming a first in-frame codon extending from nucleotide 1 to nucleotide 3 of SEQ ID NO:8. Sequence analysis of SEQ ID NO:6 revealed a putative DNA binding domain spanning from amino acid residue 142 to residue 207 of SEQ ID NO:6, designated SEQ ID NO:64. Sequence analysis also revealed a putative ecdysone (i.e., ligand) binding domain spanning from amino acid residue 309 to residue 527 of SEQ ID NO:6, designated SEQ ID NO:65.

Translation of SEQ ID NO:16, the coding strand of $nECR_{1683}$, yields a protein of about 561 amino acids, denoted herein as $PECR_{561}$, the amino acid sequence of which is presented in SEQ ID NO:14, assuming a first in-frame codon extending from nucleotide 1 to nucleotide 3 of SEQ ID NO:16. Sequence analysis of SEQ ID NO:14 revealed a putative EcR DNA binding domain spanning from amino acid residue 143 to residue 208 of SEQ ID NO:14, designated SEQ ID NO:66. Sequence analysis also revealed a putative ligand binding domain spanning from amino acid residue 310 to residue 528 of SEQ ID NO:4, designated SEQ ID NO:67.

It is within the scope of the invention that the DNA binding domains represented by SEQ ID NO:64 and SEQ ID NO:66 represent protein domains capable of binding to an ecdysone response element and the ligand binding domains represented by SEQ ID NO:65 and SEQ ID NO:67 represent protein domains capable of binding to ecdysone.

Translation of SEQ ID NO:29, the coding strand of $nUSP_{1344}$, yields a protein of about 448 amino acids, denoted herein as $PUSP_{448}$, the amino acid sequence of which is presented in SEQ ID NO:27, assuming a first in-frame codon extending from nucleotide 1 to nucleotide 3 of SEQ ID NO:29. Sequence analysis of SEQ ID NO:27 revealed a putative USP DNA binding domain spanning from amino acid residue 89 to residue 154 of SEQ ID NO:27, designated SEQ ID NO:68. Sequence analysis also revealed a putative ligand binding domain spanning from amino acid residue 178 to residue 448 of SEQ ID NO:27, designated SEQ ID NO:69.

Translation of SEQ ID NO:35, the coding strand of $nUSP_{1422}$, yields a protein of about 474 amino acids, denoted herein as $PUSP_{474}$, the amino acid sequence of which is presented in SEQ ID NO:33, assuming a first in-frame codon extending from nucleotide 1 to nucleotide 3 of SEQ ID NO:35. Sequence analysis of SEQ ID NO:33 revealed a putative DNA binding domain spanning from amino acid residue 115 to residue 180 of SEQ ID NO:33, designated SEQ ID NO:70. Sequence analysis also revealed a putative EcR (i.e., ligand) binding domain spanning from amino acid residue 204 to residue 474 of SEQ ID NO:33, designated SEQ ID NO:71.

While not being bound by theory, it is believed that the putative DNA binding domains represented by SEQ ID NO:68 and SEQ ID NO:70 and the putative ligand binding domains represented by SEQ ID NO:69 and SEQ ID NO:71 represent domains capable of affecting the binding of ecdysone receptor to ecdysone and thereby affecting DNA transcription.

Preferred proteins of the present invention include proteins that are at least about 70%, preferably at least about 80%, more preferably at least about 85%, even more preferably at least about 90%, even more preferably at least about 95%, and even more preferably about 100% identical to $PECR_{560}$, $PECR_{561}$, PUSP448, or $PUSP_{474}$. Additionally preferred are proteins encoded by allelic variants of a nucleic acid molecules encoding proteins $PECR_{560}$, $PECR_{561}$, $PUSP_{448}$, or $PUSP_{474}$. Also preferred are fragments thereof having at least about 35 amino acid residues.

Other preferred EcR proteins of the present invention include proteins having amino acid sequences that are at least about 70%, preferably at least about 80%, more preferably at least about 85%, even more preferably at least about 90%, even more preferably at least about 95%, and even more preferably about 100% identical to amino acid sequence SEQ ID NO:6 or SEQ ID NO:14. More preferred are EcR proteins comprising amino acid sequences SEQ ID NO:6 or SEQ ID NO:14; and EcR proteins encoded by allelic variants of nucleic acid molecules encoding EcR proteins having amino acid sequences SEQ ID NO:6 or SEQ ID NO:14. Also preferred are fragments thereof having at least about 35 amino acid residues.

In one embodiment of the present invention, *C. felis* EcR proteins comprise amino acid sequence SEQ ID NO:6 or SEQ ID NO:14 (including, but not limited to, the proteins consisting of amino acid sequence SEQ ID NO:6 or SEQ ID NO:14, fusion proteins and multivalent proteins), and proteins encoded by allelic variants of nucleic acid molecules encoding proteins having amino acid sequence SEQ ID NO:6 or SEQ ID NO:14. In another embodiment, *C. felis* USP proteins of the present invention comprise amino acid sequence SEQ ID NO:27 or SEQ ID NO:33 (including, but not limited to, the proteins consisting of amino acid sequence SEQ ID NO:27 or SEQ ID NO:33, fusion proteins and multivalent proteins), and proteins encoded by allelic variants of nucleic acid molecules encoding proteins having amino acid sequence SEQ ID NO:27 or SEQ ID NO:33.

In one embodiment, a preferred flea EcR protein comprises an amino acid sequence of at least about 35 amino acids, preferably at least about 50 amino acids, more preferably at least about 100 amino acids, more preferably at least about 200 amino acids, more preferably at least about 250 amino acids, more preferably at least about 300 amino acids, more preferably at least about 350 amino acids, more preferably at least about 400 amino acids, more preferably at least about 450 amino acids, more preferably at least about 500 amino acids, even more preferably at least about 550 amino acids and a preferred flea USP protein comprises an amino acid sequence of at least about 35 amino acids, preferably at least about 50 amino acids, more preferably at least about 100 amino acids, more preferably at least about 150 amino acids, more preferably at least about 200 amino acids, more preferably at least about 250 amino acids, more preferably at least about 300 amino acids, more preferably at least about 350 amino acids, more preferably at least about 400 amino acids, more preferably at least about 450 amino acids, even more preferably at least about 475 amino acids. In another embodiment, preferred flea EcR and USP proteins comprise full-length proteins, i.e., proteins encoded by full-length coding regions.

In another embodiment, a preferred flea EcR protein comprises an isolated flea EcR protein selected from the group consisting of: (a) a protein comprising an amino acid sequence that is at least about 70% identical to an amino acid sequence selected from the group consisting of SEQ ID NO:6 and SEQ ID NO 14, wherein said protein is at least about 71 amino acids residues in length; (b) a protein consisting of an amino acid sequence selected from the group consisting of SEQ ID NO:64, SEQ ID NO:65, and fragments thereof, wherein said protein has at least a portion of an EcRE binding domain; (c) a protein consisting of an amino acid sequence selected from the group consisting of SEQ ID NO:66, SEQ ID NO:67, and fragments thereof, wherein said protein has at least a portion of an EcR ligand binding domain or (d) a protein encoded by an allelic variant of a nucleic acid molecule which encodes any protein of (a), (b) or (c).

In another embodiment, a preferred flea USP protein comprises an isolated flea ultraspiracle protein selected from the group consisting of: (a) a protein comprising an amino acid sequence that is at least about 70% identical to an amino acid sequence selected from the group consisting of SEQ ID NO:27 and SEQ ID NO:33, wherein said protein is at least about 72 amino acids residues in length; (b) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of a USP protein that is capable of affecting binding of EcR to ecdysone; or (c) a protein encoded by an allelic variant of a nucleic acid molecule which encodes any protein of (a) or (b). As used herein, the term "capable of affecting" the binding of ecdysone receptor to ecdysone means the ability of USP to act as a heterodimeric binding partner with EcR, i.e. to assist EcR in the binding of ecdysone, preferably to promote, improve and/or enhance high affinity binding between EcR and ecdysone.

One of skill in the art will understand that a DNA or protein fragment of the present invention includes a portion of a larger nucleic acid molecule or protein, respectively. Preferably, DNA fragments including the DNA binding, or ligand binding domains, of EcR can be isolated from SEQ ID NO:5 and/or SEQ ID NO:13 and DNA fragments including the DNA binding, or ligand binding domains, of USP can be isolated from SEQ ID NO:26 and/or SEQ ID NO:32. Preferably, protein fragments including the DNA binding, or ligand binding domains, of EcR can be isolated from SEQ ID NO:6 and/or SEQ ID NO:14 and protein fragments including the DNA binding, or ligand binding domains, of USP can be isolated from SEQ ID NO:27 and/or SEQ ID NO:33.

One of skill in the art will also understand that fragments including the active domains of EcR, or USP, can vary and extend beyond those particular nucleic acid or amino acid regions defined herein. Such active domains can vary in length by 1 amino acid to about 50 amino acids. Nucleic acids or amino acids essential to an active domain can be identified using standard protein or DNA binding assays known to those of skill in the art to determine the ability of an active domain to bind to its ligand, e.g. EcRE, ecdysone or EcR.

A fragment of an EcR and/or USP protein of the present invention preferably comprises at least about 5 amino acids, more preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 40 amino acids, more preferably at least about 45 amino acids, more preferably at least about 50 amino acids, more preferably at least about 55 amino acids, more preferably at least about 60 amino acids, more preferably at least about 65 amino acids, more preferably at least about 70 amino acids, more preferably at least about 75 amino acids, more preferably at least about 80 amino acids, more preferably at least about 85 amino acids, more preferably at least about 90 amino acids, more preferably at least about 95 amino acids, and even more preferably at least about 100 amino acids in length.

Additional preferred fragments of the present invention can include SEQ ID NO:64, SEQ ID NO:65, SEQ ID NO:66, SEQ ID NO:67, SEQ ID NO:68, SEQ ID NO:69, SEQ ID NO:70, and SEQ ID NO:71, as well as fragments of SEQ ID NO:6, SEQ ID NO:14, SEQ ID NO:27, and SEQ ID NO:33 that are not SEQ ID NO:64, SEQ ID NO:65, SEQ ID NO:66, SEQ ID NO:67, SEQ ID NO:68, SEQ ID NO:69, SEQ ID NO:70, and SEQ ID NO:71.

Additional preferred EcR and USP proteins of the present invention include proteins encoded by nucleic acid molecules comprising at least a portion of $nECR_{2822}$, $nECR_{1680}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, and $nUSP_{943}$, as well as EcR and USP proteins encoded by allelic variants of such nucleic acid molecules.

Also preferred are EcR proteins encoded by nucleic acid molecules having nucleic acid sequences comprising at least a portion of SEQ ID NO:5, SEQ ID NO:8, SEQ ID NO:13, and/or SEQ ID NO:16, as well as allelic variants of these nucleic acid molecules.

Also preferred are USP proteins encoded by nucleic acid molecules having nucleic acid sequences comprising at least a portion of SEQ ID NO:26, SEQ ID NO:29, SEQ ID NO:32, and/or SEQ ID NO:35, as well as allelic variants of these nucleic acid molecules.

In another embodiment, a preferred flea EcR protein of the present invention is encoded by a nucleic acid molecule comprising at least about 25 nucleotides, more preferably at least about 50 nucleotides, more preferably at least about 150 nucleotides, more preferably at least about 350 nucleotides, more preferably at least about 450 nucleotides, more preferably at least about 550 nucleotides, more preferably at least about 650 nucleotides, more preferably at least about 750 nucleotides, more preferably at least about 1000 nucleotides, more preferably at least about 1500 nucleotides, more preferably at least about 2000 nucleotides, more preferably at least about 2500 nucleotides, more preferably at least about 2800 nucleotides, more preferably at least about 3000 nucleotides, more preferably at least about 4000 nucleotides, and even more preferably at least about 4150 nucleotides in length, and a preferred flea USP protein of the present invention is encoded by a nucleic acid molecule comprising a coding region of at least about 25 nucleotides, more preferably at least about 50 nucleotides, more preferably at least about 100 nucleotides, more preferably at least about 150 nucleotides, more preferably at least about 250 nucleotides, more preferably at least about 500 nucleotides, more preferably at least about 800 nucleotides, more preferably at least about 1000 nucleotides, more preferably at least about 1250 nucleotides, more preferably at least about 1400 nucleotides, more preferably at least about 1750 nucleotides, more preferably at least about 1900 nucleotides, even more preferably at least about 1975 nucleotides in length. Within this embodiment is an EcR protein encoded by at least a portion of $nECR_{2822}$ or nECR4148 or by an allelic variant of either of these nucleic acid molecules and a USP protein encoded by at least a portion of $nUSP_{1749}$ or $nUSP_{1975}$ or by an allelic variant of either of these nucleic acid molecules. In yet another embodiment, preferred flea EcR and USP proteins of the present invention are encoded by nucleic acid molecules comprising apparently fill-length EcR or USP coding regions respectively, i.e., nucleic acid molecules encoding an apparently fill-length EcR or USP proteins.

Preferred arthropod EcR and USP proteins of the present invention are compounds that can be used to develop inhibitors that, when administered to an animal in an effective manner, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target includes any flea that produces a protein that can be targeted by an inhibitory compound that otherwise inhibits flea EcR or USP function (e.g., a compound that binds to flea EcR or USP thereby blocking flea development and/or migration regulatory pathways), thereby resulting in the decreased ability of the parasite to cause disease in an animal.

One embodiment of a flea EcR and/or USP protein of the present invention is a fusion protein that includes a flea EcR and/or USP protein-containing domain attached to one or more fusion segments. Suitable fusion segments for use with the present invention include, but are not limited to, segments that can: enhance a protein's stability; act as an immunopotentiator to enhance an immune response against a flea EcR and/or USP protein; and/or assist in purification of a flea EcR and/or USP protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea EcR-containing and/or USP-containing domain of the protein and can be susceptible to cleavage in order to enable straight-forward recovery of a flea EcR and/or USP protein. Fusion proteins are preferably produced by culturing a recombinant cell transformed with a fusion nucleic acid molecule that encodes a protein including the fusion segment attached to either the carboxyl and/or amino terminal end of an EcR-containing and/or USP-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea EcR and/or USP proteins of the present invention. As used herein, a mimetope of a flea EcR and/or USP protein of the present invention refers to any compound that is able to mimic the activity of such an EcR and/or USP protein, often because the mimetope has a structure that mimics the particular EcR and/or USP protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea EcR and/or USP nucleic acid molecule. The identifying characteristics of such nucleic acid molecules are heretofore described. A nucleic acid molecule of the present invention can include an isolated natural flea EcR and/or USP gene or a homolog thereof the latter of which is described in more detail below. A nucleic acid molecule of the present invention can include one or more regulatory regions, full-length or partial coding regions, or combinations thereof The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of an EcR and/or USP nucleic acid molecule of the present invention is from about 12 to about 18 nucleotides in length. Suitable and preferred fleas from which to isolate nucleic acid molecules of the present invention are disclosed herein. Particularly preferred EcR and/or USP nucleic acid molecules include *C. felis* EcR and/or USP nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea EcR and/or USP nucleic acid molecules of the present invention, or homologs thereof, can be isolated from a natural source or produced using recombinant DNA technology (e.g., polymerase chain reaction (PCR) amplification or cloning) or chemical synthesis. Isolated flea EcR and/or USP nucleic acid molecules, and homologs thereof, can include, for example, natural allelic variants and nucleic acid molecules modified by nucleotide insertions, deletions, substitutions, and/or inversions in a manner such that the modifications do not substantially interfere with the nucleic acid molecule's ability to encode an EcR and/or USP protein of the present invention.

A flea EcR and/or USP nucleic acid molecule homolog can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof Nucleic acid molecule homologs can be selected by hybridization with flea EcR or USP nucleic acid molecules or by screening the function of a protein encoded by the nucleic acid molecule (e.g., ability to elicit an immune response against at least one epitope of a flea EcR or USP protein or to effect EcR or USP activity).

An isolated nucleic acid molecule of the present invention can include a nucleic acid sequence that encodes at least one flea EcR or USP protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea EcR or USP protein.

A preferred nucleic acid molecule of the present invention, when administered to an animal, is capable of protecting that animal from flea infestation. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an EcR or USP protein of the present invention), the nucleic acid molecule being delivered to the animal, for example, by direct injection (i.e., as a genetic vaccine) or in a vehicle such as a recombinant virus vaccine or a recombinant cell vaccine.

In one embodiment of the present invention, a preferred flea EcR nucleic acid molecule includes an isolated nucleic acid molecule which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:10, SEQ ID NO:15, and SEQ ID NO:18.

In one embodiment of the present invention, a preferred flea USP nucleic acid molecule includes an isolated nucleic acid molecule which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:28, SEQ ID NO:31, SEQ ID NO:34, and SEQ ID NO:37.

Another embodiment of the present invention includes a nucleic acid molecule, wherein said nucleic acid molecule hybridizes, in a solution comprising 1×SSC and 0% formamide, at a temperature of about 52° C., to an isolated nucleic acid molecule selected from the group consisting of SEQ ID NO:5, SEQ ID NO:7, SEQ ID NO:8, SEQ ID NO:10, SEQ ID NO:13, SEQ ID NO:15, SEQ ID NO:16, SEQ ID NO:18, SEQ ID NO:26, SEQ ID NO:28, SEQ ID NO:29, SEQ ID NO:31, SEQ ID NO:32, SEQ ID NO:34, SEQ ID NO:35 and SEQ ID NO:37. Additional preferred nucleic acid molecules of the present invention include oligonucleotides of an isolated nucleic acid molecule, wherein said nucleic acid molecule hybridizes, in a solution comprising 1×SSC and 0% formamide, at a temperature of about 52° C., to an isolated nucleic acid molecule selected from the group consisting of SEQ ID NO:5, SEQ ID NO:7, SEQ ID NO:8, SEQ ID NO:10 SEQ ID NO:13, SEQ ID NO:15, SEQ ID NO:16, SEQ ID NO:18, SEQ ID NO:26, SEQ ID NO:28, SEQ ID NO:29, SEQ ID NO:31, SEQ ID NO:32, SEQ ID NO:34, SEQ ID NO:35 and SEQ ID NO:37, wherein said oligonucleotide comprises at least about 30 nucleotides.

Additional preferred flea EcR nucleic acid molecules of the present invention include nucleic acid molecules comprising a nucleic acid sequence that is preferably at least about 70%, more preferably at least about 75%, more preferably at least about 80% more preferably at least about 85%, more preferably at least about 90%, and even more preferably at least about 95% identical to a nucleic acid sequence selected from the group consisting of SEQ ID NO:5, SEQ ID NO:7, SEQ ID NO:8, SEQ ID NO:10, SEQ ID NO:13, SEQ ID NO:15, SEQ ID NO:16, and/or SEQ ID NO:18. Also preferred are oligonucleotides of any of such nucleic acid molecules, particularly those that are at least about 34 nucleotides. Percent identity may be determined using the program GCG Version 9.0-UNIX using default parameters.

Additional preferred flea USP nucleic acid molecules of the present invention include nucleic acid molecules comprising a nucleic acid sequence that is preferably at least about 70%, more preferably at least about 75%, more preferably at least about 80% more preferably at least about 85%, more preferably at least about 90%, and even more preferably at least about 95% identical to a nucleic acid sequence selected from the group consisting of SEQ ID NO:26, SEQ ID NO:28, SEQ ID NO:29, SEQ ID NO:31, SEQ ID NO:32, SEQ ID NO:34, SEQ ID NO:35, and/or SEQ ID NO:37. Also preferred are oligonucleotides of any of such nucleic acid molecules, particularly those that are at least about 30 nucleotides. Percent identity may be determined using the program GCG Version 9.0-UNIX using default parameters.

One embodiment of the present invention is a nucleic acid molecule comprising all or part of nucleic acid molecules $nECR_{2822}$, $nECR_{1680}$, $nECR_{666}$, $nECR_{4148}$, $nECR_{1683}$, $nECR_{612}$ $nUSP_{1749}$, $nUSP_{1344}$, $nUSP_{1975}$, $nUSP_{1422}$, $nUSP_{776}$, and $nUSP_{943}$, or allelic variants of these nucleic acid molecules. Another preferred nucleic acid molecule of the present invention includes at least a portion of nucleic acid sequence SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35, as well as allelic variants of nucleic acid molecules having these nucleic acid sequences and homologs of nucleic acid molecules having these nucleic acid sequences; preferably such a homolog encodes or is complementary to a nucleic acid molecule that encodes at least one epitope that elicits an immune response against a protein having an amino acid sequence SEQ ID NO:6, SEQ ID NO:14, SEQ ID NO:27 or SEQ ID NO:33. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an EcR nucleic acid molecule of the present invention encodes a protein that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to $PECR_{560}$ and/or $PECR_{561}$. In another embodiment, a USP nucleic acid molecule of the present invention encodes a protein that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to $PUSP_{448}$ and/or $PUSP_{474}$.

In another embodiment, an EcR nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:6 or SEQ ID NO:14. The present invention also includes an EcR nucleic acid molecule encoding a protein having at least a portion of SEQ ID NO:6, and/or SEQ ID NO:14, as well as allelic variants of an EcR nucleic acid molecule encoding a protein having these sequences, including nucleic acid molecules that have been modified to accommodate codon usage properties of the cells in which such nucleic acid molecules are to be expressed.

In another embodiment, a USP nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:27 or SEQ ID NO:33. The present invention also includes a USP nucleic acid molecule encoding a protein having at least a portion of SEQ ID NO:27, and/or SEQ ID NO:33, as well as allelic variants of a USP nucleic acid molecule encoding a protein having these sequences, including nucleic acid molecules that have been modified to accommodate codon usage properties of the cells in which such nucleic acid molecules are to be expressed.

In another embodiment, a preferred flea EcR nucleic acid molecule encodes an EcR protein comprising at least about 35 amino acids, preferably at least about 50 amino acids, more preferably at least about 100 amino acids, more preferably at least about 200 amino acids, more preferably at least about 300 amino acids, more preferably at least about 400 amino acids, more preferably at least about 500 amino acids, even more preferably at least about 560 amino acids in length.

In another embodiment, a preferred flea USP nucleic acid molecule encodes a USP protein comprising at least about at least about 35 amino acids, preferably at least about 50 amino acids, more preferably at least about 100 amino acids, more preferably at least about 200 amino acids, more preferably at least about 300 amino acids, more preferably at least about 400 amino acids, more preferably at least about 450 amino acids, even more preferably at least about 475 amino acids in length.

In another embodiment, a preferred flea EcR nucleic acid molecule comprises a nucleic acid sequence that encodes at least a portion of a flea EcR protein that is capable of binding to an ecdysone response element. Preferably, such nucleic acid molecule encodes a protein having SEQ ID NO:64 and/or SEQ ID NO:65. A preferred flea EcR protein also comprises at least a portion of a flea EcR protein that is capable of binding to ecdysone. Preferably, such nucleic acid molecule encodes a protein having SEQ ID NO:66 and/or SEQ ID NO:67.

In another embodiment, a preferred flea USP nucleic acid molecule comprises a nucleic acid sequence that encodes at least a portion of a flea USP DNA binding domain. Preferably, such nucleic acid molecule encodes a protein having SEQ ID NO:68 and/or SEQ ID NO:69. A preferred flea USP protein also comprises at least a portion of a flea USP ligand binding domain. Preferably, such nucleic acid molecule encodes a protein having SEQ ID NO:70 and/or SEQ ID NO:71.

In another embodiment, a preferred flea EcR nucleic acid molecule of the present invention comprises an apparently full-length EcR coding region, i.e., the preferred nucleic acid molecule encodes an apparently full-length EcR protein.

In yet another embodiment, a preferred flea USP nucleic acid molecule of the present invention comprises an apparently full-length USP coding region, i.e., the preferred nucleic acid molecule encodes an apparently full-length USP protein.

Knowing the nucleic acid sequences of certain flea EcR and/or USP nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea EcR and/or USP nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include flea $1^{st}$ instar larvae; $3^{rd}$ instar larvae, wandering larvae, prepupal larvae, pupae and whole adult flea cDNA libraries as well as genomic DNA libraries. Similarly, preferred DNA sources to screen or from which to amplify nucleic acid molecules include flea prepupal cDNA, adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. felis* EcR and/or USP nucleic acid molecules or other flea EcR and/or USP nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides, more preferably about 150 nucleotides, more preferably about 100 nucleotides and even more preferably about 50 nucleotides. The present invention includes oligonucleotides that can be used as, for example, probes to identify nucleic acid molecules, primers to produce nucleic acid molecules, or therapeutic reagents to inhibit flea EcR and/or USP protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea EcR and/or USP nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, or insect and mammalian cells, such as, but not limited to, tac, lac, trp, trc, oxy-pro, omp/lpp, rmB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nECR_{2822}$, $nECR_{1680}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, and $nUSP_{943}$.

Recombinant molecules of the present invention may also (a) contain secretory signals (i.e., signal segment nucleic acid sequences) to enable an expressed flea protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include $C.\ felis$ EcR and USP nucleic acid molecules disclosed herein. Particularly preferred nucleic acid molecules with which to transform a cell include $nECR_{2822}$, $nECR_{1680}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, and $nUSP_{943}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea EcR and/or USP proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include $Salmonella$, $Escherichia$, $Bacillus$, $Listeria$, $Saccharomyces$, $Spodoptera$, $Mycobacteria$, $Trichoplusia$, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are $Escherichia\ coli$, including $E.\ coli$ K-12 derivatives; $Salmonella\ typhi$; $Salmonella\ typhimurium$, including attenuated strains such as UK-1 $_\Pi 3987$ (×3987 UK-1 pStV11 Dcya-12 D(zid-62::Tn10) Dcrp-11 D(zhc-1431::Tn10) DasdA1 D(zhf-4::Tn10)) and SR-11 $_\Pi 4072$ (x4072 SR-11 pStSR1002 gyrA1816 Dcva1 Dcrp-1 DasdA1 D(zhf-4::Tn10) 24) (Curtiss, R., III, and S. M. Kelly. 1987. $Infect.\ Immun.$ 55:3035-3043.); $Spodoptera\ frugiperda$; $Trichoplusia\ ni$; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK[31] cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea EcR and/or USP nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea EcR and/or USP proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea EcR and/or USP protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea EcR and/or USP protein of the present invention or a mimetope thereof (e.g., anti-*C. felis* EcR or USP antibodies). As used herein, the term "selectively binds to" an EcR and/or USP protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-EcR or anti-USP antibody of the present invention preferably selectively binds to a flea EcR or USP protein respectively in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce EcR and/or USP proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from flea infestation. Therapeutic compositions of the present invention include at least one of the following protective compounds: an isolated antibody that selectively binds to a flea EcR or USP protein, or inhibitors of EcR and/or USP function identified by their ability to bind to a flea EcR and/or USP protein. Other protective compounds include for example, antisense-, triplex formation-ribozyme- and/or RNA drug-based technologies. As used herein, a protective compound refers to a compound that, when administered to an animal in an effective manner, is able to treat, ameliorate, and/or prevent flea infestation. Preferred fleas to target are heretofore disclosed. Examples of antibodies and inhibitors of the present invention are disclosed herein.

Additional therapeutic compositions of the present invention include a protective compound derived from a protein selected from the group consisting of: (a) an isolated flea ecdysone receptor protein selected from the group consisting of: (i) a protein comprising an amino acid sequence that is at least about 70% identical to an amino acid sequence selected from the group consisting of SEQ ID NO:6 and SEQ ID NO:14, wherein said protein is at least about 71 amino acid residues in length; (ii) a protein consisting of an amino acid sequence selected from the group consisting of SEQ ID NO:64, SEQ ID NO:66, and fragments thereof, wherein said protein has at least a portion of an ecdysone receptor DNA binding site; (iii) a protein consisting of an amino acid sequence selected from the group consisting of SEQ ID NO:65, SEQ ID NO:67, and fragments thereof, wherein said protein has at least a portion of an ecdysone receptor ligand binding site; and (iv) a protein encoded by an allelic variant of a nucleic acid molecule which encodes any protein of (i), (ii), or (iii); and (b) an isolated flea ultraspiracle protein selected from the group consisting of: (i) a protein comprising an amino acid sequence that is at least about 70% identical to an amino acid sequence selected from the group consisting of SEQ ID NO:27 and SEQ ID NO:33, wherein said protein is at least about 72 amino acid residues in length; (ii) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of an ultraspiracle protein that is capable of affecting binding of ecdysone receptor to ecdysone; and (iii) a protein encoded by an allelic variant of a nucleic acid molecule which encodes any protein of (i) or (ii); wherein said protective compound inhibits the binding between ecdysone receptor and ecdysone. As used herein, the term "derived from" refers to a natural EcR or USP DNA or protein of the present invention, a portion of a natural EcR or USP DNA or protein of the present invention, as well as, a compound designed using an EcR or USP DNA or protein of the present invention, such as, for example, proteins encoded by recombinant DNA, peptides, antibodies or small molecule inhibitors.

Suitable inhibitors of EcR and/or USP activity are compounds that inhibit EcR and/or USP protein activity, usually by binding to or otherwise interacting with or otherwise modifying the EcR and/or USP active site. EcR and/or USP inhibitors can also interact with other regions of the EcR and/or USP protein to inhibit EcR and/or USP activity, for example, by allosteric interaction. Inhibitors of EcR and/or USP are usually relatively small compounds and as such differ from anti-EcR and anti-USP antibodies. Preferably, an EcR and/or USP inhibitor of the present invention is identified by its ability to bind to, or otherwise interact with, a flea EcR and/or USP protein, thereby inhibiting the activity of the flea EcR and/or USP.

EcR and/or USP inhibitors can be used directly as compounds in compositions of the present invention to treat animals as long as such compounds are not harmful to host animals being treated. EcR and/or USP inhibitors can also be used to identify preferred types of flea EcR and/or USP to target using compositions of the present invention, for example by affinity chromatography. Preferred EcR and/or USP inhibitors of the present invention include, but are not limited to, flea EcR and/or USP substrate analogs, and other molecules that bind to a flea EcR and/or USP (e.g., to an allosteric site) in such a manner that EcR and/or USP activity of the flea EcR and/or USP is inhibited. An EcR and/or USP substrate analog refers to a compound that interacts with (e.g., binds to, associates with, modifies) the active site of an EcR and/or USP protein. A preferred EcR and/or USP substrate analog inhibits EcR and/or USP activity. EcR and/or USP substrate analogs can be of any inorganic or organic composition. EcR and/or USP substrate analogs can be, but need not be, structurally similar to an EcR and/or USP natural substrate as long as they can interact with the active site of that EcR and/or USP protein. EcR and/or USP substrate analogs can be designed using computer-generated structures of EcR and/or USP proteins of the present invention or computer structures of EcR's and/or USP's natural substrates. Preferred sites to model include one or more of the active sites of USP and/or EcR proteins. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea EcR and/or USP). A preferred EcR and/or USP substrate analog is a EcR and/or USP mimetic compound (i.e., a compound that is structurally and/or functionally similar to a natural substrate of an EcR and/or USP of the present invention, particularly to the region of the substrate that interacts with the EcR and/or USP active site, but that inhibits EcR and/or USP activity upon interacting with the EcR and/or USP active site).

Preferred EcR active sites include those portions of an EcR protein that binds to ecdysone, USP, and/or EcRE. Preferred USP active sites include those portions of a USP protein that binds to ecdysone, EcR, and/or EcRE.

EcR or USP peptides, mimetopes and substrate analogs, as well as other protective compounds, can be used directly as compounds in compositions of the present invention to treat animals as long as such compounds are not harmful to the animals being treated.

The present invention also includes a therapeutic composition comprising at least one flea EcR and/or USP-based compound of the present invention in combination with at least one additional compound protective against one or more infectious agents. Examples of such compounds and infectious agents are disclosed herein.

In one embodiment, a therapeutic composition of the present invention can be used to protect an animal from flea infestation by administering such composition to a flea in order to prevent infestation. Such administration could be oral, or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present in the blood of a host animal that has been administered a therapeutic composition of the present invention.

Therapeutic compositions of the present invention can be administered to any animal susceptible to such therapy, preferably to mammals, and more preferably to dogs, cats, humans, ferrets, horses, cattle, sheep and other pets, economic food animals, work animals and/or zoo animals. Preferred animals to protect against flea infestation include dogs, cats, humans and ferrets, with dogs and cats being particularly preferred.

In accordance with the present invention, a host animal (i.e., an animal that is or is capable of being infested with fleas) is treated by administering to the animal a therapeutic composition of the present invention in such a manner that the composition itself (e.g., an EcR and/or USP inhibitor, an EcR and/or USP synthesis suppressor (i.e., a compound that decreases the production of EcR and/or USP in fleas), an EcR and/or USP mimetope, or an anti-EcR or anti-USP antibody) or a product generated by the animal in response to administration of the composition (e.g., antibodies produced in response to administration of a flea EcR and/or USP protein or nucleic acid molecule, or conversion of an inactive inhibitor "prodrug" to an active EcR and/or USP inhibitor) ultimately enters the flea. A host animal is preferably treated in such a way that the compound or product thereof enters the blood stream of the animal. Fleas are then exposed to the composition or product when they feed from the animal. For example, flea EcR and/or USP inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing EcR and/or USP activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from flea infestation. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infestation in order to prevent infestation and/or can be administered to animals after infestation. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465-1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 µg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising an EcR and/or USP nucleic acid molecule of the present invention is administered according to a protocol that results in the animal producing a sufficient immune response to protect itself from flea infestation. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

One therapeutic composition of the present invention includes an inhibitor of flea EcR and/or USP activity, i.e., a compound capable of substantially interfering with the function of a flea EcR and/or USP susceptible to inhibition by an inhibitor of flea EcR and/or USP activity. An inhibitor of EcR and/or USP activity can be identified using flea EcR and/or USP proteins of the present invention. One embodiment of the present invention is a method to identify a compound capable of inhibiting EcR and/or USP activity of a flea. Such a method includes the steps of (a) contacting (e.g., combining, mixing) an isolated flea EcR and/or USP protein, preferably a *C. felis* EcR and/or USP protein of the present invention, with a putative inhibitory compound under conditions in which, in the absence of the compound, the protein has EcR and/or USP activity, and (b) determining if the putative inhibitory compound inhibits the EcR and/or USP activity. As used herein, the term "EcR activity" means the ability of EcR to bind to or otherwise interact with ecdysone, USP and/or EcRE and thereby affect DNA transcription. As used herein, the term "USP activity" means the ability of USP to bind to or otherwise interact with ecdysone, EcR and/or EcRE, preferably the ability to affect the association of EcR with ecdysone, more preferably the ability to promote, improve and/or enhance the association between EcR and ecdysone, thereby affecting DNA transcription.

Another embodiment of a method to identify a compound capable of inhibiting EcR and/or USP activity of a flea includes the steps of (a) contacting an isolated flea EcR and/or USP protein, preferably a *C. felis* EcR and/or USP protein of the present invention, with a putative inhibitory compound under conditions in which the EcR and/or USP protein can bind to the putative inhibitory compound, and (b) determining if the putative inhibitory compound binds to the EcR and/or USP protein.

Putative inhibitory compounds to screen include small organic molecules, antibodies (including mimetopes thereof) and substrate analogs. Methods to determine EcR and/or USP activity are known to those skilled in the art; see, for example, the Examples section of the present application. Methods to determine binding of a putative inhibitory compounds to an EcR and/or USP protein are known to those of skill in the art and include, for example, determining changes in molecular mass using surface plasmon resonance (e.g., determining light scatter by an inhibitor or an EcR and/or USP protein, before and after contacting the inhibitor or protein with an EcR and/or USP protein or inhibitor, respectively).

One embodiment of the present invention is a method to identify proteins that specifically interact with an EcR or USP protein of the present invention. The method can comprise the steps of a) identifying and isolating a protein-binding domain of an isolated flea EcR or USP protein; b) contacting that protein-binding domain with isolated flea proteins under conditions such that a flea protein and the protein-binding domain can selectively interact and/or bind to each other, using, for example, the yeast two-hybrid system see, for example, Luban, et al., 1995, *Curr. Opin. Biotechnol.*, 6, 59-64; and c) identifying those proteins that specifically bind to the isolated EcR or USP protein-binding domain. Additional methods to identify protein-protein interactions with the protein-binding domains of an isolated EcR or USP protein of the present invention are known to those skilled in the art. Examples include Biacore® screening, confocal immunofluorescent microscopy, and immunoprecipitations.

An inhibitor of EcR and/or USP function can be identified using flea EcR and/or USP proteins of the present invention. A preferred inhibitor of EcR and/or USP function is a compound capable of substantially interfering with the function of a flea EcR and/or USP protein and which does not substantially interfere with host animal EcR and/or USP activity. As used herein, a compound that does not substantially inhibit host animal EcR and/or USP activity is one that, when administered to a host animal, the host animal shows no significant adverse effects attributable to the compound and which, when administered to an animal in an effective manner, is capable of protecting that animal from flea infestation.

A preferred method to identify a compound capable of inhibiting EcR and/or USP activity includes contacting an isolated flea EcR and/or USP protein having an amino acid sequence selected from the group consisting of SEQ ID NO:6, SEQ ID NO:14, SEQ ID NO:27, and SEQ ID NO:33 with a putative inhibitory compound under conditions in which, in the absence of said compound, said protein has EcR and/or USP activity; and determining if said putative inhibitory compound inhibits said activity. An additional preferred method of identifying a compound capable of inhibiting flea EcR and/or USP activity includes contacting an isolated host animal EcR and/or USP protein with the putative EcR and/or USP inhibitory compound under conditions in which, in the absence of said compound, said host animal EcR and/or USP protein has EcR and/or USP activity; and determining if said putative inhibitory compound inhibits the host animal EcR and/or USP activity.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This Example describes the preparation of a head and nerve cord cDNA pool from the flea *Ctenocephalides felis*.

A flea head and nerve cord cDNA pool was prepared using Clonetech's MARATHON™ cDNA Amplification kit and protocol, available from Clonetech Laboratories, Palo Alto, Calif. Briefly, head and nerve cords from 100 fed and 100 unfed adult fleas were isolated and about 8 µg of total RNA was extracted and used for a first strand cDNA synthesis reaction with AMV reverse transcriptase. Five microliters (µl) of the first reaction product was used as the template in a second strand cDNA reaction, using Clonetech's second strand enzyme cocktail and protocols, to yield double stranded cDNA. Marathon cDNA adaptors were ligated to double stranded cDNA using T4 DNA ligase according to the manufacturer's instructions.

EXAMPLE 2

This example describes the cloning and sequencing of flea ecdysone receptor (EcR) nucleic acid molecules.

Degenerate primers were designed based on several conserved regions of published EcR amino acid sequences of *Bombyx mori*, Swevers et al., 1995, ibid., *Drosophila melanogaster*, Koelle et al., 1991, ibid., and *Manduca sexta*, Fujiwara et al., 1995, ibid., and human retinoic acid receptor alpha-1 sequence, Giguere et al., 1987, ibid. Sense primer JER-2, having the nucleotide sequence 5' TGY GAA ATG GAY ATG TAY ATG 3' (wherein Y represents C or T), designated herein as SEQ ID NO:44, was used in combination with antisense primer JER-4, having the nucleotide sequence 5' CCY TTW GCR AAT TCN ACD AT 3' (wherein Y represents C or T, W represents A or T, R represents A or G, N represents A, T, C or G, and D represents A or G or T), designated herein as SEQ ID NO:45, to produce a PCR product from a flea mixed instar cDNA library, prepared as described in Example 11 of PCT Publication WO 98/21324. PCR reaction were performed using the following amplification cycles: (1) one cycle at 95° C. for three minutes; (2) thirty-five cycles at 95° C. for thirty seconds, 50° C. for thirty seconds, and 72° C. for one minute; and (3) one cycle of 72° C. for nine minutes, in reactions containing 1.5 millimolar (mM) $MgCL_2$, 0.2 mM dNTPs, 1 µM of each primer, 1 µl of 5 units per microliter (U/µl) Taq polymerase, and 1 µl of template. The reaction product was re-amplified under the same reaction conditions except that part (2) ran for only twenty-five cycles. The resulting PCR amplification product was a fragment of about 446 nucleotides, denoted herein as $nECR_{446}$. The PCR product was purified using Qiagen's Qiaquick™ kit using the manufacturer's protocol, available from Qiagen, Chatsworth, Calif., and sequenced using primers JER-2 and JER-4 using standard sequencing methods. The resulting nucleic acid sequence of $nECR_{446}$ has a coding strand presented herein as SEQ ID NO:1 and a complementary strand presented herein as SEQ ID NO:2.

$nECR_{446}$ was used as the template for a second PCR reaction using sense primer BER-1, having nucleotide sequence 5' GGT TCC CGA AAA CCA ATG 3', designated herein as SEQ ID NO:46, and anti-sense primer BER-2, having nucleotide sequence 5' GCC GAA ATT CAA GAG CTT C3', designated herein as SEQ ID NO:47. PCR reactions were performed using the following amplification cycles: (1) one cycle at 95° C. for two minutes and forty seconds; (2) thirty-five cycles at 95° C. for thirty seconds, 52.8° C. for thirty seconds, and 72° C. for one minute; and (3) one cycle at 72° C. for eight minutes, in reactions containing 1.5 mM $MgCL_2$, 0.2 mM dNTPs, 1 μM of each primer, 1 μl of 5 U/μl Taq polymerase, and 1 μl of template. The resulting PCR amplification product was a fragment of about 350 nucleotides, denoted herein as $nECR_{350}$. The PCR product was purified using the Qiaquick™ kit and sequenced using primers BER-1 and BER-2 using standard sequencing methods. The resulting nucleic acid sequence of $nECR_{350}$ has a coding strand presented herein as SEQ ID NO:3 and a complementary strand presented herein as SEQ ID NO:4.

A DNA probe comprising nucleotides from $nECR_{350}$, SEQ ID NO:3, was labeled with $^{32}P$ and used to screen about 300,000 plaques from the flea mixed instar cDNA library and a flea pre-pupal cDNA library prepared as described in Example 11 of PCT Publication WO 98/21324. The following hybridization conditions were used. Filters were hybridized with about $1 \times 10^6$ counts per minute (cpm) per ml of the probe in 5× sodium chloride-sodium phosphate-ethylenediaminetetraacetic acid, hereinafter referred to as "SSPE", 1% Sarcosyl, 0.1 mg/ml salmon sperm DNA and 0.1 mg/ml BLOTTO at 45° C. for about 14 hours. The filters were washed twice for 30 minutes per wash in 500 ml of 5×SSPE, 1% Sarcosyl at 45° C., hereinafter referred to as "standard EcR hybridization conditions". A positive plaque, denoted herein as EcR3 was further screened to obtain a pure plaque population. In vivo excision was performed using the Stratagene Ex-Assist™ helper phage system and protocols, to convert ten positive plaques to pBluescript plasmid DNA. Multiple clones were sequenced following preparation with a Qiagen Qiaprep™ spin mini prep kit using the manufacturer's instructions and restriction enzyme digestion with about 20 U/μl each of EcoRI and XhoI, available from New England Biolabs, Beverly, Mass. A clone was isolated from a tertiary plaque of EcR3, containing a nucleic acid molecule of about 2822 base pairs, referred to herein as $nECR_{2822}$, having a nucleotide sequence denoted herein as SEQ ID NO:5. The complement of SEQ ID NO:5 is represented herein as SEQ ID NO:7.

Translation of SEQ ID NO:5 suggests that nucleic acid molecule $nECR_{2822}$ encodes a full-length EcR protein of 560 amino acids, referred to herein as $PECR_{560}$, having an amino acid sequence represented by SEQ ID NO:6, assuming the initiation codon spans from nucleotide 605 through nucleotide 607 of SEQ ID NO:5 and the termination codon spans from nucleotide 2285 through nucleotide 2287 of SEQ ID NO:5. The coding region encoding $PECR_{560}$, is represented by nucleic acid molecule $nECR_{1680}$, having a coding strand with the nucleic acid sequence represented by SEQ ID NO:8 and a complementary strand with nucleic acid sequence represented by SEQ ID NO:10. The amino acid sequence of $PECR_{560}$ predicts that $PECR_{560}$ has an estimated molecular weight of about 61.8 kilodaltons (kDa) and an estimated pI of about 6.5. A DNA probe comprising nucleotide 318 through nucleotide 2287 of SEQ ID NO:5 was labeled with $^{32}P$ and used to probe separate samples of C. felis genomic DNA which had been digested with EcoRI and EcoRV, respectively. One to three bands of digested DNA hybridized with labeled probes, under standard EcR hybridization conditions described herein indicating that each of these genes are single copy number in genes.

Comparison of amino acid sequence SEQ ID NO:6 with amino acid sequences reported in GenBank indicates that SEQ ID NO:6 showed the most homology, i.e., about 64% identity between SEQ ID NO:6 and a Drosophila melanogaster EcR protein isoform B1, GenBank Accession No. P34021 (SEQ ID NO:75). Comparison of SEQ ID NO:8 with nucleic acid sequences reported in GenBank indicates that SEQ ID NO:8 showed the most homology, i.e., about 63% identity between SEQ ID NO:8 and a Lucilia cuprina EcR nucleic acid molecule, GenBank Accession number U75377 (SEQ ID NO:74). Percent identity calculations were performed using GCG version 9.0-UNIX using default parameters.

An isoform of flea EcR was isolated as follows. Primer BER-10, having the nucleotide sequence 5' GTC AGG AAT GTA GGC TCA 3', designated herein as SEQ ID NO:48 and corresponding to nucleotides 1015 through 1032 of nucleic acid molecule $nECR_{2822}$ was used in combination with vector primer T3, having the nucleotide sequence 5' AAT TAA CCC TCA CTA AAG GG 3', designated herein as SEQ ID NO:49, to generate a PCR product from a primary phage plaque, denoted EcR8, which hybridized to $nECR_{350}$ using standard EcR hybridization conditions. PCR reaction were performed using the following amplification cycles: (1) one cycle at 95° C. for two minutes and forty seconds; (2) thirty-five cycles at 95° C. for thirty seconds, 50° C. for one minute, and 72° C. for two minutes; and (3) one cycle at 72° C. for eight minutes, in reactions containing 1.5 mM $MgCL_2$, 0.2 mM dNTPs, 1 μM of each primer, 1 μl of 5 U/μl Taq polymerase, and 1 μl of template, hereinafter referred to as "standard PCR conditions". The resulting PCR amplification product was a fragment of about 666 base pairs, denoted herein as $nECR_{666}$. The PCR product was purified using the Qiaquick™ kit and sequenced using primers BER-10 and T3 using standard sequencing methods. The resulting nucleic acid sequence of nECR666 has a coding strand presented herein as SEQ ID NO:11 and a complementary strand presented herein as SEQ ID NO:12.

A DNA probe comprising nucleotides from $nECR_{666}$, SEQ ID NO:11, was labeled with $^{32}P$, and used to re-screen EcR8 primary phage plaques until a pure plaque population was obtained. In vivo excision was performed using Stratagene Ex-Assist™ helper phage system and protocols, to convert positive plaques to pbluescript plasmid DNA. Multiple clones were sequenced following preparation with the Qiaprep™ spin mini prep kit and restriction enzyme digestion with 20 U/μl each of EcoRI and XhoI. A clone was isolated having an about 4148 base pair insert, referred to herein as $nECR_{4148}$, having a nucleotide sequence denoted herein as SEQ ID NO:13. The complement of SEQ ID NO:13 is represented herein by SEQ ID NO:15.

Translation of SEQ ID NO:13 suggests that nucleic acid molecule $nECR_{4148}$ encodes a full-length EcR protein of 561 amino acids, referred to herein as $PECR_{561}$, having an amino acid sequence represented by SEQ ID NO:14, assuming the initiation codon spans from nucleotide 184 through nucleotide 186 of SEQ ID NO:13 and the termination codon spans from nucleotide 1867 through nucleotide 1869 of SEQ ID NO:13. The coding region encoding $PECR_{561}$, is represented by nucleic acid molecule $nECR_{1683}$, having a coding strand with the nucleic acid sequence represented by SEQ ID NO:16 and a complementary strand with nucleic acid sequence represented by SEQ ID NO:18. The amino acid sequence of $PECR_{561}$ predicts that PECR561 has an estimated molecular weight of about 62.6 kDa and an estimated pI of about 7.

Comparison of amino acid sequence SEQ ID NO:14 with amino acid sequences reported in GenBank indicates that SEQ ID NO:14 showed the most homology, i.e., about 66% identity between SEQ ID NO:14 and a Drosophila melanogaster EcR protein isoform A, GenBank Accession No. P34021 (SEQ ID NO:75). Comparison of SEQ ID NO:16 with nucleic acid sequences reported in GenBank indicates that SEQ ID NO:16 showed the most homology, i.e., about 59% identity between SEQ ID NO:16 and a *Lucilia cuprina* EcR nucleic acid molecule, GenBank Accession No. U75355 (SEQ ID NO:76). A comparison of $nECR_{2822}$ and $nECR_{4148}$ indicates that these molecules represent different variants of EcR in *C. felis*. Percent identity calculations were performed using GCG version 9.0-UNIX using default parameters.

EXAMPLE 3

This example describes the cloning and sequencing of flea ultraspiracle (USP) nucleic acid molecules.

Degenerate primers were designed based on several conserved regions of published USP amino acid sequences of *Bombyx mori*, Tzertzinis et al., 1994, ibid., *Drosophila melanogaster*, Oro et al., 1990, ibid, and *Manduca sexta*, Jindra et al., ibid., published amino acid sequences of human retinoic acid receptor RXR-gamma, Cooke et al., 1996, ibid., mouse retinoic acid receptor RXR-gamma, Leid et al., 1992, ibid., and *Xenopus laevis* retinoic acid receptor RXR-alpha, Blumberg et al., 1992, ibid. Sense primer B-USP-1 having the nucleotide sequence 5' GGW AAA CAY TAT GGW GTW TA 3' (wherein W represents A or T, and Y represents C or T), designated herein as SEQ ID NO:50, was used in combination with antisense primer B-USP-3, having the nucleotide sequence 5' TTC TTC YTG NAC WHC TTC 3' (wherein Y represents C or T, N represent A or T or C or G, and W represents A or T), designated herein as SEQ ID NO:51, to produce a PCR product from the flea pre-pupal cDNA library, using standard PCR conditions described in Example 2. The resulting PCR amplification product was a fragment of about 160 nucleotides, denoted herein as $nUSP_{160}$. The PCR product was purified using Qiagen's Qiaquick™ kit and protocol and cloned into the pCRII TA™ vector, available from Invitrogen, San Diego, Calif., according to the manufacturer's instructions. Clones were prepared using Qiagen's QIAprep™ spin mini prep kit and protocol and screened by restriction enzyme digest using 20 U/µl EcoRI. One screened clone was isolated and sequenced using TA+ and TA− primers, available from InVitrogen, The resulting nucleic acid sequence of $nUSP_{160}$ has a coding strand presented herein as SEQ ID NO:19 and a complementary strand presented herein as SEQ ID NO:20.

A DNA probe comprising nucleotides from $nUSP_{160}$, SEQ ID NO:19, was labeled with $^{32}P$ and used to screen about 450,000 plaques from the flea pre-pupal cDNA library described in Example 2, using the following hybridization conditions. Filters were hybridized with about $1 \times 10^6$ counts per minute (cpm) per ml of the probe in 5× SSPE, 1% Sarcosyl, 0.1 mg/ml salmon sperm DNA and 0.1 mg/ml BLOTTO at 45° C. for about 14 hours. The filters were washed twice for 30 minutes per wash in 500 ml of 5×SSPE, 1% Sarcosyl at 45° C., hereinafter referred to as "standard USP hybridization conditions". Two positive plaques, denoted herein as USP11 and USP12, were further screened to obtain pure plaque populations of each plaque. In vivo excision was performed using Stratagene Ex-Assist™ helper phage system and protocols, to convert positive plaques to pbluescript plasmid DNA. Clones USP11 and USP12 were sequenced following preparation with the Qiaprep™ spin mini prep kit and restriction enzyme digestion with 20 U/µl each of EcoRI and XhoI. A clone from plaque USP11 was isolated having an about 1421 base pair insert, referred to herein as $nUSP_{1421}$, having a nucleotide sequence denoted herein as SEQ ID NO:23. The complement of SEQ ID NO:23 is represented herein by SEQ ID NO:24.

Sequence analysis revealed that $nUSP_{1421}$ was truncated at the 5' end. Additional 5' sequence was determined as follows. Antisense primer B-USP-5, having nucleotide sequence 5' TTC TCG TTT CAT TCC ACA GG 3', designated herein as SEQ ID NO:52, which corresponds to nucleotides 141 to 160 of $nUSP_{160}$, was used in combination with primer T3, SEQ ID NO:49, to create a PCR product using the primary USP11 phage plug as the template and standard PCR conditions. The resulting about 819 base pair PCR product, referred to herein as $nUSP_{819}$, designated herein as SEQ ID NO:25, was sequenced and nucleotides 646 through 819 of $nUSP_{819}$ were found to overlap with nucleotides 11 through 185 of $nUSP_{1421}$.

Primers based upon the combined sequences of $nUSP_{1421}$ and $nUSP_{819}$, were used to produce a PCR product from the flea pre-pupal cDNA library containing a non-truncated 5' end. Sense primer USP11-5O, having nucleotide sequence 5' AAA GGG AAC AAA AGC TGG AGC TCC ACC GC 3', designated herein as SEQ ID NO:53, was used in combination with antisense primer USP11-3O, having the nucleotide sequence 5' TTA AAA TAT CAC TGG TTC GTA TCC TCC C 3', designated herein as SEQ ID NO:54, to produce the PCR product. The product from this first PCR reaction was used as the template in a second PCR reaction using sense primer USP11-5I, having the nucleotide sequence 5' GGC GGC CGC TCT AGA ACT AGT GGA TC 3', designated herein as SEQ ID NO:55, and antisense primer USP11-3I, having the nucleotide sequence 5' AGA CAA TCA ATA TCC CAA GTG CG 3', designated herein as SEQ ID NO:56, under standard PCR conditions as described in Example 2. The resulting PCR product was a fragment of about 1749 base pairs, denoted herein as $nUSP_{1749}$. The PCR product was purified using the Qiaquick™ kit and cloned into the pCRII TA™ vector, using the manufacturer's instructions. Clones were prepared using the QIAprep™ spin mini prep kit and preferred clones were identified by restriction enzyme digestion using 20 U/µl EcoRI. One clone was isolated and sequenced using TA+ and TA− primers. The resulting nucleic acid sequence of $nUSP_{1749}$ has a coding strand presented herein as SEQ ID NO:26 and a complementary strand presented herein as SEQ ID NO:28.

Translation of SEQ ID NO:26 suggests that nucleic acid molecule $nUSP_{1749}$ encodes a full-length USP protein of 448 amino acids, referred to herein as $PUSP_{448}$, having an amino acid sequence represented by SEQ ID NO:27, assuming the initiation codon spans from nucleotide 306 through nucleotide 308 of SEQ ID NO:26 and the termination codon spans from nucleotide 1650 through nucleotide 1652 of SEQ ID NO:26. The coding region encoding $PUSP_{448}$, is represented by nucleic acid molecule $nUSP_{1344}$, having a coding strand with the nucleic acid sequence represented by SEQ ID NO:29 and a complementary strand with nucleic acid sequence represented by SEQ ID NO:31. The amino acid sequence of $PUSP_{448}$ predicts that $PUSP_{448}$ has an estimated molecular weight of about 49.6 kDa and an estimated pI of about 8.

Comparison of amino acid sequence SEQ ID NO:27 with amino acid sequences reported in GenBank indicates that SEQ ID NO:27 showed the most homology, i.e., about 58% identity between SEQ ID NO:27 and a *Drosophila melanogaster* steroid hormone receptor like protein, GenBank Accession No. S13119 (SEQ ID NO:77). Comparison of SEQ ID NO:29 with nucleic acid sequences reported in GenBank indicates that SEQ ID NO:29 showed the most homology, i.e., about 57% identity between SEQ ID NO:29 and a *Manduca sexta* USP-1 nucleic acid molecule, GenBank Accession No. U44837 (SEQ ID NO:78). Percent identity calculations were performed using GCG version 9.0-UNIX using default parameters.

A clone from plaque USP12 was isolated having an about 2149 base pair insert, referred to herein as nUSP$_{2149}$, having a nucleotide sequence denoted herein as SEQ ID NO:21. The complement of SEQ ID NO:21 is represented herein by SEQ ID NO:22. Sequence analysis revealed that nUSP$_{2149}$ contains an unusual 3' end that is not homologous to published USP sequences, therefore additional 3' sequence was determined as follows. Sense primer USP12-5I, having the nucleotide sequence 5' CTG CAT AAA ATG CCT AAA GTC GCG GAC 3', designated herein as SEQ ID NO:57, was used in combination with antisense primer USP11-3I, SEQ ID NO:56, to produce a PCR product using 5 µl of a 1:50 dilution of the flea head and nerve cord RACE cDNA pool described in Example 1 under standard PCR conditions. The resulting PCR product was a fragment of about 1975 base pairs, denoted herein as nUSP$_{1975}$. The PCR product was purified using Qiagen's Qiaquick™ kit and cloned into the pCRII TA™ vector. Clones were prepared using a Biorad Quantum™ mini prep kit and the manufacturer's protocol, available from Biorad, Hercules, Calif., and preferred clones were identified by restriction enzyme digest using 20 U/µl EcoRI. One clone was isolated and sequenced using TA+ and TA- primers. The resulting nucleic acid sequence of nUSP$_{1975}$ has a coding strand presented herein as SEQ ID NO:32 and a complementary strand presented herein as SEQ ID NO:34.

Translation of SEQ ID NO:32 suggests that nucleic acid molecule nUSP$_{1975}$ encodes a full-length USP protein of 474 amino acids, referred to herein as PUSP$_{474}$, having an amino acid sequence represented by SEQ ID NO:33, assuming the initiation codon spans from nucleotide 454 through nucleotide 456 of SEQ ID NO:32 and the termination codon spans from nucleotide 1876 through nucleotide 1878 of SEQ ID NO:32. The coding region encoding PUSP$_{474}$ is represented by nucleic acid molecule nUSP$_{1422}$, having a coding strand with the nucleic acid sequence represented by SEQ ID NO:35 and a complementary strand with nucleic acid sequence represented by SEQ ID NO:37. The amino acid sequence of PUSP$_{474}$ predicts that PUSP$_{474}$ has an estimated molecular weight of about 52 kDa and an estimated pI of about 8.4. A DNA probe comprising nucleotide 99 through nucleotide 1878 of SEQ ID NO:32 was labeled with $^{32}$P and used to probe separate samples of *C. felis* genomic DNA which had been digested with EcoRI and EcoRV, respectively. One to three bands of digested DNA hybridized with labeled probes, using standard USP hybridization conditions described herein, indicating that each of these genes are single copy number in genes.

Comparison of amino acid sequence SEQ ID NO:33 with amino acid sequences reported in GenBank indicates that SEQ ID NO:33 showed the most homology, i.e., about 56% identity between SEQ ID NO:33 and a *Drosophila melanogaster* steroid hormone receptor-like protein, GenBank Accession No. S13119 (SEQ ID NO:77). Comparison of SEQ ID NO:35 with nucleic acid sequences reported in GenBank indicates that SEQ ID NO:35 showed the most homology, i.e., about 51% identity between SEQ ID NO:35 and a nucleic acid molecule encoding a *Drosophila melanogaster* steroid hormone receptor-like protein, GenBank Accession No. X52591 (SEQ ID NO:79). A comparison of nUSP$_{1749}$ and nUSP$_{1975}$ indicates that these molecules represent different variants of USP in *C. felis*. Percent identity calculations were performed using GCG version 9.0-UNIX using default parameters.

EXAMPLE 4

This example describes the expression of *C. felis* EcR and USP proteins.

A. EcR Expression

A putative ligand binding site of *C. felis* EcR spanning nucleotide 1549 to nucleotide 2161 of SEQ ID NO:5, referred to herein as nECR$_{612}$, having a coding strand with the nucleic acid sequence represented by SEQ ID NO:38 and a complementary strand with nucleic acid sequence represented by SEQ ID NO:39, was isolated and expressed as follows. Primer EcR-LBD-F, having nucleotide sequence 5' GCG GGA TCC CAA GAT GGA TAT GAA CAA CCT 3', designated herein as SEQ ID NO:58 and having a BamHI site indicated in bold, was used in combination with antisense primer EcR-LBD-R, having nucleotide sequence 5' GCG GAA TTC TCA ATC CCA AAT TTC TTC TAA AAA TCT 3', designated herein as SEQ ID NO:59 and having an EcoRI site indicated in bold, to produce a PCR product under standard PCR conditions using nECR$_{2822}$ as the template. The resulting PCR product was cut with 20 (U/µl) each of EcoRI and BamHI restriction endonucleases, and subcloned into pGEX-6P1 expression vector, available from Pharmacia, Piscataway, N.J., which had been cut with EcoRI and BamHI. The resulting recombinant molecule, referred to herein as pGEX-nECR$_{612}$, was transformed into *E. coli* strain BL21, available from Novagen, Madison, Wis., to form recombinant cell *E. coli*:pGEX-nECR$_{612}$. Colonies were screened by restriction enzyme digestion with 20 U/µl each of BamHI and EcoRI after DNA was isolated using the Qiaspin™ Mini Prep kit. Preferred colonies were then incubated in the presence of 1 mM isopropylthio-β-galactoside (IPTG) to induce expression of recombinant protein. Expression of protein was confirmed using antibodies that bind to the GST tag and Western Blot analysis which showed expression of an about 55 kD protein.

B. USP Expression

A putative ligand binding site of *C. felis* USP spanning nucleotide 857 to nucleotide 1633 of SEQ ID NO:26, referred to herein as nUSP$_{776}$, having a coding strand with the nucleic acid sequence represented by SEQ ID NO:40 and a complementary strand with nucleic acid sequence represented by SEQ ID NO:41, was isolated and expressed as follows. Primer USP-LBD-F, having nucleotide sequence 5' GCG GGA TCC CTC TGT TCG AGA TTT AAC GGT A 3', designated herein as SEQ ID NO:60 and having a BamHI site indicated in bold, was used in combination with antisense primer USP-LBD-R, having nucleotide sequence 5' GCG AAG CTT TCA ACC GAT GGG TCC GCC 3', designated herein as SEQ ID NO:61 and having a HindIII site indicated in bold, to produce a PCR product under standard PCR conditions using nUSP$_{1749}$ as the template. The resulting PCR product was cut with 20 U/µl each of BamHI and HindIII restriction endonucleases, and subcloned into the pTrc-His-B expression vector, available from Invitrogen, which had been cut with BamHI and HindIII. The resulting recombinant molecule, referred to herein as pTrc-His-nUSP$_{776}$ was transformed into *E. coli* strain BL21 to form recombinant cell *E. coli*:pTrc-nUSP$_{718}$. Colonies were screened by restriction enzyme digestion with 20 U/µl each of BamHI and HindIII after DNA was isolated using the Qiaspin™ Mini Prep kit. Preferred colonies were then incubated in the presence of 1 mM IPTG to induce expression of recombinant protein.

Expression of protein was confirmed using antibodies that bind to the T7 tag and Western Blot analysis which showed expression of an about 36 kD protein.

C. EcR and USP co-expression

The ligand binding sites of *C. felis* EcR and USP described in Example 3A and 3B were co-expressed as follows. The recombinant molecule pTrc-His-nUSP$_{776}$ was used as the template in a PCR reaction using sense primer USP-GEX-LBD-F, having nucleotide sequence 5' GCG CCC GGG GGA TTA ACT TTA TTA TTA AAA ATT AAA 3', designated herein as SEQ ID NO:62 and having an XmaI site indicated in bold, and antisense primer USP-GEX-LBD-R, having nucleotide sequence 5' GCG CGC GGC CGC AAG CTT TCA ACC GAT GGG TCC 3', designated herein as SEQ ID NO:63 and having a NotI site indicated in bold. PCR reactions were performed using the following conditions: (1) one cycle at 95° C. for two minutes and forty seconds; (2) thirty-five cycles at 95° C. for thirty seconds, 52° C. for thirty seconds, and 72° C. for one minute and thirty seconds; and (3) one cycle at 72° C. for seven minutes, in reactions containing 1.5 mM MgCL$_2$, 0.2 mM dNTPs, 1 µM of each primer, 1 µl of 5 U/µl Taq polymerase, and 1 µl of template. The resulting PCR product was a fragment of about 943 base pairs containing the ribosome binding site of pTrc-His and the ligand binding site of USP, designated herein as nUSP$_{943}$, having a coding strand with the nucleic acid sequence represented by SEQ ID NO:42 and a complementary strand with nucleic acid sequence represented by SEQ ID NO:43.

A dicistronic vector containing the ligand binding sites of USP and EcR was produced as follows. The recombinant molecule pGEX-nECR$_{612}$ and the PCR product nUSP$_{943}$, each were digested with 10 U/µl of XmaI and NotI restriction endonucleases, available from New England Biolabs. The two restriction enzyme digested products were combined and allowed to ligate to form a recombinant molecule designated pGEX-EcR$_{612}$-USP$_{943}$, which was transformed into *E. coli* strain BL21 to form the recombinant cell referred to as *E. coli*:pGEX-EcR$_{612}$-USP$_{943}$.

Colonies were screened by restriction enzyme digestion with 20 U/µl each of BamHI and NotI after DNA was isolated using the Qiaspin™ Mini Prep kit. Selected colonies were then incubated in the presence of 1 mM IPTG to induce expression of recombinant protein. Expression of the recombinant proteins was confirmed by Western Blot analysis using antibodies that bind specifically to the T7 tag and the GST tag of the recombinant proteins. The resulting Western identified an about 55 kD protein and an about 36 kD protein.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

This invention claimed is:

1. An isolated nucleic acid molecule comprising a nucleic acid sequence selected from the group consisting of:
   (a) a nucleic acid sequence that encodes a protein comprising SEQ ID NO:33, SEQ ID NO:70 or SEQ ID NO:71; and,
   (b) a nucleic acid sequence fully complementary to a nucleic acid sequence of (a).

2. A recombinant molecule comprising a nucleic acid molecule as set forth in claim 1 operatively linked to a transcription control sequence.

3. A recombinant cell comprising a nucleic acid molecule as set forth in claim 1.

4. An isolated nucleic acid molecule selected from the group consisting of:
   (a) a nucleic acid sequence comprising SEQ ID NO:32 or SEQ ID NO:35; and,
   (b) a nuclei acid sequence fully complementary to a nucleic acid sequence of (a).

5. A recombinant molecule comprising a nucleic acid molecule as set forth in claim 4 operatively linked to a transcription control sequence.

6. An isolated nucleic acid molecule consisting of a nucleic acid sequence selected from the group consisting of:
   (a) a nucleic acid sequence encoding a protein consisting of SEQ ID NO:33, SEQ ID NO:70 or SEQ ID NO:71; and
   (b) a nucleic acid sequence consisting of SEQ ID NO:32, SEQ ID NO:34 or SEQ ID NO:35; and
   (c) a nucleic acid sequence fully complementary to the nucleic acid sequence of (a) or (b).

* * * * *